(12) United States Patent
Baker et al.

(10) Patent No.: US 7,314,624 B2
(45) Date of Patent: Jan. 1, 2008

(54) NANOEMULSION VACCINES

(75) Inventors: James R. Baker, Ann Arbor, MI (US); Tarek Hamouda, Milan, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 76 days.

(21) Appl. No.: 10/162,970

(22) Filed: Jun. 5, 2002

(65) Prior Publication Data

US 2003/0194412 A1 Oct. 16, 2003

Related U.S. Application Data

(60) Provisional application No. 60/296,048, filed on Jun. 5, 2001.

(51) Int. Cl.
*A61K 39/12* (2006.01)
(52) U.S. Cl. .................................. 424/192.1
(58) Field of Classification Search ............. 424/222.1, 424/278.1, 279.1, 280.1, 282.1, 283.1; 536/115; 436/71; 514/546, 547–549, 937
See application file for complete search history.

(56) References Cited

U.S. PATENT DOCUMENTS

| | | | | |
|---|---|---|---|---|
| 4,481,188 | A * | 11/1984 | Apontoweil et al. | 424/222.1 |
| 4,895,454 | A | 1/1990 | Kammleiter et al. | 374/163 |
| 5,103,497 | A | 4/1992 | Hicks | 395/117 |
| 5,510,104 | A | 4/1996 | Allen | 424/94.4 |
| 5,547,677 | A | 8/1996 | Wright | 424/401 |
| 5,549,901 | A | 8/1996 | Wright | 424/401 |
| 5,618,840 | A | 4/1997 | Wright | 514/549 |
| 5,662,957 | A | 9/1997 | Wright | 426/605 |
| 5,700,679 | A | 12/1997 | Wright | 435/238 |
| 5,942,237 | A * | 8/1999 | Gizurarson et al. | 424/278.1 |
| 5,961,970 | A | 10/1999 | Lowell et al. | |
| 6,015,832 | A * | 1/2000 | Baker et al. | 514/546 |
| 6,350,784 | B1 * | 2/2002 | Squires | 514/642 |
| 6,506,803 | B1 * | 1/2003 | Baker et al. | 424/678 |
| 6,565,873 | B1 * | 5/2003 | Shefer et al. | 424/426 |
| 2002/0045667 | A1 | 4/2002 | Baker et al. | |

OTHER PUBLICATIONS

Fields. Fields Virology. Lippincott Williams & Wilkins Publishers; Aug. 2001, p. 1555.*
Cox et al. Influenza virus: immunity and vaccination strategies. Comparison of the immune response to inactivated and live, attenuated influenza vaccines. Scandinavian Journal of Immunology. vol. 59, p. 1-15.*
Paul. Fundamental Immunology. Lippincott Williams & Wilkins Publishers; 5th edition Sep. 2003, p. 1353.*
Tumpey et al. Mucosal delivery of inactivated influenza vaccine induces B-cell-dependent heterosubtypic cross-protection against lethal influenza A H5N1 virus infection. Journal of virology, Jun. 2001, vol. 75, No. 11, 5141-5150.*
Donovan et al. Prevention of murine influenza A virus pneumonitis by surfactant nano-emulsions. Antiviral Chemistry and Chemotherapy, 2000, vol. 11, pp. 41-49.*
Bielinska et al. Mucosal immunization with a novel nanoemulsion-based recombinant anthrax protective antigen vaccine protects against *Bacillus anthracis* spore challenge. Infection and Immunity. Aug. 2007, vol. 75, No. 8, 4020-4029.*
Richter and Kipp, Curr Top Microbiol Immunol 240:159-76 [1999].
Ruedl and Wolf, Int. Arch. Immunol., 108:334 [1995].
Mor et al., Trends Micrbiol 6:449-53 [1998].
McMichael, Curr. Top. Microbiol. Immunol. 189:75 [1994].
Sercarz et al., Anu Rev Immunol 11:729 [1993].
Perreault et al., Immunol Today 19:69 [1998].
Silins et al., J Exp Med 184:1815 [1996].
Steven et al., J Exp Med 184:1801 [1996].
Tremblay et al., Transplantation 58:59 [1994].
Russell, Clin. Micro. 3; 99 [1990].
Burdon and Wende, J Infect. Diseas. 170(2):224-34 [1960].
Lamanna and Jones, J. Bact. 85:532 [1963].
Burdon et al., J Infect. Diseas. 117:307 [1967].
Drobniewski, Clin. microbio. Rev. 6:324 [1993].
Fritz et al., Lab. Invest. 73:691 [1995].
Hamouda et al., J. Infect Dis., 180:1939 [1999].
Hamouda and Baker, J. Appl. Microbiol., 89:397 [2000].
Eriksson et al., Blood Coagulation and Fibtinolysis 5 (Suppl. 3):S37-S44 [1994].
Maha and Igarashi, Southeast Asian J. Trop. Med. Pub. Health 28:718 [1997].
Portocala et al., Virologie 27:261 [1976].
Horowitz et al., Blood 79:826 [1992].
Hills, J. Gen. Micro. 4:38 [1950].
Halvorson and Church, Bacteriol Rev. 21:112 [1957].
Yanagita, Arch Mikrobiol 26:329 [1957].
Brown et al., J. Bact., 75:499 [1958].
Stevens et al., Antimicrob. Agents Chemother., 31:312 [1987].
Stevens et al., J. Infect. Dis., 155:220 [1987].
Alttemeier et al., Surgery, 28:621 [1950].
Sandusky et al., Surgery, 28:632 [1950].
Butterton et al., Infect. Immun., 64:4373 [1996].
Levine et al., Microbiol. Rev., 47:510 [1983].
Finkelstein et al., J. Infect. Dis., 114:203 [1964].

(Continued)

*Primary Examiner*—Bruce Campell
*Assistant Examiner*—Emily M. Le
(74) *Attorney, Agent, or Firm*—Casimir Jones, S.C.

(57) ABSTRACT

The present invention provides methods and compositions for the stimulation of immune responses. Specifically, the present invention provides methods and compositions for the use of nanoemulsion compounds as mucosal adjuvants to induce immunity against environmental pathogens. Accordingly, in some embodiments, the present invention provides nanoemulsion vaccines comprising a nanoemulsion and an inactivated pathogen or protein derived from the pathogen. The present invention thus provides improved vaccines against a variety of environmental and human-released pathogens.

23 Claims, 39 Drawing Sheets

OTHER PUBLICATIONS

Freter, J. Exp. Med., 104:411 [1956].
Freter, J. Infect. Dis., 97:57 [1955].
Formal et al., J. Bact., 85:119 [1963].
LaBrec et al., J. Bact. 88:1503 [1964].
Takeuchi et al., Am. J. Pathol., 47:1011 [1965].
Naughton et al., J. Appl. Bact., 81:651 [1996].
Carter and Collins, J. Exp. Med., 139:1189 [1974].
Collins, Infect. Immun., 5:191 [1972].
Collins and Carter, Infect. Immun., 6:451 [1972].
Jacoby et al., Exp. Gerontol., 29:89 [1994].
Massion et al., Am. J. Respir. Cell Mol. Biol. 9:361 [1993].
Castleman et al., Am. J. Path., 129:277 [1987].
Castleman, Am. J. Vet. Res., 44:1024 [1983].
Mims and Murphy, Am. J. Path., 70:315 [1973].
Johnson et al., J. Infect. Dis., 125:257 [1972].
Johnson, Am. J. Path., 46:929 [1965].
Welkos et al., Infect Immun. 51:795 [1986].
Welkos and Friedlander, Microb Pathog 5:127 [1988].
Karaivanova and Spiro, Biochem J. 329(Pt 3):511 [1998].
Mammen et al., J Med Chem 38:4179 [1995].

* cited by examiner

FIGURE 3

| MICROBE | |
|---|---|
| Bacteria | *Bacillus* (including *B. cereus, B. anthracis, B. circulans B. subtilis,* and *B. megaterium*); |
| | *Clostridium* (including *C. botulinum, C. tetani,* and *C. perfringens*); |
| | *E. coli*; |
| | *Haemophilus* (including *H. influenzae*); |
| | *Listeria monocytogenes*; |
| | *Neisseria* (including *N. gonorrhoeae*); |
| | *Proteus* (including *P. mirabilis*); |
| | *Psuedomonas* (including *P. aeruginosa*); |
| | *Shigella* (including *S. dysenteriae*); |
| | *Salmonella* (including *S. typhimurium*); |
| | *Staphlococcus* (including *S. aureus*) |
| | *Streptococcus* (including *S. agalactiae, S. pneumonia, S. pyogenes*); |
| | *Vibrio* (including *V. cholerae* classical and Eltor); and |
| | *Yersinea* (including *Y. enterocolitica* and *Y. pseudotuberculosis*); and |
| Enveloped virus | Influenza (including A, B and C); |
| | Herpes (including H. simplex); |
| | Sendai; |
| | Sindbis; and |
| | Pox virus (including vaccinia) |
| Fungi | *Candida* (including *C. albicans* and *C. tropicalis*); |
| | *Trichophyton* (including *T. rubrum* and *T. mentagrophytes*); |
| | *Microsporum gypseum*; |
| | *Byssochlymus fulva* |

FIGURE 4

| Emulsion Formulas | | Result |
|---|---|---|
| ATB-X100 | | Effective against enveloped viruses, all Gram positive bacteria, all Gram negative bacteria and fungi |
| 8% | Triton X-100 | |
| 8% | Tributyl Phosphate | |
| 64% | Soybean Oil | |
| 1% | CPC | |
| 19% | DiH2O | |
| ATB-T60 | | Slightly less effective than ATB-X100; Effective against enveloped viruses, all Gram positive bacteria, all Gram negative bacteria and fungi |
| 5% | Tween 60 | |
| 8% | Tributyl Phosphate | |
| 64% | Soybean Oil | |
| 1% | CPC | |
| 22% | DiH2O | |
| ATB-XT160 | | Effective against enveloped viruses, all Gram positive bacteria, all Gram negative bacteria and fungi |
| 0.71% | Tween 60 | |
| 8% | Triton X-100 | |
| 8% | Tributyl Phosphate | |
| 64% | Soybean Oil | |
| 1% | CPC | |
| 18.29% | DiH2O | |
| ATB-X | | Effective against enveloped viruses, all Gram positive bacteria, all Gram negative bacteria and fungi; |
| 5% | Triton X-100 | |
| 5% | Tributyl Phosphate | |
| 40% | Soybean Oil | |
| 1% | CPC | |
| 49% | DiH2O | |

Figure 4 (Cont.)

| Formulation | % | Component | Effect |
|---|---|---|---|
| ATB-X1001 | | | Effective against enveloped viruses, all Gram positive bacteria, all Gram negative bacteria and fungi |
| | 8% | Triton X-100 | |
| | 8% | Tributyl Phosphate | |
| | 50% | Soybean Oil | |
| | 1% | CPC | |
| | 33% | DiH2O | |
| ATB-X1002 | | | Effective against enveloped viruses, all Gram positive bacteria, all Gram negative bacteria and fungi; more irritating than ATB-X100. |
| | 8% | Triton X-100 | |
| | 8% | Tributyl Phosphate | |
| | 50% | Soybean Oil | |
| | 2% | CPC | |
| | 32% | DiH2O | |
| ATB-2 | | | Effective against enveloped viruses, all Gram positive bacteria, all Gram negative bacteria and fungi |
| | 0.1% | Peppermint Oil | |
| | 8% | Triton X-100 | |
| | 8% | Tributyl Phosphate | |
| | 64% | Soybean Oil | |
| | 2% | CPC | |
| | 17.9% | DiH2O | |
| ATB-CPB | | | Effective against enveloped viruses, all Gram positive bacteria, all Gram negative bacteria |
| | 0.1% | Peppermint Oil | |
| | 8% | Triton X-100 | |
| | 8% | Tributyl Phosphate | |
| | 64% | Soybean Oil | |
| | 1% | CPB | |
| | 18.9% | DiH2O | |
| ATB-1/2 | | | Effective against enveloped viruses, all Gram positive bacteria, all Gram negative bacteria and fungi, demonstrates that dilution doesn't effective efficacy of ATB-X100 |
| | 0.05% | Peppermint Oil | |
| | 4% | Triton X-100 | |
| | 4% | Tributyl Phosphate | |
| | 32% | Soybean Oil | |
| | 0.5% | CPC | |
| | 59.45% | DiH2O | |

Figure 4 (Cont.)

| | | |
|---|---|---|
| ATB-T3 | | Effective against enveloped viruses, all Gram positive bacteria, all Gram negative bacteria and fungi |
| 3% | Tyloxapol | |
| 8% | Tributyl Phosphate | |
| 64% | Soybean Oil | |
| 1% | CPC | |
| 0.1% | Peppermint Oil | |
| 23.9% | DiH2O | |
| | | |
| ATB-T3E pH7.1 | | |
| 3% | Tyloxapol | Effective against, all Gram positive bacteria, all Gram negative bacteria and spores |
| 8% | Ethanol | |
| 64% | Soybean Oil | |
| 1% | CPC | |
| 0.1% | Peppermint Oil | |
| 23.8% | DiH2O | |
| 0.1% | 10N NaOH | |
| | | |
| ATB-T22 | | Effective against enveloped viruses, all Gram positive bacteria, all Gram negative bacteria and fungi; stable despite lower amount of detergent |
| 2% | Triton X-100 | |
| 2% | Tyloxapol | |
| 8% | Tributyl Phosphate | |
| 64% | Soybean Oil | |
| 1% | CPC | |
| 0.1% | Peppermint Oil | |
| 22.9% | DiH2O | |
| | | |
| ATB-1X | | Effective against enveloped viruses, all Gram positive bacteria, all Gram negative bacteria, and bacterial spores |
| 8% | Triton X-100 | |
| 8% | Tributyl Phosphate | |
| 64% | Soybean Oil | |
| 1% | CPC | |
| 0.1% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 18.9% | DiH2O | |

Figure 4 (Cont.)

| ATB-T22/GE | | Effective against enveloped viruses, all Gram positive bacteria, Gram negative bacteria, and bacterial spores |
|---|---|---|
| 2% | Triton X-100 | |
| 2% | Tyloxapol | |
| 8% | Tributyl Phosphate | |
| 64% | Soybean Oil | |
| 1% | CPC | |
| 0.1% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 22.9% | DiH2O | |

| 90% ATB-T22/GE | | Effective against enveloped viruses, Gram negative bacteria, all Gram positive bacteria, and bacterial spores; liquid enough to spray |
|---|---|---|
| 1.8% | Triton X-100 | |
| 1.8% | Tyloxapol | |
| 7.2% | Tributyl Phosphate | |
| 57.6% | Soybean Oil | |
| 0.9% | CPC | |
| 0.09% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 30.61% | DiH2O | |

| ATB-T22E | | Effective against enveloped viruses, all Gram positive bacteria, all Gram negative bacteria and fungi; Increased safety for oral uptake |
|---|---|---|
| 2% | Triton X-100 | |
| 2% | Tyloxapol | |
| 8% | Ethanol (200 Proof) | |
| 64% | Soybean Oil | |
| 1% | CPC | |
| 0.1% | Peppermint Oil | |
| 22.9% | DiH2O | |

Figure 4 (Cont.)

| 90% ATB-T22E/GE | | Effective against enveloped viruses, all Gram positive bacteria, all Gram negative bacteria and fungi; Increased safety for oral uptake |
|---|---|---|
| 1.8% | Triton X-100 | |
| 1.8% | Tyloxapol | |
| 7.2% | Ethanol (200 Proof) | |
| 57.6% | Soybean Oil | |
| 0.9% | CPC | |
| 0.09% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 30.61% | DiH2O | |
| ATB-T3E | | Effective against all Gram positive bacteria, all Gram negative bacteria; Increased safety for oral uptake |
| 3% | Tyloxapol | |
| 8% | Ethanol | |
| 64% | Soybean Oil | |
| 1% | CPC | |
| 0.1% | Peppermint Oil | |
| 23.9% | DiH2O | |
| ATB-X100E | | |
| 8% | Triton X-100 | |
| 8% | Ethanol | |
| 64% | Soybean Oil | |
| 1% | CPC | |
| 19% | DiH2O | |
| ATB_Tween 20 E | | Effective against all Gram negative bacteria. |
| 5% | Tween 20 | |
| 1% | CPC | |
| 64% | Soybean Oil | |
| 8% | Ethanol | |
| 22% | DiH2O | |

Figure 9A

Log reduction of E. coli by various emulsions
(Rotator, 15min in media)

| Emulsion | 10% | 1% | 0.10% |
|---|---|---|---|
| 50% X8PC | 5.67 | 2.09 | 0 |
| D2P | 0.17 | 0 | 0 |
| EC | 5.81 | 5.81 | 4.42 |
| GC10 | 6.02 | 6.02 | 6.02 |
| P$_5$C* | 5.49 | 5.49 | 2.39 |
| S$_{60}$8GL5 | 0 | 0 | 0 |
| S8GL1B1 | 0 | 0 | 0 |
| S8P | 0.2 | 0.18 | 0.067 |
| W$_{20}$10EA5* | 0 | 0 | 0 |
| W$_{20}$10ECH$_3$* | 0 | 0 | 0 |
| W$_{20}$10EQ$_{100X}$ | 0 | 0 | 0 |
| W$_{20}$10EQ$_{10X}$ | 0 | 0 | 0 |
| W$_{20}$5EC | 6.22 | 6.22 | 5.48 |
| W$_{60}$PC | 5.81 | 5.81 | 2.62 |
| W$_{80}$5EC | 6.13 | 6.13 | 3.97 |
| X2Y2C* | 5.64 | 5.64 | 2.37 |
| X2Y2EC | 5.61 | 5.61 | 5.61 |
| X2Y2P$_4$C | 5.93 | 5.93 | 4 |
| X2Y2PC | 5.67 | 5.67 | 5.67 |
| X4Y4E | 0 | 0 | 0 |
| X8E | 0 | 0 | 0 |
| X8P BC | 5.93 | 4.41 | 0 |
| X8P CPB | 5.59 | 5.59 | 2.8 |
| X8P CPB | 4.26 | 0.35 | 0 |
| X8P CTAB | 4.04 | 0.16 | 0 |
| X8P Tannic acid | 3.84 | 0 | 0 |
| X8PC | 5.59 | 5.59 | 1.79 |
| X8PC2 | 5.59 | 5.59 | 4.42 |
| X8W$_{60}$PC | 5.58 | 5.58 | 1.05 |
| Y3C | 5.48 | 5.48 | 3.54 |
| Y3E | 0.25 | 0.19 | 0.05 |
| Y3EC | 6.13 | 6.13 | 6.13 |
| Y3EVc5 | 0 | 0 | 0 |
| Y3PC | 5.31 | 5.31 | 5.31 |
| Y8EC | 5.81 | 5.81 | 4.62 |
| Y8EC S | 0.08 | 0.08 | 0.04 |

Figure 9B

Log reduction of B. globigii spores by various emulsions
(Rotator, 4 hours in germination enhnacers)

| Emulsion | 10% | 1% | 0.10% |
|---|---|---|---|
| 50% X8PC | 2.21 | 2.6 | 2.46 |
| D2P | 0.94 | 1.28 | 1.75 |
| S8P | 0.53 | 0.94 | 1.27 |
| W$_{80}$4Y4E | 1.01 | 1.09 | 1.5 |
| W$_{80}$4Y4EC | 1.84 | 2.46 | 2.62 |
| W$_{80}$5E | 0.73 | 1.12 | 1.94 |
| W$_{80}$5EC | 1.8 | 2.31 | 2.6 |
| X2E | 2.4 | 2.27 | 0.5 |
| X2E | 2.44 | 1.15 | 0.86 |
| X2Y2C | 2.63 | 2.37 | 4.22 |
| X2Y2E | 1.88 | 1.24 | 1.08 |
| X2Y2EC | 2.55 | 2.83 | 3.13 |
| X2Y2EC | 1.94 | 2.19 | 2.6 |
| X2Y2P$_4$C | 2.78 | 2.71 | 3.44 |
| X2Y2PC | 2.93 | 2.72 | 4.11 |
| X2Y2PC | 2.67 | 2.57 | 3.73 |
| X2Y2PC | 2.8 | 2.71 | 3.95 |
| X2Y6E | 2.2 | 1.73 | 0.97 |
| X3E | 2.49 | 2.23 | 1.14 |
| X4E | 2.43 | 2.38 | 2.44 |
| X4E | 2.49 | 2.25 | 0.95 |
| X4Y4E | 2.61 | 1.89 | 1.31 |
| X5E | 2.44 | 2.51 | 0.41 |
| X5P$_5$C | 2.39 | 2.42 | 2.62 |
| X6E | 2.44 | 2.64 | 0.92 |
| X6Y2E | 2.7 | 2.62 | 1.72 |
| X8E | 2.19 | 2.28 | 0.47 |
| X8E | 2.42 | 2.55 | 0.92 |
| X8E O | 1.26 | 1.32 | 0.96 |
| X8PC | 2.6 | 2.73 | 2.79 |
| X8PC2 | 2.41 | 2.47 | 2.72 |
| Y2PC* | 1.37 | 1.57 | 3.2 |
| Y3PC | 2.32 | 2.57 | 3.8 |
| Y3PC | 2.33 | 2.44 | 3.31 |
| Y8E | 0.17 | 0.3 | 0.59 |
| Y8E | 0.49 | 0.59 | 0.6 |
| Y8E O | 1.02 | 0.56 | 0.7 |
| Y8EC | 2.01 | 2.39 | 2.56 |
| Y8P | 0.89 | 0.57 | 0.64 |

Log reduction of INF A pfu/ml treated with nanoemulsion series as measured by plaque reduction assay (30 min incubation)

Figure 9C

Logs of Reduction

| Compound | 1:10 | 1:100 | 1:1000 | |
|---|---|---|---|---|
| X2Y2E | 0 | 0 | 0 | |
| X4Y4E | 0 | 0 | 0 | |
| X6Y2E | 0 | 0 | 0 | |
| X2Y6E | 1.93 | 0 | 0 | |
| S608GL5 | 0 | 0 | 0 | |
| Y8E | 0 | 0 | 0 | |
| Y3E | 0 | 0 | 0 | |
| Y8ES | 0 | 0 | 0 | S= sorbic acid |
| Y8 | 0 | 0 | 0 | |
| X2E | 2.08 | 1.38 | 0 | |
| X3E | 2.6 | 0 | 0 | |
| X4E | 3.16 | 1.61 | 0 | |
| X5E | 3.16 | 1.61 | 0 | |
| X6E | 3.42 | 3.42 | 3.42 | |
| X8E | 3.86 | 3.86 | 0 | |
| X8E (unpurified oil) | 3.86 | 3.21 | 0 | |
| X8G | 2.74 | 2.74 | 0 | |
| X8B | 3.82 | 2.36 | 0 | B= Benzyl Benzoate |
| X8EO | 3.86 | 3.42 | 0 | O= Olive oil |
| D2P | 3.97 | 3.97 | 0.97 | |
| D2G | 3.82 | 3.82 | 0.00 | |
| S3Y3G STS5 | 2.26 | 0 | 0.00 | S= SDS |
| S8GL1B1 | 3.82 | 3.82 | 0.74 | S= SDS |
| S8G | 4.1 | 4.1 | 0.00 | S= SDS |
| S8P | 3.97 | 3.97 | 2.71 | S= SDS |
| $W_{80}5E$ | 0 | 0 | 0 | |
| $W_{80}4Y4E$ | 0 | 0 | 0 | |
| $W_{80}8$ | 0 | 0 | 0 | |
| $W_{20}5E$ | 0 | 0 | 0 | |
| $W_{80}4Y4EC$ | 3 | 3 | 2 | |
| $W_{80}5EC$ | 3 | 3 | 3 | |
| $W_{20}5EC$ | 3 | 3 | 3.3 | |
| X2Y2EC | 3 | 3 | 2 | |
| X2Y2PC | 3 | 3 | 3 | |
| X8PC | 4.98 | 4.98 | 4.98 | |
| X8GC | 4.68 | 4.68 | 4.68 | |
| X8EC | 4.1 | 4.1 | 1.97 | |
| Y8EC | 3 | 3 | 2 | |
| Y3EC | 3 | 3 | 2 | |
| Y3EC | 3 | 3 | 2.12 | |
| Y3PC | 3 | 3 | 2.63 | |
| BC | 3 | 3 | 3 | |
| GC | 4.14 | 4.14 | 4.14 | |
| ATB-EDTA | 3 | 3 | 1.98 | |
| Y2X2SPC | 1.10 | 1.10 | 0 | |

Figure 10B

Incubation of influenza A virus Ann Arbor strain with nanoemulsion

Figure 11

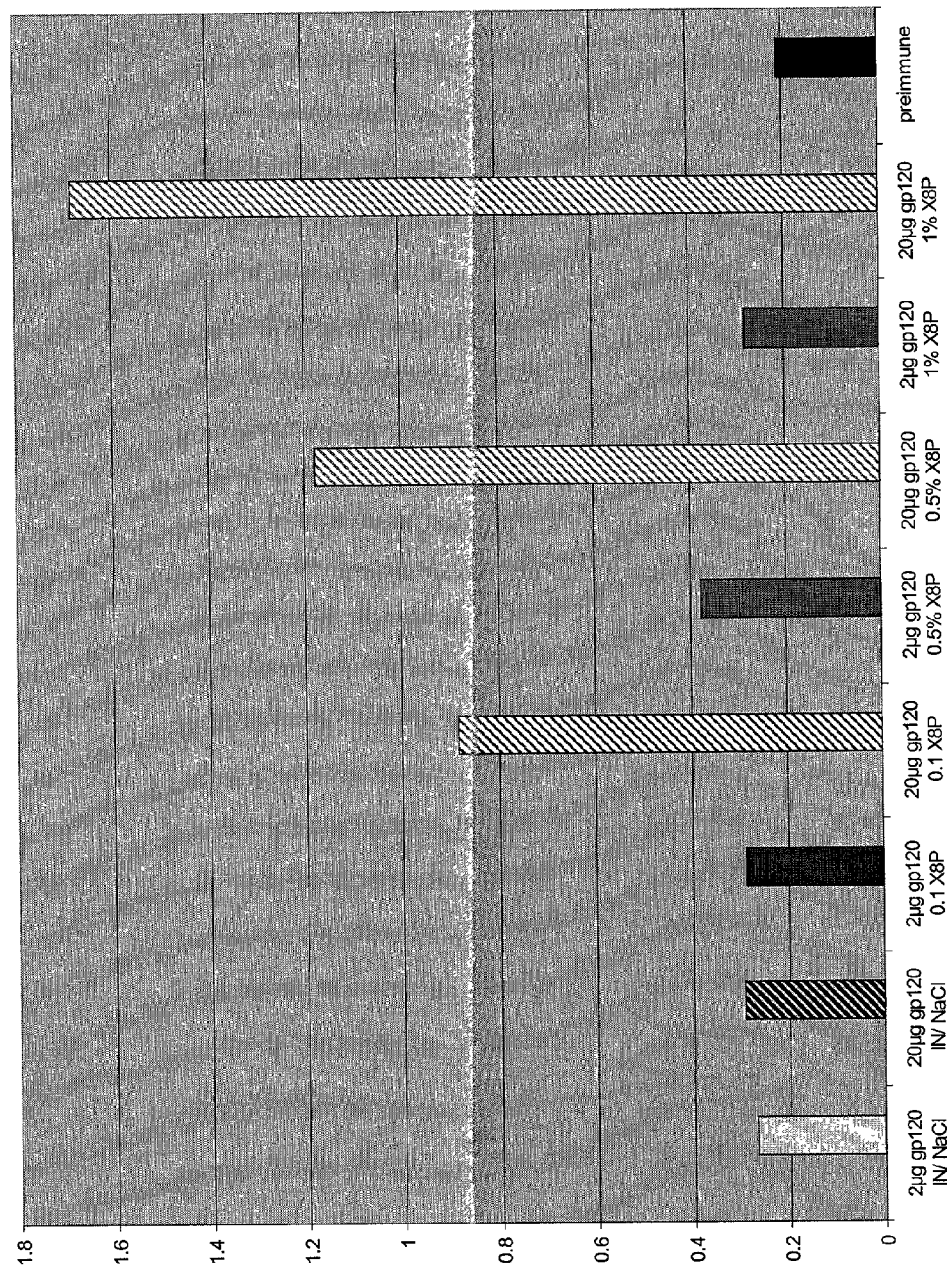

Immune Responses to Intra-muscular injected gp120

NANOEMULSION VACCINES

The application claims priority to provisional patent application Ser. No. 60/296,048, filed Jun. 5, 2001.

This work was supported by Defense Advanced Research Project Agency contract #MDA 972-007. The government has certain rights in this invention.

FIELD OF THE INVENTION

The present invention provides methods and compositions for the stimulation of immune responses. Specifically, the present invention provides methods and compositions for the use of nanoemulsion compounds as mucosal adjuvants to induce immunity against environmental pathogens.

BACKGROUND

Immunization is a principal feature for improving the health of people. Despite the availability of a variety of successful vaccines against many common illnesses, infectious diseases remain a leading cause of health problems and death. Significant problems inherent in existing vaccines include the need for repeated immunizations, and the ineffectiveness of the current vaccine delivery systems for a broad spectrum of diseases.

In order to develop vaccines against pathogens that have been recalcitrant to vaccine development, and/or to overcome the failings of commercially available vaccines due to expense, complexity, and underutilization, new methods of antigen presentation must be developed which will allow for fewer immunizations, more efficient usage, and/or fewer side effects to the vaccine.

SUMMARY OF THE INVENTION

The present invention provides methods and compositions for the stimulation of immune responses. Specifically, the present invention provides methods and compositions for the use of nanoemulsion compounds as mucosal adjuvants to induce immunity against environmental pathogens.

Accordingly, in some embodiments, the present invention provides a composition comprising a vaccine, the vaccine comprising an emulsion and an immunogen, the emulsion comprising an aqueous phase, an oil phase, and a solvent. In some embodiment, the immunogen comprises a pathogen (e.g., an inactivated pathogen). In other embodiments, the immunogen comprises a pathogen product (e.g., including, but not limited to, a protein, peptide, polypeptide, nucleic acid, polysaccharide, or a membrane component derived from the pathogen). In some embodiments, the immunogen and the emulsion are combined in a single vessel.

The present invention is not limited to a particular oil. A variety of oils are contemplated, including, but not limited to, soybean, avocado, squalene, olive, canola, corn, rapeseed, safflower, sunflower, fish, flavor, and water insoluble vitamins. The present invention is also not limited to a particular solvent. A variety of solvents are contemplated including, but not limited to, an alcohol (e.g., including, but not limited to, methanol, ethanol, propanol, and octanol), glycerol, polyethylene glycol, and an organic phosphate based solvent.

In some embodiments, the emulsion further comprises a surfactant. The present invention is not limited to a particular surfactant. A variety of surfactants are contemplated including, but not limited to, nonionic and ionic surfactants (e.g., TRITON X-100; TWEEN 20; and TYLOXAPOL).

In certain embodiments, the emulsion further comprises a cationic halogen containing compound. The present invention is not limited to a particular cationic halogen containing compound. A variety of cationic halogen containing compounds are contemplated including, but not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides. The present invention is also not limited to a particular halide. A variety of halides are contemplated including, but not limited to, halide selected from the group consisting of chloride, fluoride, bromide, and iodide.

In still further embodiments, the emulsion further comprises a quaternary ammonium containing compound. The present invention is not limited to a particular quaternary ammonium containing compound. A variety of quaternary ammonium containing compounds are contemplated including, but not limited to, Alkyl dimethyl benzyl ammonium chloride, dialkyl dimethyl ammonium chloride, n-Alkyl dimethyl benzyl ammonium chloride, n-Alkyl dimethyl ethylbenzyl ammonium chloride, Dialkyl dimethyl ammonium chloride, and n-Alkyl dimethyl benzyl ammonium chloride.

In certain embodiments, the immunogen is selected from the group consisting of virus, bacteria, fungus and pathogen products derived from the virus, bacteria, or fungus. The present invention is not limited to a particular virus. A variety of viral immunogens are contemplated including, but not limited to, influenza A, herpes simplex virus I, herpes simplex virus II, sendai, sindbis, vaccinia, parvo, human immunodeficiency virus, hepatitis B, virus hepatitis C virus, hepatitis A virus, cytomegalovirus, and human papilloma virus, picornavirus, hantavirus, junin virus, and ebola virus. The present invention is not limited to a particular bacteria. A variety of bacterial immunogens are contemplated including, but not limited to, *Bacillus cereus, Bacillus circulans* and *Bacillus megaterium, Bacillus anthracis, Clostridium perfringens, Vibrio cholerae, Streptococcus pyogenes, Streptococcus agalactiae, Streptococcus pneumonia, Staphylococcus aureus, Neisseria gonorrhoeae, Haemophilus influenzae, Escherichia coli, Salmonella typhimurium, Shigella dysenteriae, Proteus mirabilis, Pseudomonas aeruginosa, Yersinia enterocolitica,* and *Yersinia pseudotuberculosis*. The present invention is also not limited to a particular fungus. A variety of fungal immunogens are contemplated including, but not limited to, *Candida* and *Aspergillus*.

The present invention further provides a kit comprising a vaccine, the vaccine comprising an emulsion and an immunogen, the emulsion comprising an aqueous phase, an oil phase, and a solvent In some embodiments, the kit further comprises instructions for using the kit for vaccinating a subject against the immunogen.

In some embodiment, the immunogen comprises a pathogen (e.g., an inactivated pathogen). In other embodiments, the immunogen comprises a pathogen product (e.g., including, but not limited to, a protein, peptide, polypeptide, nucleic acid, polysaccharide, or membrane component derived from the pathogen). In some embodiments, the immunogen and the emulsion are combined in a single vessel.

The present invention is not limited to a particular oil. A variety of oils are contemplated, including, but not limited to, soybean, avocado, squalene, olive, canola, corn, rapeseed, safflower, sunflower, fish, flavor, and water insoluble vitamins. The present invention is also not limited to a particular solvent. A variety of solvents are contemplated including, but not limited to, an alcohol (e.g., including, but not limited to, methanol, ethanol, propanol, and octanol), glycerol, polyethylene glycol, and an organic phosphate based solvent.

In some embodiments, the emulsion further comprises a surfactant. The present invention is not limited to a particular surfactant. A variety of surfactants are contemplated including, but not limited to, nonionic and ionic surfactants (e.g., TRITON X-100; TWEEN 20; and TYLOXAPOL).

In certain embodiments, the emulsion further comprises a cationic halogen containing compound. The present invention is not limited to a particular cationic halogen containing compound. A variety of cationic halogen containing compounds are contemplated including, but not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides. The present invention is also not limited to a particular halide. A variety of halides are contemplated including, but not limited to, halide selected from the group consisting of chloride, fluoride, bromide, and iodide.

In still further embodiments, the emulsion further comprises a quaternary ammonium containing compound. The present invention is not limited to a particular quaternary ammonium containing compound. A variety of quaternary ammonium containing compounds are contemplated including, but not limited to, Alkyl dimethyl benzyl ammonium chloride, dialkyl dimethyl ammonium chloride, n-Alkyl dimethyl benzyl ammonium chloride, n-Alkyl dimethyl ethylbenzyl ammonium chloride, Dialkyl dimethyl ammonium chloride, and n-Alkyl dimethyl benzyl ammonium chloride.

In certain embodiments, the immunogen is selected from the group consisting of virus, bacteria, fungus and pathogen products derived from the virus, bacteria, or fungus. The present invention is not limited to a particular virus. A variety of viral immunogens are contemplated including, but not limited to, influenza A, herpes simplex virus I, herpes simplex virus II, sendai, sindbis, vaccinia, parvo, human immunodeficiency virus, hepatitis B, virus hepatitis C virus, hepatitis A virus, cytomegalovirus, and human papilloma virus, picornavirus, hantavirus, junin virus, and ebola virus. The present invention is not limited to a particular bacteria. A variety of bacterial immunogens are contemplated including, but not limited to, *Bacillus cereus, Bacillus circulans* and *Bacillus megaterium, Bacillus anthracis, Clostridium perfringens, Vibrio cholerae, Streptococcus pyogenes, Streptococcus agalactiae, Streptococcus pneumoniae, Staphylococcus aureus, Neisseria gonorrhoeae, Haemophilus influenzae, Escherichia coli, Salmonella typhimurium, Shigella dysenteriae, Proteus mirabilis, Pseudomonas aeruginosa, Yersinia enterocolitica*, and *Yersinia pseudotuberculosis*. The present invention is also not limited to a particular fungus. A variety of fungal immunogens are contemplated including, but not limited to, *Candida* and *Aspergillus.*

In still further embodiments, the present invention provides a method of inducing immunity to an immunogen, comprising providing an emulsion comprising an aqueous phase, an oil phase, and a solvent; and an immunogen; combining the emulsion with the immunogen to generate a vaccine composition; and administering the vaccine composition to a subject. In some embodiments, administering comprises contacting the vaccine composition with a mucosal surface of the subject. For example, in some embodiments, administering comprises intranasal administration. In some preferred embodiments, the administering in under conditions such that the subject is immune to the immunogen.

In some embodiment, the immunogen comprises a pathogen (e.g., an inactivated pathogen). In other embodiments, the immunogen comprises a pathogen product (e.g., including, but not limited to, a protein, peptide, polypeptide, nucleic acid, polysaccharide, or membrane component derived from the pathogen). In some embodiments, the immunogen and the emulsion are combined in a single vessel.

The present invention is not limited to a particular oil. A variety of oils are contemplated, including, but not limited to, soybean, avocado, squalene, olive, canola, corn, rapeseed, safflower, sunflower, fish, flavor, and water insoluble vitamins. The present invention is also not limited to a particular solvent. A variety of solvents are contemplated including, but not limited to, an alcohol (e.g., including, but not limited to, methanol, ethanol, propanol, and octanol), glycerol, polyethylene glycol, and an organic phosphate based solvent.

In some embodiments, the emulsion further comprises a surfactant. The present invention is not limited to a particular surfactant. A variety of surfactants are contemplated including, but not limited to, nonionic and ionic surfactants (e.g., TRITON X-100; TWEEN 20; and TYLOXAPOL).

In certain embodiments, the emulsion further comprises a cationic halogen containing compound. The present invention is not limited to a particular cationic halogen containing compound. A variety of cationic halogen containing compounds are contemplated including, but not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides. The present invention is also not limited to a particular halide. A variety of halides are contemplated including, but not limited to, halide selected from the group consisting of chloride, fluoride, bromide, and iodide.

In still further embodiments, the emulsion further comprises a quaternary ammonium containing compound. The present invention is not limited to a particular quaternary ammonium containing compound. A variety of quaternary ammonium containing compounds are contemplated including, but not limited to, Alkyl dimethyl benzyl ammonium chloride, dialkyl dimethyl ammonium chloride, n-Alkyl dimethyl benzyl ammonium chloride, n-Alkyl dimethyl ethylbenzyl ammonium chloride, Dialkyl dimethyl ammonium chloride, and n-Alkyl dimethyl benzyl ammonium chloride.

In certain embodiments, the immunogen is selected from the group consisting of virus, bacteria, fungus and pathogen products derived from the virus, bacteria, or fungus. The present invention is not limited to a particular virus. A variety of viral immunogens are contemplated including, but not limited to, influenza A, herpes simplex virus I, herpes simplex virus II, sendai, sindbis, vaccinia, parvo, human immunodeficiency virus, hepatitis B, virus hepatitis C virus, hepatitis A virus, cytomegalovirus, and human papilloma virus, picornavirus, hantavirus, junin virus, end ebola virus. The present invention is not limited to a particular bacteria. A variety of bacterial immunogens are contemplated including, but not limited to, *Bacillus cereus, Bacillus circulans* and *Bacillus megaterium, Bacillus anthracis, Clostridium perfringens, Vibrio cholerae, Streptococcus pyogenes, Streptococcus agalactiae, Streptococcus pneumonia, Staphylococcus aureus. Neisseria gonorrhoeae, Haemophilus* influenzae, Escherichia coli, Salmonella typhimurium, Shigella dysenteriae, Proteus mirabilis, Pseudomonas aeruginosa, Yersinia enterocolitica, and Yersinia pseudotuberculosis. The present invention is also not limited to a particular fungus. A variety of fungal immunogens are contemplated including, but not limited to, Candida and Aspergillus.

DESCRIPTION OF THE FIGURES

The following figures form part of the present specification and are included to further demonstrate certain aspects and embodiments of the present invention. The invention may be better understood by reference to one or more of these figures in combination with the description of specific embodiments presented herein.

FIG. 1 illustrates the antibacterial properties of 1% and 10% X8P. The bactericidal effect (% killing) was calculated as:

$$\frac{cfu(\text{initial}) - cfu(\text{post-treatment}) \times 100}{cfu(\text{initial})}$$

Figure 2:
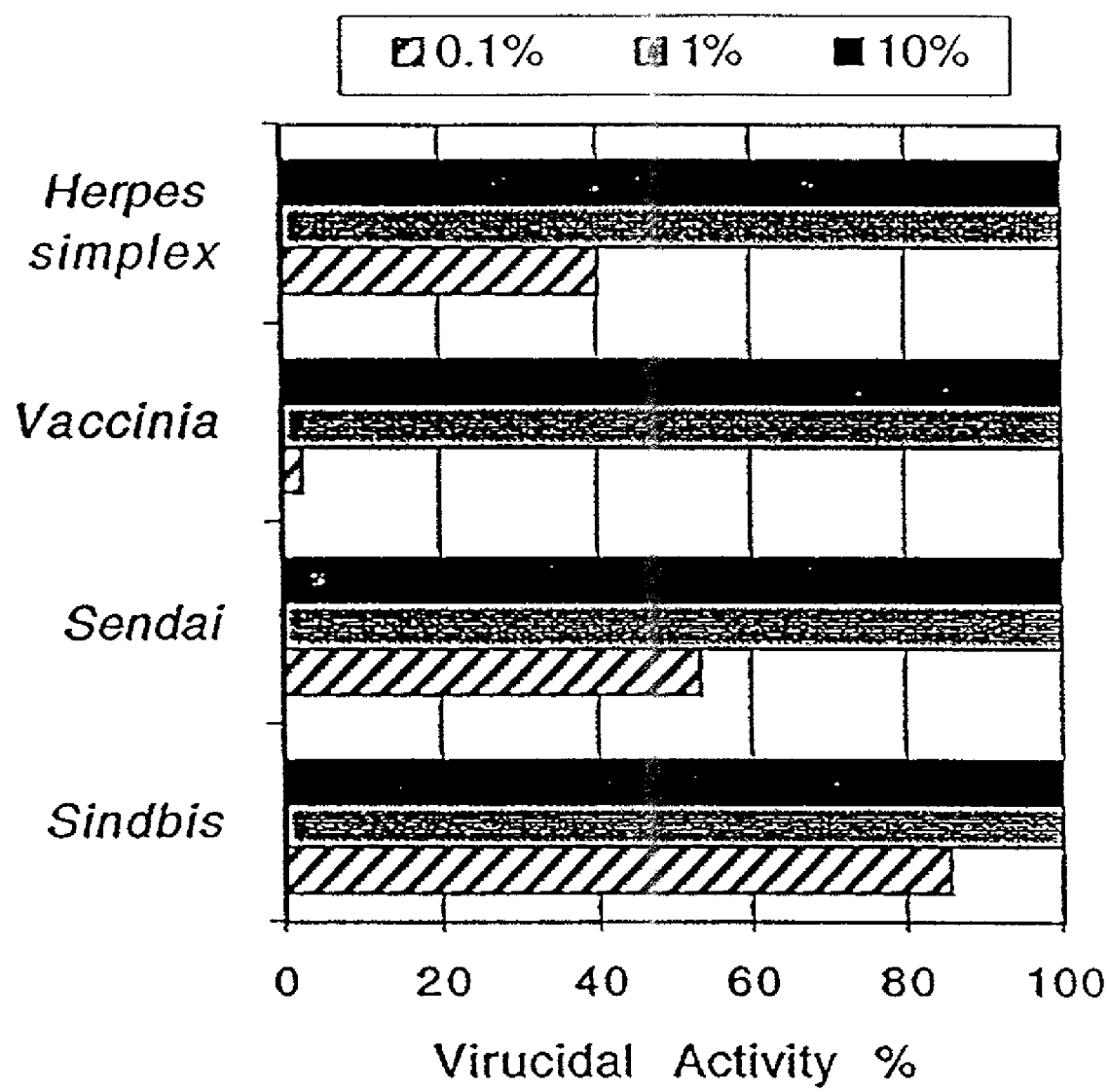

FIG. 2 illustrates the antiviral properties of 10% and 1% X8P as assessed by plaque reduction assays.

FIG. 3 illustrates several particular embodiments of the various pathogens of the present invention.

FIG. 4 illustrates several particular embodiments of the various emulsion compositions of the invention.

Figure 5:
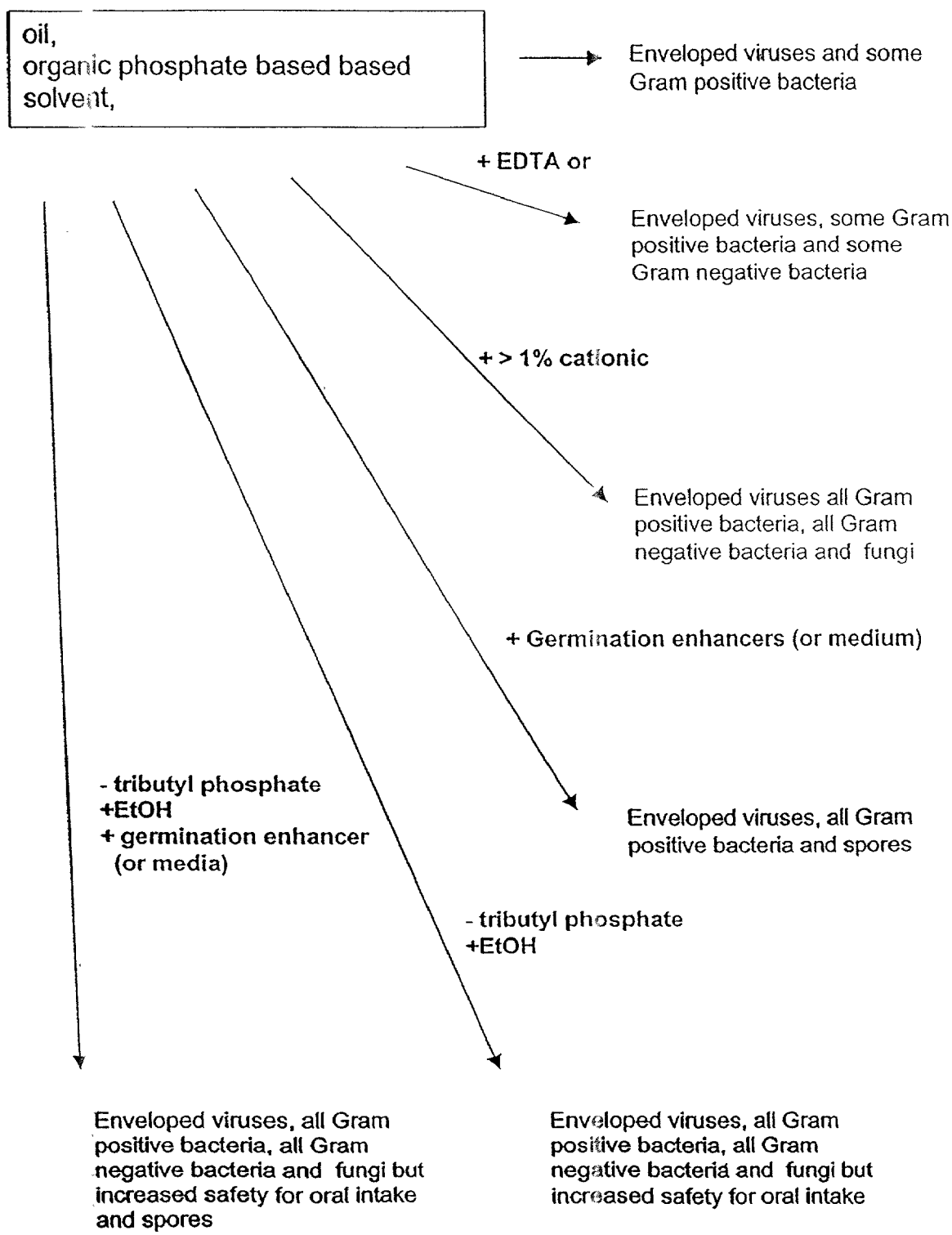

FIG. 5 schematically depicts various generalized formulations and uses of certain embodiments of the present invention.

Figure 6:
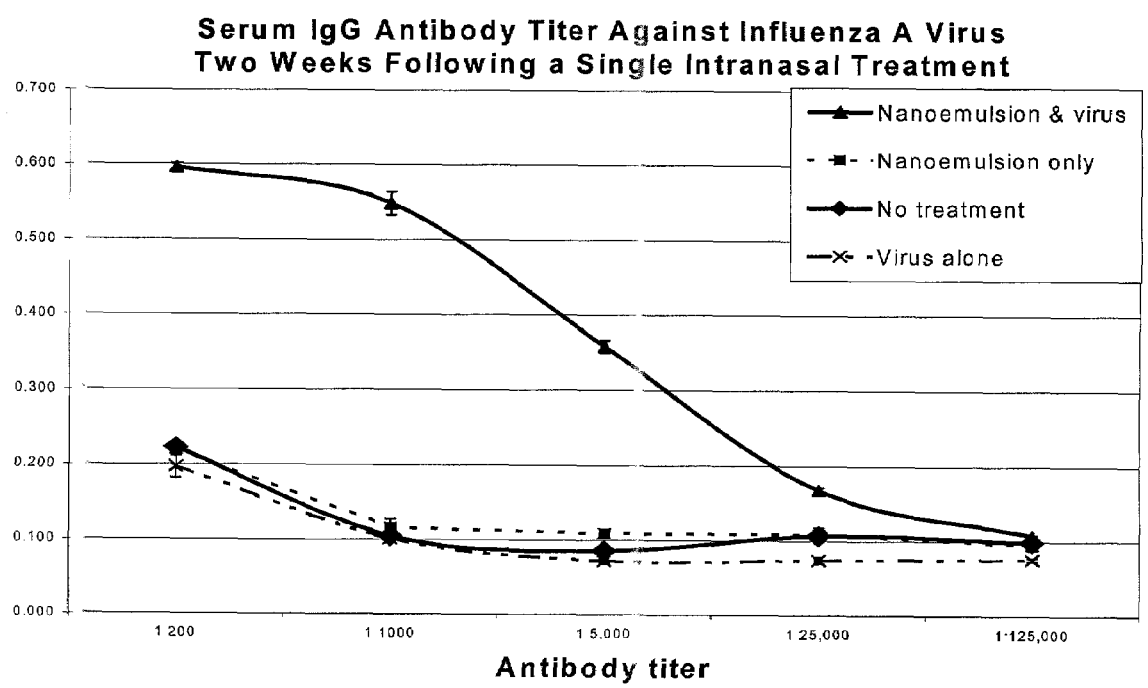

FIG. 6 shows serum IgG titers two weeks after a single intranasal treatment with certain exemplary nanoemulsion vaccines of the present invention.

Figure 7:
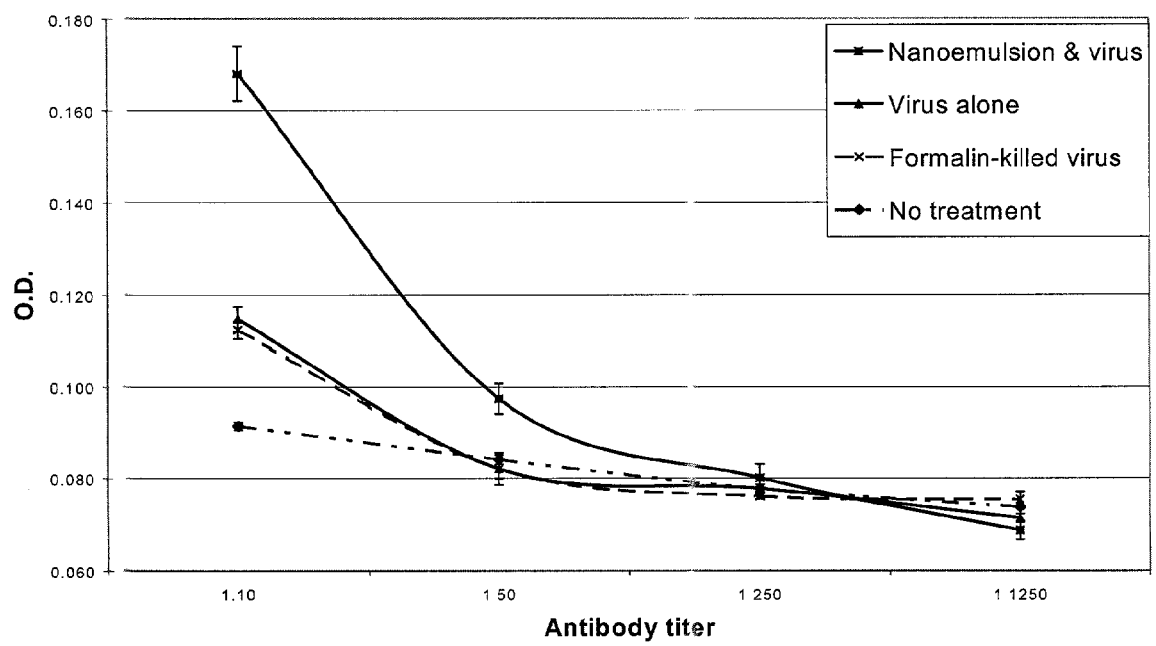

FIG. 7 shows bronchial IgA influenza titers in mice administered two intranasal doses of certain exemplary nanoemulsion vaccines of the present invention.

Figure 8:
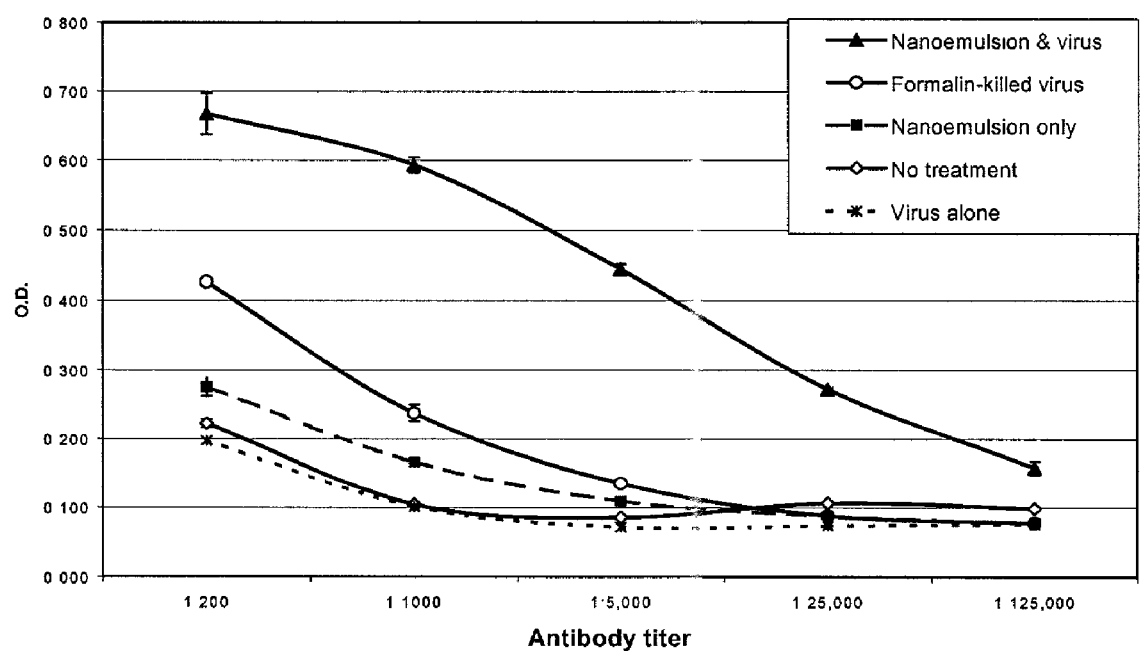

FIG. 8 shows serum IgG influenza titers in mice administered two intranasal doses of certain exemplary nanoemulsion vaccines of the present invention.

FIG. 9 shows the log reduction of pathogens by nanoemulsions of the present invention. FIG. 9A shows the log reduction of E. coli by various emulsions. FIG. 9B shows the log reduction of B. globigii by various emulsions. FIG. 9C shows the log reduction of influenza A by various emulsions.

Figure 10A:
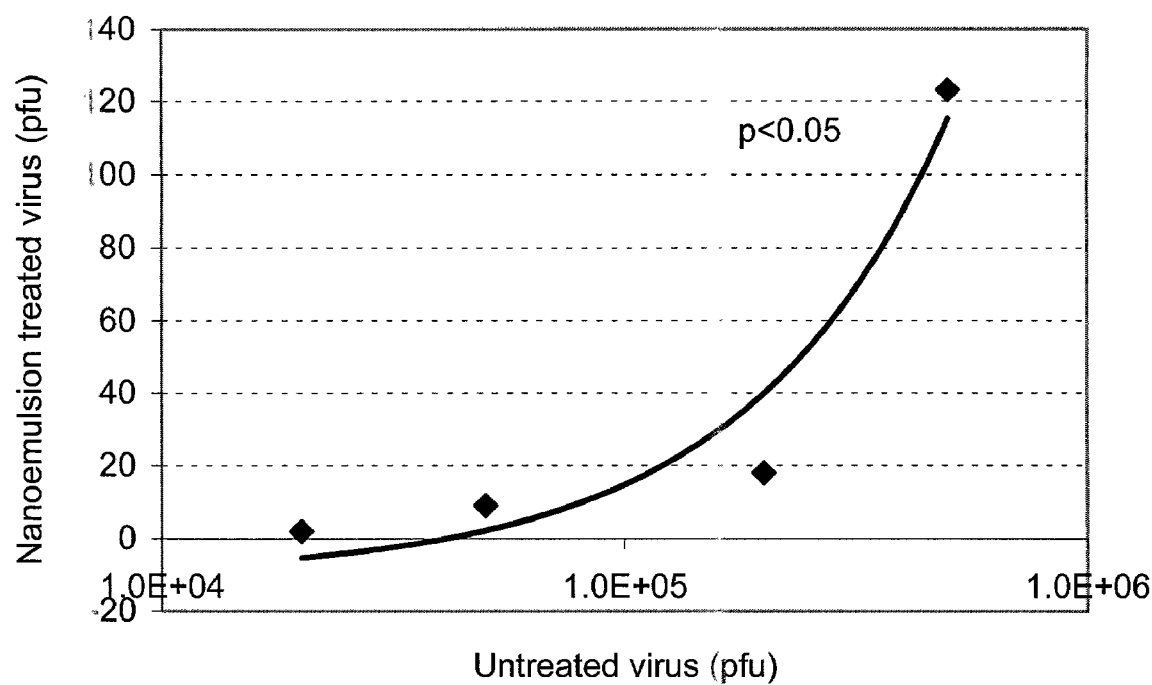
Figure 10C:
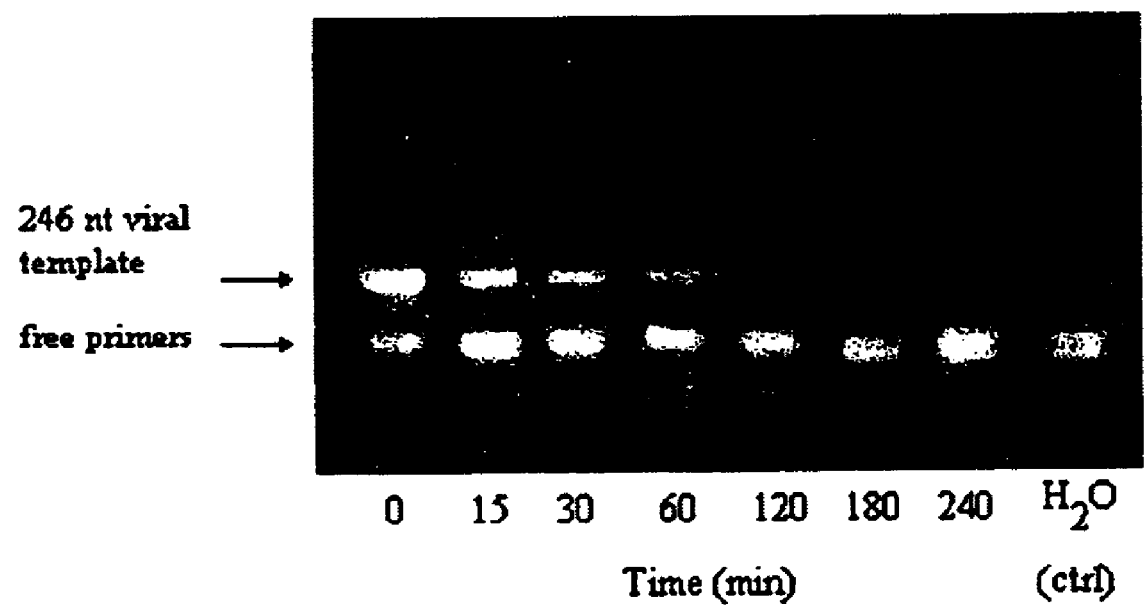

FIG. 10a shows the virucidal activity of 2% nanoemulsion on different concentrations of influenza A/AA virus. FIG. 10b shows the time dependent virucidal activity of nanoemulsions during incubation with influenza A/AA strain. FIG. 10c shows the detection of viral RNA template during incubation of virus with nanoemulsion. Compared with plaque reduction assay (FIG. 10b) RT-PCR of viral RNA from virus/nanoemulsion formulation showed full correlation in a time-dependant manner. Viral RNA was still present at 2 h, and was not detectable after 3 h of incubation.

Figure 11:
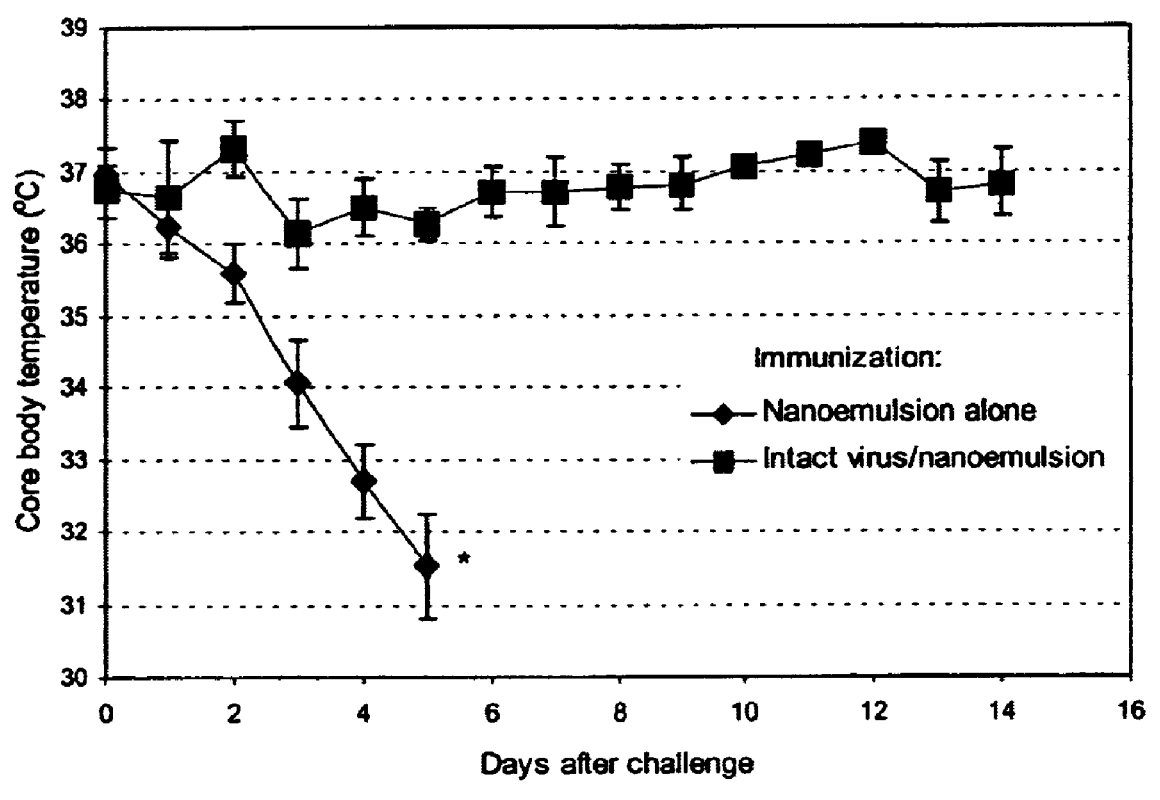

FIG. 11 shows the core body temperature of animals vaccinated with different vaccines and 20 days later challenged with lethal dose of influenza A Ann Arbor strain virus. *–N=3; two animals died before day 5.

Figure 12:
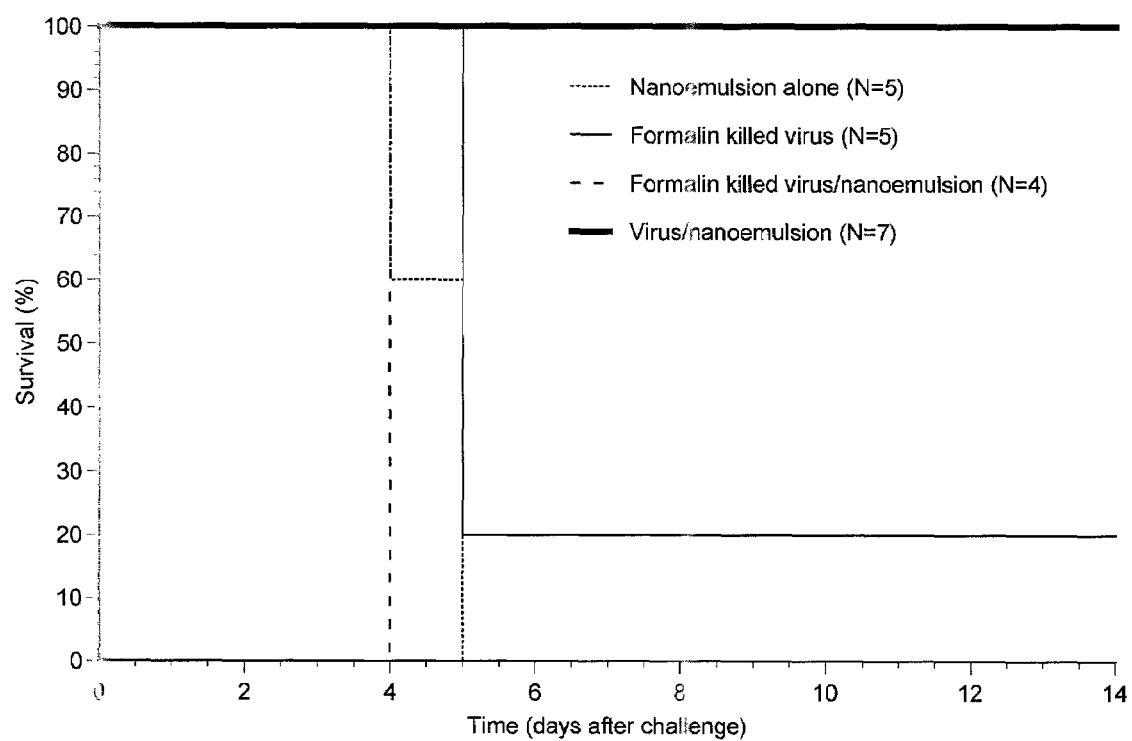

FIG. 12 shows survival curves of animals treated with different vaccines intranasally and challenged with lethal dose of influenza A Ann Arbor strain virus.

Figure 13:
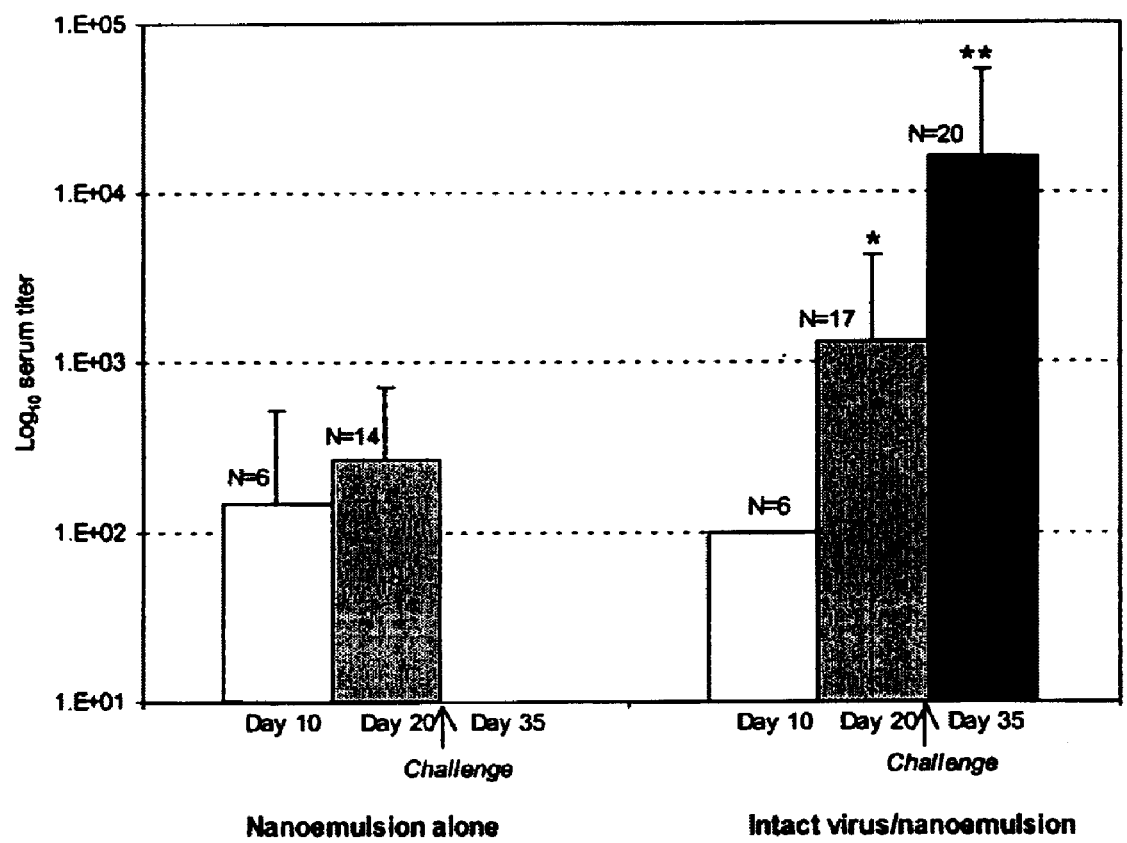

FIG. 13 shows that intranasal treatment of animals with virus/nanoemulsion mixture induced high levels of anti-influenza A, Ann Arbor strain IgG antibodies in serum. *–p<0.05 (nanoemulsion alone vs. virus/nanoemulsion, day 20); **–p<0.01 (virus/nanoemulsion, day 20 vs. day 35).

Figure 14:
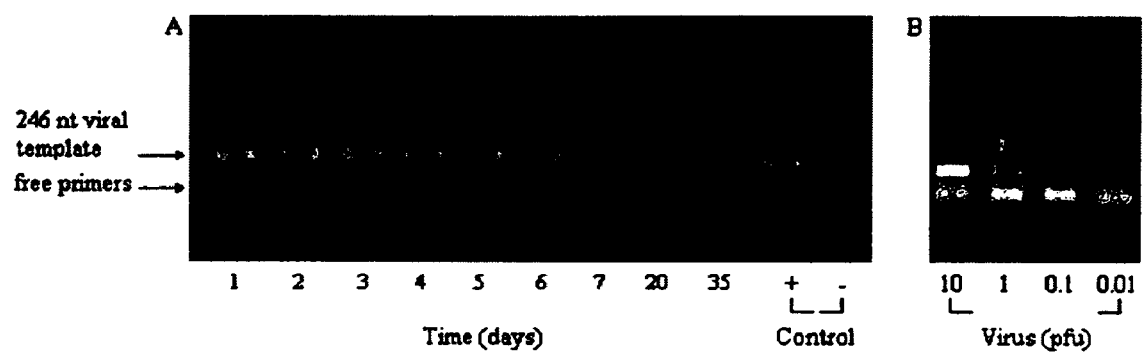

FIG. 14 shows the detection of influenza A virus RNA in virus/emulsion vaccinated animals RT-PCR showed the presence of viral template until day 6 after treatment which was not detectable on day 7 and thereafter (FIG. 14a). Signal generated from total lung RNA during the first 6 days after treatment was equal to 1 and not greater than 10 pfu of virus (FIG. 14b).

FIG. 15 shows early cytokine responses in splenocytes and serum of mice 72 hours after treatment with influenza A 100 pfu/mouse, formalin-killed virus $5 \times 10^5$ pfu, virus ($5 \times 10^5$ pfu)/2% nanoemulsion mixture, nanoemulsion alone. FIG. 15a shows IFN-γ levels. FIG. 15b shows TNF-α levels. FIG. 15c shows IL-12 p40 levels. FIG. 15d shows IL-4 levels. FIG. 15e shows IL-2 levels. FIG. 15f shows IL-10 levels. FIG. 15g shows IFN-γ levels on day 20 after treatment.

Figure 16:
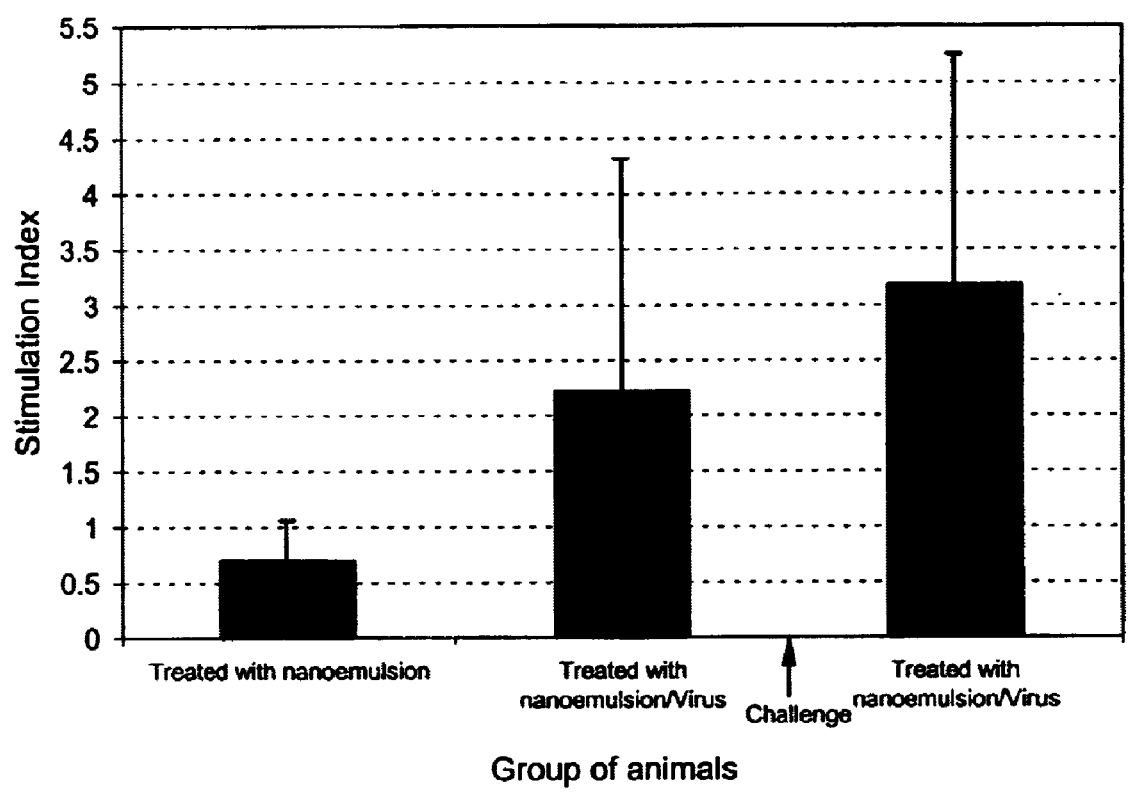

FIG. 16 shows stimulation indices of splenocytes harvested on day 20 and 35 of experiment from mice treated with virus/nanoemulsion.

Figure 17A:
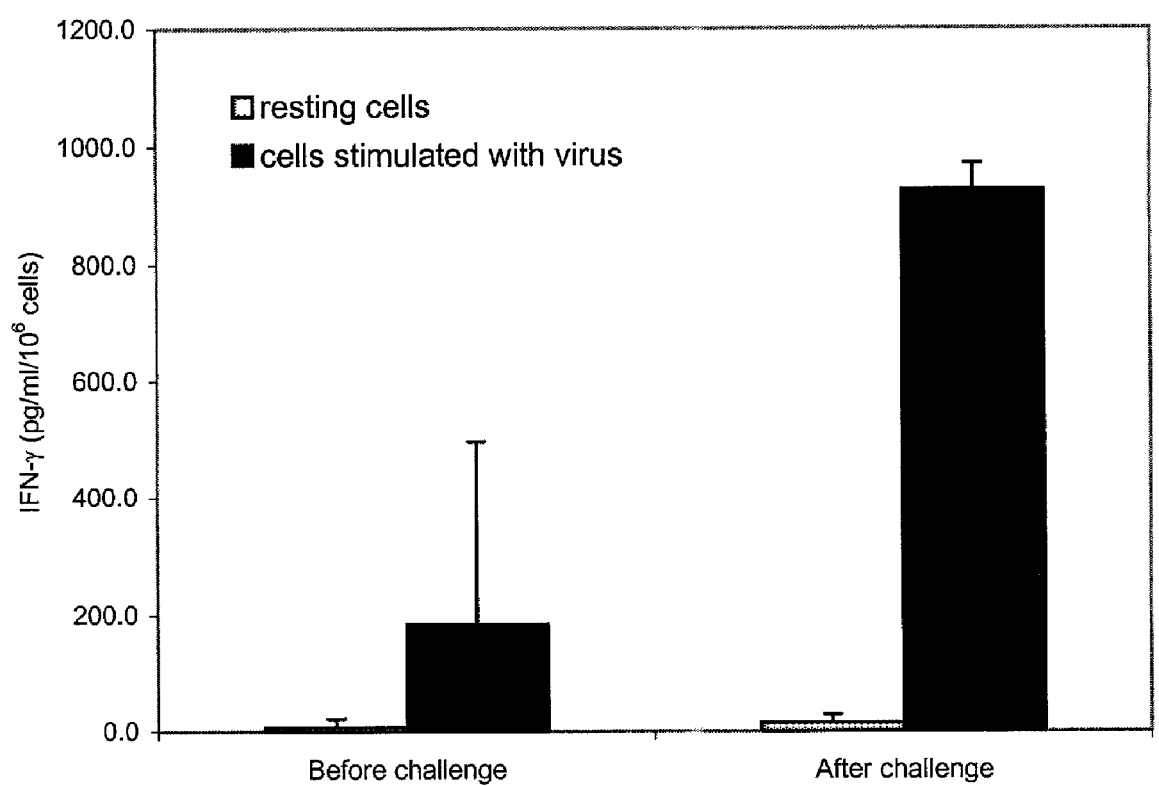
Figure 17B:
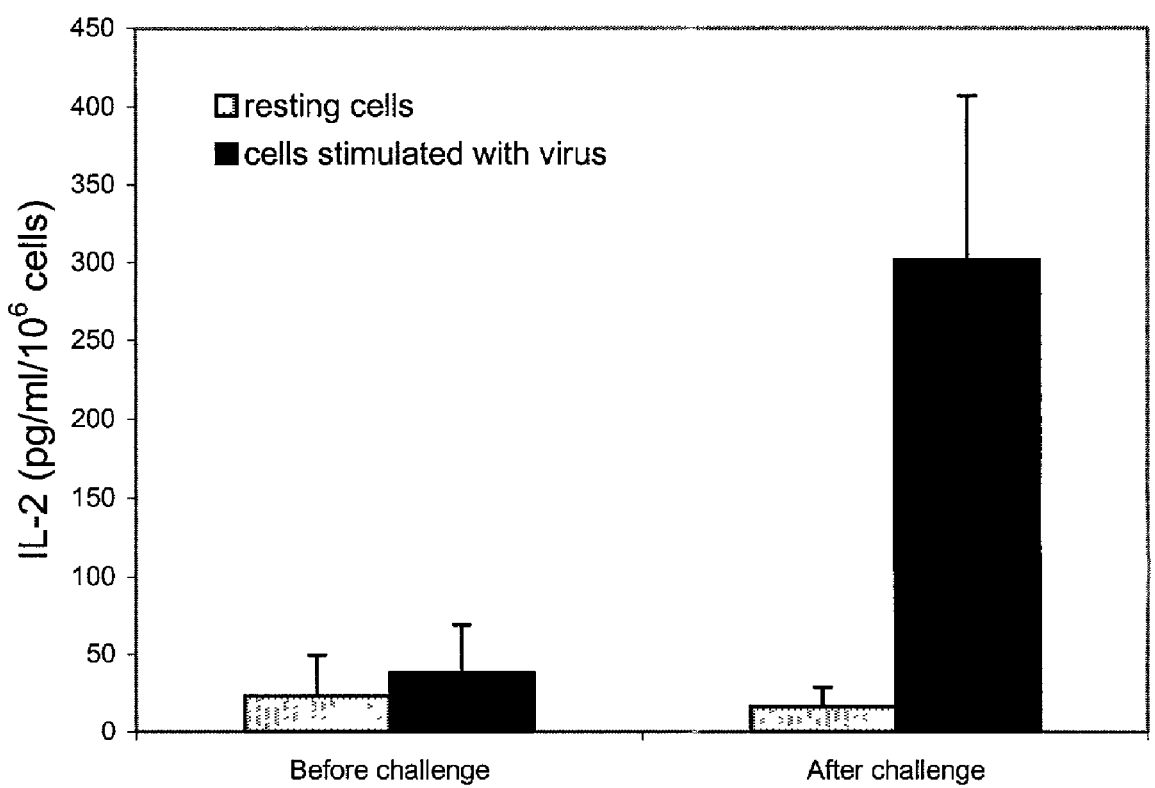
Figure 17C:
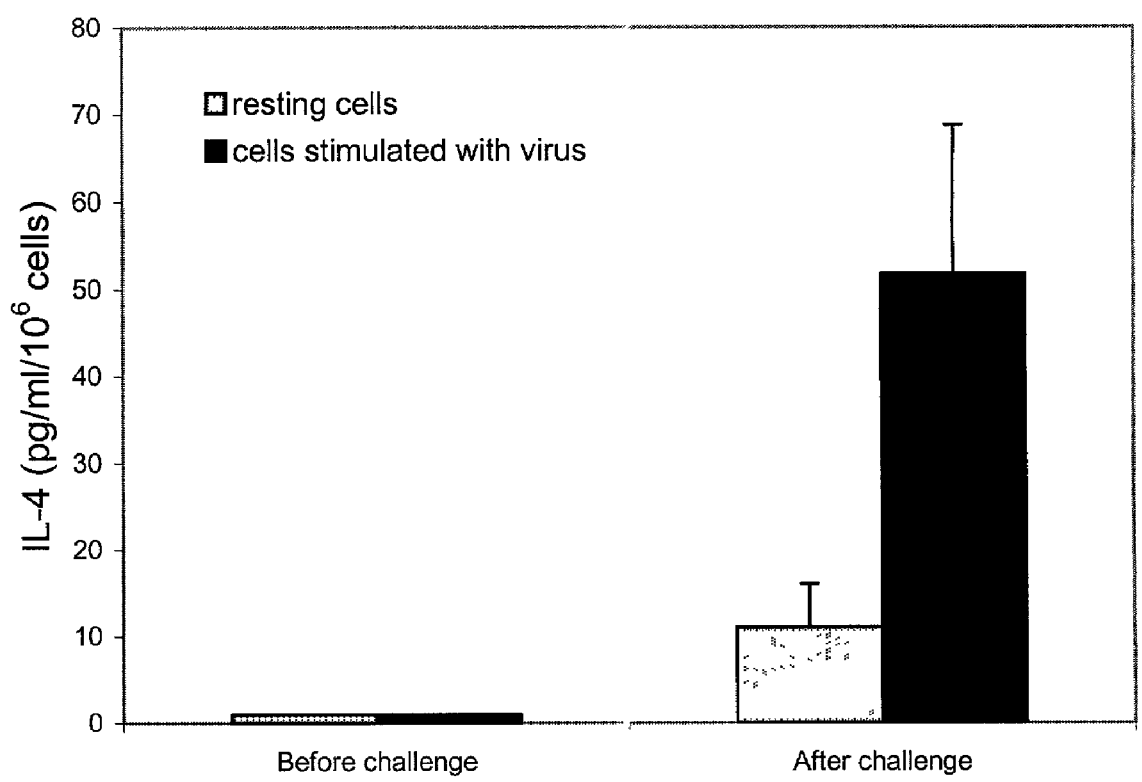

FIG. 17 shows antigen-specific activation of cytokine production by splenocytes harvested from mice after treatment with virus/nanoemulsion preparation. Splenocytes were harvested from animals on two occasions: on day 20 (before challenge) and day 35 (after challenge) of experiment. FIG. 17a shows IFN-γ levels. FIG. 17b shows IK-2 levels. FIG. 17c shows IL-4 levels.

Figure 18:
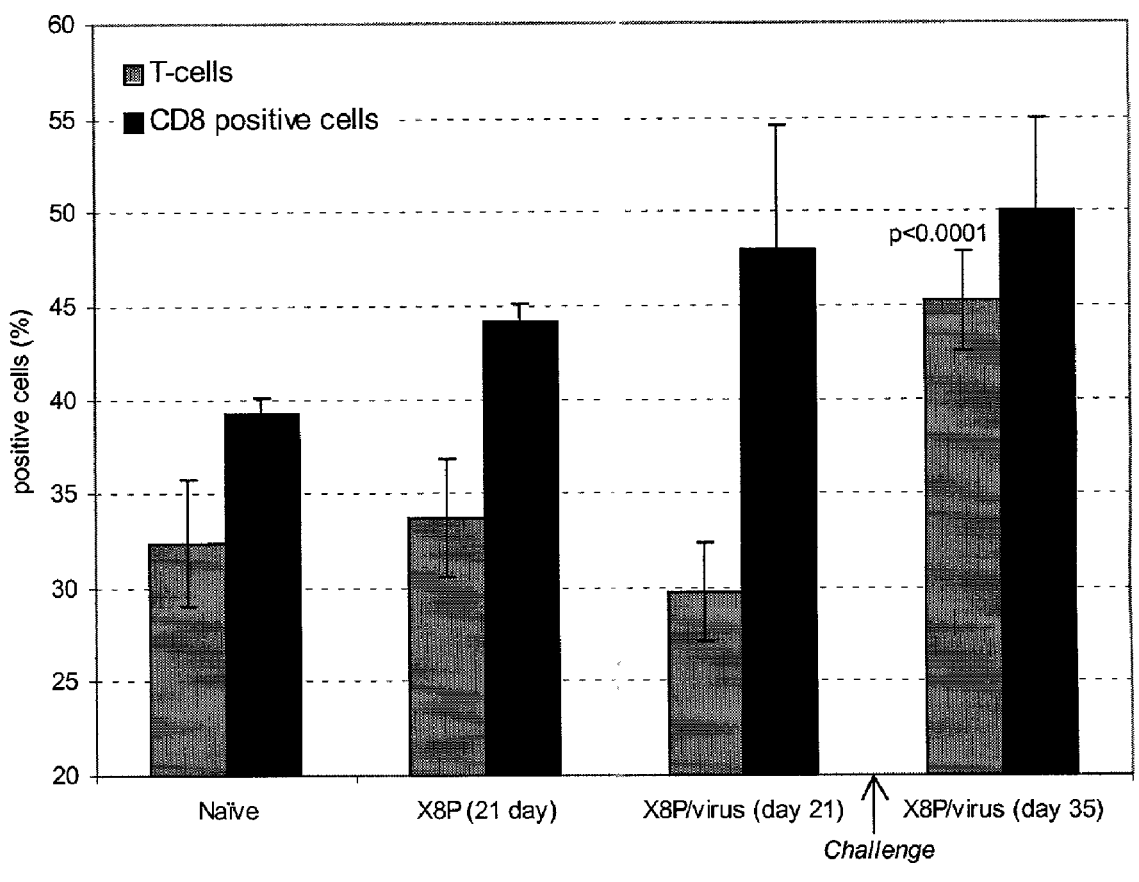

FIG. 18 shows the percentage of T (CD3 positive cells) and cytotoxic cells (CD8 positive cells) in splenocytes. Percentage was calculated as follows: T-cells (%)=(CD3 cells/(CD3+CD19 cells))*100; CD8 cells (%)=(CD8 cells/(CD8+CD4 cells))*100. p-value described the significance between the percentage of T-cells before and after the challenge.

Figure 19:
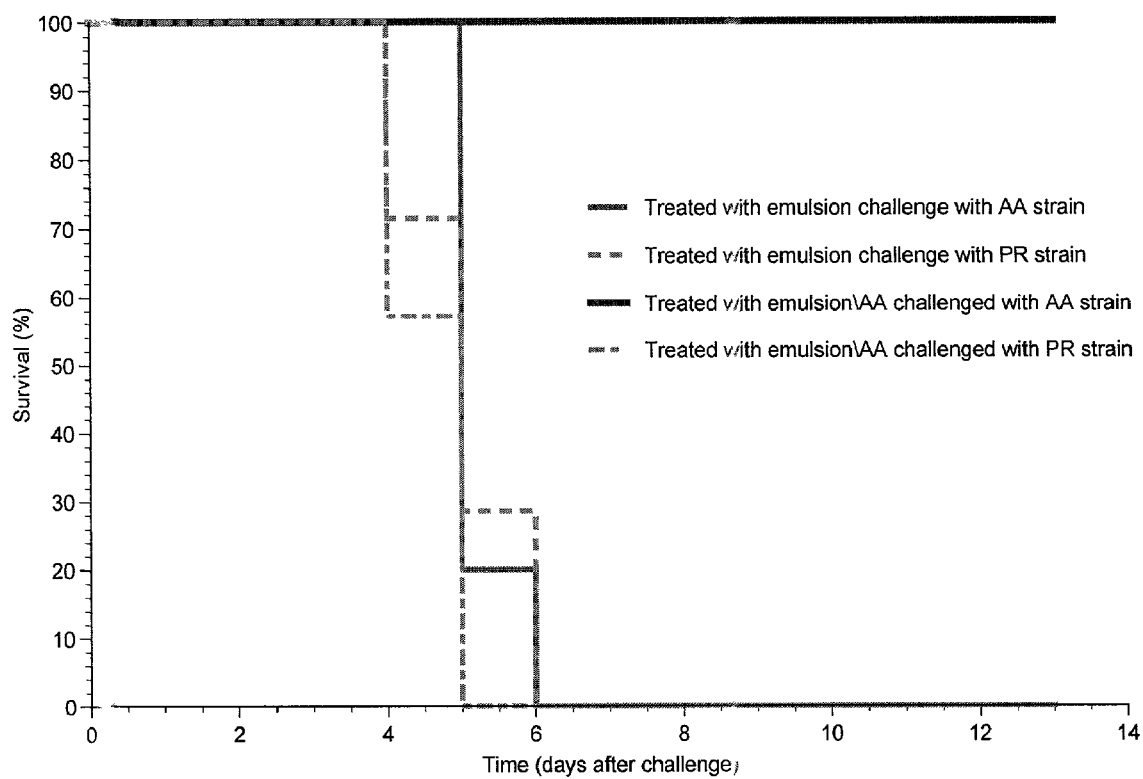

FIG. 19 shows survival curves of animals treated with different preparations intranasally and challenged with lethal dose of influenza A virus either Ann Arbor or Puerto Rico strain.

Figure 20A:
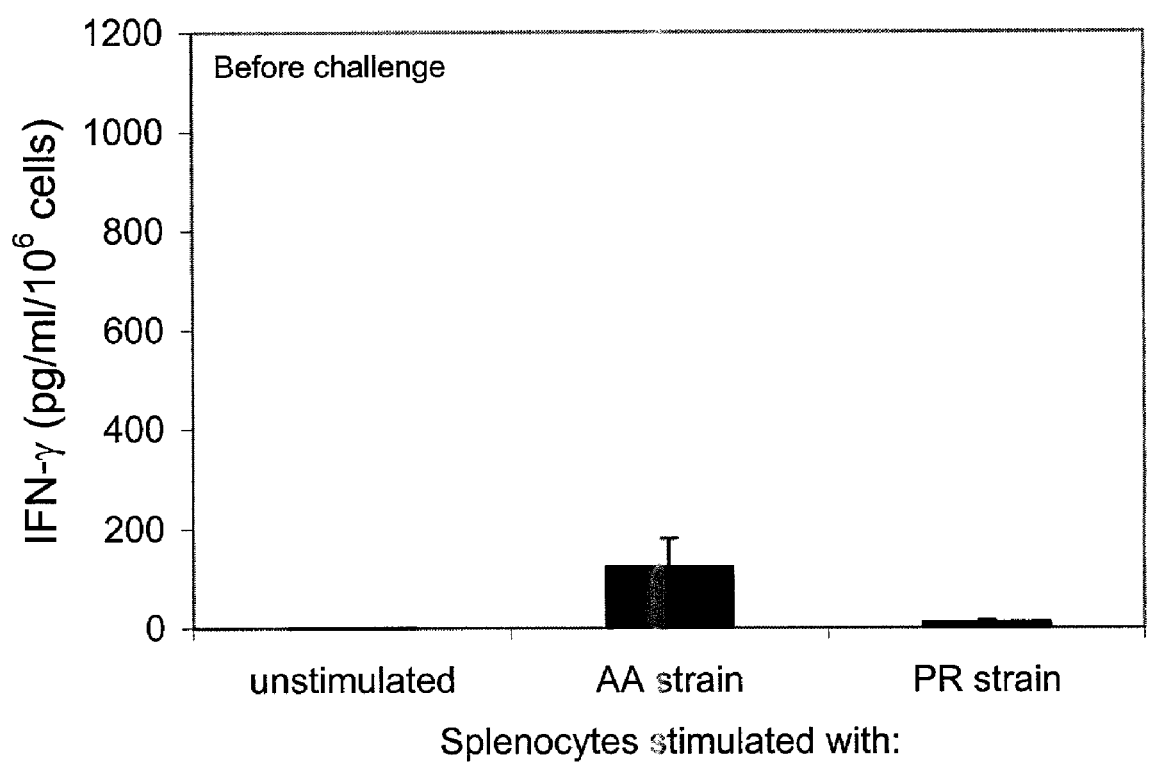
Figure 20B:
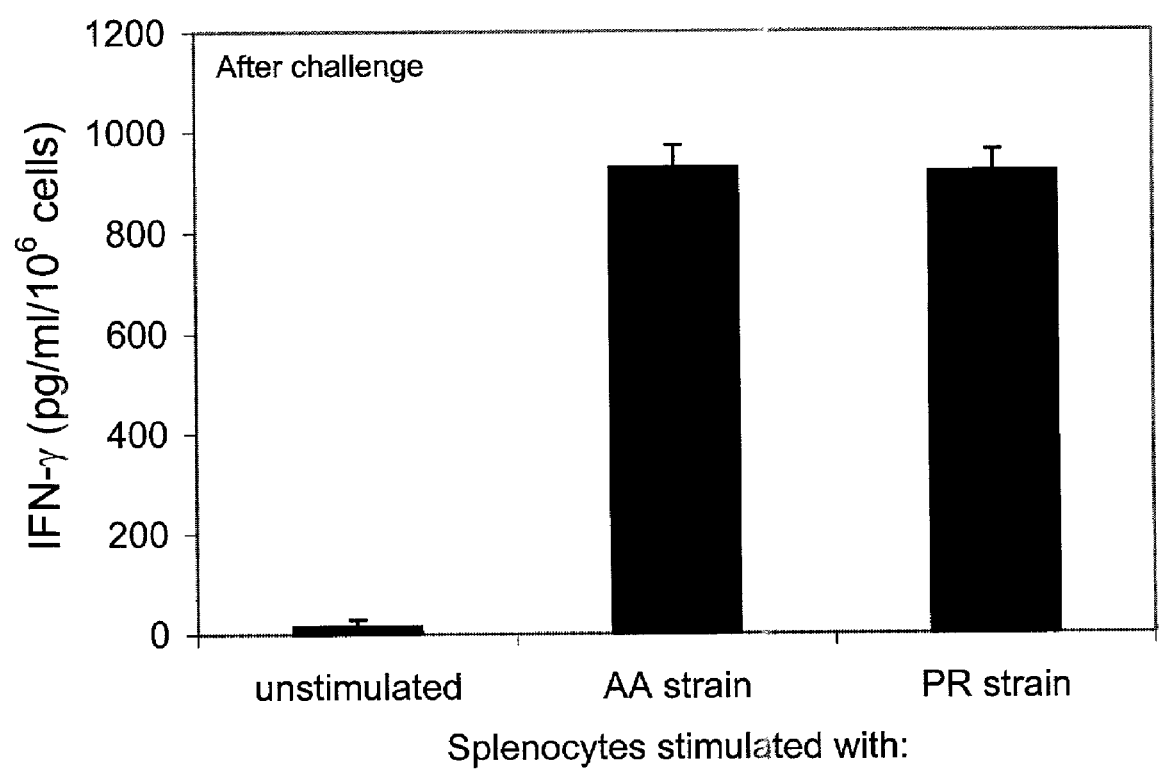
Figure 22:
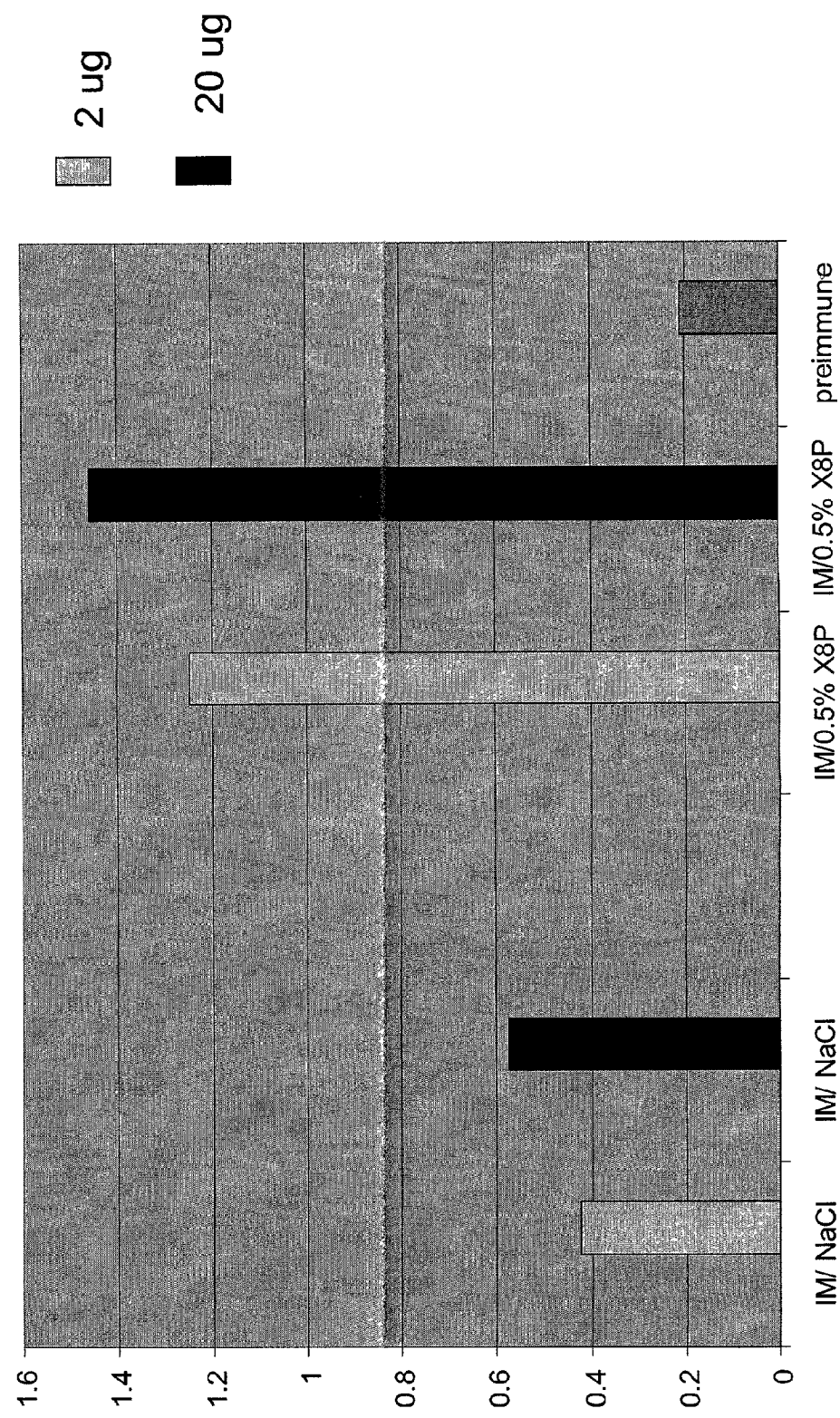

FIG. 20 shows the expansion of the influenza epitope recognition of immunized mice before FIG. 20a) and after (FIG. 20b) challenge with live virus.

GENE DESCRIPTION OF THE INVENTION

The present invention provides methods and compositions for the stimulation of immune responses. Specifically, the present invention provides methods and compositions for the use of nanoemulsion compounds as mucosal adjuvants to induce immunity against environmental pathogens. Accordingly, in some embodiments, the present invention provides mucosal vaccines comprising a pathogen (e.g., an inactivated pathogen) and a nanoemulsion composition. In some embodiments, the pathogen is mixed with the nanoemulsion prior to administration for a time period sufficient to inactivate the pathogen. In others, purified protein components from an pathogen are mixed with the nanoemulsion.

The present invention is not limited to any mechanism of action. Indeed, an understanding of the mechanism is not necessary to practice the present invention. Nonetheless, it is contemplated that the nanoemulsion/pathogen compositions of the present invention stimulate a mucosal immune response against the pathogen component of the vaccine (See e.g., Richter and Kipp, Curr Top Microbiol Immunol 240:159-76 [1999]; Ruedl and Wolf, Int. Arch. Immunol., 108:334 [1995]; and Mor et al., Trends Micrbiol 6:449-53 [1998] for reviews of the mucosal immune system). Mucosal antigens stimulate the Peyer's Patches (PP) of the gastrointestinal tract. The M cells of the PP then transport antigens to the underlying lymph tissue where they encounter B cells and initiate B cell development. IgA is secreted by primed B cells that have been induced to produce IgA by Th2 helper T cells. Primed B cells are transported throughout the lymph system where they populate all secretory tissues. IgAs are then secreted in mucosal tissues where they serve as a first-line defense against many viral and bacterial pathogens.

An optimal prophylactic vaccine against influenza virus should include means to induce both Ab responses and cytotoxic T cell responses (McMichael, Curr. Top. Microbiol. Immunol. 189:75 [1994]). Experiments conducted during the coarse of development of the present invention (See e.g., Example 15) demonstrated that nanoemulsion vaccines of the present invention fulfill both requirements. Immunization with a single dose induced high titer of influenza specific IgG antibodies and titer of antibodies continued to increase after the lethal challenge. There was an early cytokine response (day 4) after single intranasal immunization with virus/nanoemulsion mixture with high levels of IL-12, IFN-$\gamma$, IL-2, TNF-$\alpha$ and IL-10 and absence of anti-inflammatory cytokine IL-4. Since IFN-$\gamma$ is the major cytokine produced in response to viral infection, kinetics of IFN-$\gamma$ production over the period of 20 days after immunization were measured. There was significant amount of IFN-$\gamma$ (200 pg of per milliliter of mouse serum) one day after immunization. Over 10 days, it gradually decreased to undetectable amounts. The immune response against virus was highly specific since mouse splenocytes harvested 20 days after immunization and stimulated with either congenic strain of virus (Ann Arbor) or heterogenic strain of virus (Puerto Rico) responded exclusively toward congenic strain of virus by production of IFN-$\gamma$ and proliferation. Moreover, mice immunized with Ann Arbor strain of virus and challenged with Puerto Rico strain did not survive the lethal challenge. However, the mice immunized with Ann Arbor strain and challenged with the same virus acquired the immunity against heterogenic strain of virus (Puerto Rico strain). The splenocytes from these animals were able to respond by profound production of IFN-$\gamma$ after in vitro stimulation with Puerto Rico virus. Furthermore, these animals were fully protected against lethal challenge with heterogenic virus, i.e Puerto Rico strain.

The present invention is not limited to a particular mechanism. Indeed, an understanding of the mechanism is not necessary to practice the present invention. Nonetheless, it is contemplated that this observation suggests an immunodominance effect (Sercarz et al., Anu Rev Immunol 11:729 [1993]; Perreault et al., Immunol Today 19:69 [1998]), which has been found to regulate cytotoxic T lymphocyte (CTL) responses to viruses (Silins et al., J Exp Med 184: 1815 [1996]: Steven et al, J Exp Med 184:1801 [1996]). It appears that only a very small portion of epitopes, probably less than 10%, are dominant (Tremblay et al., Transplantation 58:59 [1994]; Brochu et al., J Immunol 155:5104 [1995]). During the process of vaccination, the presence of immunodominant epitopes prevented recognition of nondominant determinants and therefore animals responded exclusively toward congenic strain of virus. However, after both vaccination and the lethal challenge with congenic virus (Ann Arbor), animals expanded the epitope recognition and developed the response to nondominant determinants acquiring immune protection against heterogenic virus.

Experiments conducted during the course of the development of the present invention strongly support the notion that as little as a single intranasal instillation of virus/nanoemulsion mixture works as mucosal vaccine and is able to stimulate strong and specific immune response against influenza A virus. The vaccine was prepared by mixing the $5 \times 10^5$ pfu of virus with equal volume of 4% nanoemulsion and incubated at RT for one hour prior to mucosal vaccination of animals. Although the reduction of virus was greater than three logs after one hour incubation of the virus with nanoemulsion, there was an incomplete viral inactivation with about 100 pfu of intact virus remaining, based on viral plaque assay. These finding led to an investigation of whether a small number of intact viral particles alone could be effective in immunization of mice. As shown in Table 28, up to $2 \times 10^3$ pfu of virus per mouse administrated intranasally did not rest It in protected immunity since all animals challenged with lethal dose of virus succumbed to pneumonia and died. Low doses of virus were not effective and higher dose of intact virus caused sickness and death within the first 3 days after intranasal treatment. These data clearly demonstrated that, in addition to nanoemulsion and nanoemulsion-inactivated virus, a small dose of intact virus was useful for mucosal vaccination of experimental animals. This conclusion was also supported by the observation that formalin-inactivated virus mixed with nanoemulsion and administrated intranasally to animals did not protect them from lethal challenge with influenza A virus.

The nasally administered nanoemulsion vaccine compositions of the present invention have several advantages over parenterally administered vaccines. The vaccines can be easily administered when needed (e.g., immediately before or directly after exposure to the pathogen). When administered after exposure (e.g., after exposure of troops to a biological weapon), immune protection occurs specifically when needed. It is at this time that ongoing pathogen exposure might lead to infection. The administration methods of the present invention also avoid the need for expensive and problematic prophylactic vaccine programs. This approach provides the individual with specific immunity to the exact organisms exposed to, regardless of genetic or antigenic manipulation. The methods of the present invention are particularly valuable since they avoid the need for actual infection to induce immunity since even an attenuated infection can have undesired consequences. The present invention further provides methods of using nanoemulsions as adjuvants for parenteral administered vaccines. The present invention thus provides a rapid, killed vaccine for a range of naturally occurring and human administered pathological agents.

DEFINITIONS

To facilitate an understanding of the present invention, a number of terms and phrases are defined below:

As used herein the term "microorganism" refers to microscopic organisms and taxonomically related macroscopic organisms within the categories of algae, bacteria, fungi (including lichens), protozoa, viruses, and subviral agents. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism. As used herein the term "pathogen," and grammatical equivalents, refers to an organism, including microorganisms, that causes disease in another organism (e.g., animals and plants) by directly infecting the other organism, or by producing agents that causes disease in another organism (e.g., bacteria that produce pathogenic toxins and the like).

As used herein the term "disease" refers to a deviation from the condition regarded as normal or average for members of a species or group, and which is detrimental to an affected individual under conditions that are not inimical to the majority of individuals of that species or group (e.g., diarrhea, nausea, fever, pain, and inflammation etc). A disease may be caused or result from contact by microorganisms and/or pathogens.

The terms "host" or "subject," as used herein, refer to organisms to be treated by the compositions and methods of the present invention. Such organisms include organisms that are exposed to, or suspected of being exposed to, one or more pathogens. Such organisms also include organisms to be treated so as to prevent undesired exposure to pathogens. Organisms include but are not limited to animals (e.g., humans, domesticated animal species, wild animals) and plants.

As used herein, the term "inactivating," and grammatical equivalents, means having the ability to kill, eliminate or reduce the capacity of a pathogen to infect and/or cause a pathological responses in a host.

As used herein, the term "fusigenic" is intended to refer to an emulsion that is capable of fusing with the membrane of a microbial agent (e.g., a bacterium or bacterial spore). Specific examples of fusigenic emulsions include, but are not limited to, $W_{80}8P$ described in U.S. Pat. Nos. 5,618,840; 5,547,677; and 5,549,901 and NP9 described in U.S. Pat. No. 5,700,679, each of which is herein incorporated by reference in their entireties. NP9 is a branched poly(oxy-1,2 ethaneolyl), alpha-(4-nonylphenal)-omega-hydroxy-surfactant. While not being limited to the following, NP9 and other surfactants that may be useful in the present invention are described in Table 1 of U.S. Pat. No. 5,662,957, herein incorporated by reference in its entirety.

As used herein, the term "lysogenic" refers to an emulsion that is capable of disrupting the membrane of a microbial agent (e.g., a bacterium or bacterial spore). In preferred embodiments of the present invention, the presence of both a lysogenic and a fusigenic agent in the same composition produces an enhanced inactivating effect than either agent alone. Methods and compositions (e.g., vaccines) using this improved antimicrobial composition are described in detail herein.

The term "emulsion," as used herein, includes classic oil-in-water or water in oil dispersions or droplets, as well as other lipid structures that can form as a result of hydrophobic forces that drive a polar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in preferred embodiments, the nanoemulsions comprise an oil phase having droplets with a mean particle size of approximately 0.1 to 5 microns, although smaller and larger particle sizes are contemplated. The terms "emulsion" and "nanoemulsion" are often used herein, interchangeably, to refer to the nanoemulsions of the present invention.

As used herein, the terms "contacted" and "exposed," refers to bringing one or more of the compositions of the present invention into contact with a pathogen or a subject to be protected against pathogens such that the compositions of the present invention may inactivate the microorganism or pathogenic agents, if present. The present invention contemplates that the disclosed compositions are contacted to the pathogens or microbial agents in sufficient volumes and/or concentrations to inactivate the pathogens or microbial agents.

The term "surfactant" refers to any molecule having both a polar head group, which energetically prefers solvation by water, and a hydrophobic tail that is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described by Meyers, (Meyers, *Surfactant Science and Technology*, VCH Publishers Inc., New York, pp. 231-245 [1992]), incorporated herein by reference. As used herein, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein, the term "germination enhancers" describe compounds that act to enhance the germination of certain strains of bacteria (e.g., L-amino acids [L-alanine], $CaCl_2$, Inosine, etc).

As used herein the term "interaction enhancers" refers to compounds that act to enhance the interaction of an emulsion with the cell wall of a bacteria (e.g., a Gram negative bacteria). Contemplated interaction enhancers include, but are not limited to, chelating agents (e.g., ethylenediaminetetraacetic acid [EDTA], ethylenebis(oxyethylenenitrilo)tetraacetic acid [EGTA], and the like) and certain biological agents (e.g., bovine serum abulmin [BSA] and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "therapeutic agent," refers to compositions that decrease the infectivity, morbidity, or onset of mortality in a host contacted by a pathogenic microorganism or that prevent infectivity, morbidity, or onset of mortality in a host contacted by a pathogenic microorganism. Such agents may additionally comprise pharmaceutically acceptable compounds (e.g., adjuvants, excipients, stabilizers, diluents, and the like). In some embodiments, the therapeutic agents (e.g., vaccines) of the present invention are administered in the form of topical emulsions, injectable compositions, ingestible solutions, and the like. When the route is topical, the form may be, for example, a spray (e.g., a nasal spray).

The terms "pharmaceutically acceptable" or "pharmacologically acceptable," as used herein refer to compositions that do not substantially produce adverse allergic or immunological reactions when administered to a host (e.g., an animal or a human). As used herein, "pharmaceutically acceptable carrier" includes any and all solvents, dispersion media, coatings, wetting agents (e.g., sodium lauryl sulfate), isotonic and absorption delaying agents, disintigrants (e.g., potato starch or sodium starch glycolate), and the like.

As used herein, the term "topically" refers to application of the compositions of the present invention to the surface of the skin and mucosal cells and tissues (e.g., alveolar, buccal, lingual masticatory, or nasal mucosa, and other tissues and cells which line hollow organs or body cavities).

As used herein, the term "topically active agents" refers to compositions of the present invention that illicit a pharmacological response at the site of application (contact) to a host.

As used herein, the term "systemically active drugs" is used broadly to indicate a substance or composition that will produce a pharmacological response at a site remote from the point of application or entry into a subject.

As used herein, the term "adjuvant" refers to an agent that increases the immune response to an antigen (e.g., a pathogen). A used herein, the term "immune response" refers to a subject's (e.g., a human or another animal) response by the immune system to immunogens (i.e., antigens) the subject's immune system recognizes as foreign. Immune responses include both cell-mediated immune responses (responses mediated by antigen-specific T cells and non-specific cells of the immune system) and humnasal immune responses (responses mediated by antibodies present in the plasma lymph, and tissue fluids). The term "immune response" encompasses both the initial responses to an immunogen (e.g., a pathogen) as well as memory responses that are a result of "acquired immunity."

As used herein, the term "immunity" refers to protection from disease upon exposure to a pathogen. Immunity can be innate (immune responses that exist in the absence of exposure to an antigen) and/or acquired (immune responses that are mediated by B and T cells following exposure to antigen and that exhibit specificity to the antigen).

As used herein, the term "immunogen" refers to an antigen that is capable of eliciting an immune response in a subject. In preferred embodiments, immunogens elicit immunity against the immunogen (e.g., a pathogen or a pathogen product) when administered in combination with a nanoemulsion of the present invention.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of acquired immunity to a given pathogen following administration of a vaccine of the present invention relative to the level of acquired immunity when a vaccine of the present invention has not been administered.

As used herein, the term "purified" or "to purify" refers to the removal of contaminants or undesired compounds from a sample or composition. As used herein, the term "substantially purified" refers to the removal of from about 70 to 90%, up to 100%, of the contaminants or undesired compounds from a sample or composition.

As used herein, the term "surface" is used in its broadest sense. In one sense, the term refers to) the outermost boundaries of an organism or inanimate object (e.g., vehicles, buildings, and food processing equipment, etc.) that are capable of being contacted by the compositions of the present invention (e.g., for animals: the skin, hair, and fur, etc., and for plants: the leaves, stems, flowering parts, and fruiting bodies, etc.). In another sense, the term also refers to the inner membranes and surfaces of animals and plants (e.g., for animals: the digestive tract, vascular tissues, and the like, and for plants: the vascular tissues, etc.) capable of being contacted by compositions by any of a number of transdermal delivery routes (e.g., injection, ingestion, transdermal delivery, inhalation, and the like).

As used herein, the term "sample" is used in its broadest sense. In one sense it can refer to animal cells or tissues. In another sense, it is meant to include a specimen or culture obtained from any source, such as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DETAILED DESCRIPTION OF THE INVENTION

The present invention provides methods and compositions for the stimulation of specific immune response. Accordingly, in some embodiments, the present invention provides vaccines for the stimulation of immunity against pathogens. In some embodiments, the present invention provides nanoemulsion vaccine compositions comprising an inactivated pathogen and a nanoemulsion. The present invention is not limited to any particular nanoemulsion or pathogen.

Exemplary vaccine compositions and methods of administering vaccine compositions are described in more detail below.

I. Nanoemulsions as Anti-Pathogen Compositions

The nanoemulsion compositions utilized in some embodiments of the present invention have demonstrated anti-pathogen effect. For example, nanoemulsion compositions have been shown to inactivate bacteria (both vegetative and spore forms), virus, and fungi. In preferred embodiments of the present invention, pathogens are inactivated by exposure to nanoemulsions before teeing administered as vaccines.

A. Microbiocidal and Microbistatic Activity

Nanoemulsion compositions can be used to rapidly inactivate bacteria. In certain embodiments, the compositions are particularly effective at inactivating Gram positive bacteria. In preferred embodiments, the inactivation of bacteria occurs after about five to ten minutes. Thus, bacteria may be contacted with an emulsion and will be inactivated in a rapid and efficient manner. It is expected that the period of time between the contacting and inactivation may be as little as 5-10 minutes where the bacteria is directly exposed to the emulsion. However, it is understood that when nanoemulsions are employed in a therapeutic context and applied systemically, the inactivation may occur over a longer period of time including, but not limited to, 5, 10, 15, 20, 25 30, 60 minutes post application. Further, in additional embodiments, inactivation may take two, three, four, five or six hours to occur.

Nanoemulsions can also rapidly inactivate certain Gram negative bacteria for use in generating the vaccines of the present invention. In such methods, the bacteria inactivating emulsions are premixed with a compound that increases the interaction of the emulsion by the cell wall. The use of these enhancers in the vaccine compositions of the present invention is discussed herein below. It should be noted that certain emulsions (e.g., those comprising enhancers) are effective against certain Gram positive and negative bacteria.

In specific illustrative examples (Examples 3-4), nanoemulsions useful in the compositions and methods of the present invention were shown to have potent, selective biocidal activity with minimal toxicity against vegetative bacteria. For example, X8P was highly effective against *B. cereus, B. circulans* and *B. megaterium, C. perfringens, H. influenzae, N. gonorrhoeae, S. agalactiae, S. pneumonia, S. pyogenes* and *V. cholerae* classical and Eltor (FIG. 26). This inactivation starts immediately on contact and is complete within 15 to 30 minutes for most of the susceptible microorganisms.

B. Sporicidial and Sporistatic Activity

In certain specific examples (e.g., Examples 5 and 11), nanoemulsions have been shown to have anti-sporicidal activity. Without being bound to any theory (an understanding of the mechanism is not necessary to practice the present invention, and the present invention is not limited to any particular mechanism), it is proposed the that the sporicidal ability of these emulsions occurs through initiation of germination without complete reversion to the vegetative form leaving the spore susceptible to disruption by the emulsions. The initiation of germination could be mediated by the action of the emulsion or its components.

The results of electron microscopy studies show disruption of the spore coat and cortex with disintegration of the core contents following X8P treatment. Sporicidal activity appears to be mediated by both the TRITON X-100 and tri-n-butyl phosphate components since nanoemulsions lacking either component are inactive in vivo. This unique action of the emulsions, which is similar in efficiency to 1% bleach is interesting because *Bacillus* spores are generally resistant to most disinfectants including may commonly used detergents (Russell, Clin. Micro. 3; 99 [1990]).

Certain illustrative examples of the present invention demonstrate that mixing X8P with *B. cereus* spores before injecting into mice prevents the pathological effect of *B. cereus* (Example 5). Further, illustrative examples of the present invention show that X8P treatment of simulated wounds contaminated with *B. cereus* spores markedly reduced the risk of infection and mortality in mice (Example 5). The control animals, injected with X8P alone diluted 1:10, did not show any inflammatory effects, thus demonstrating that X8P does not have cutaneous toxicity in mice. These results suggest that immediate treatment of spores prior to or following exposure can effectively reduce the severity of tissue damage of the experimental cutaneous infection.

Other experiments conducted during the development of the present invention compared the effects of X8P and other emulsions derived from X8P to inactivate different *Bacillus* spores (Example 11). X8P diluted up to 1:1000 (v/v) inactivated more than 90% of *B. anthracis* spores in four hours, and was also sporicidal against three other Bacillus species through the apparent disruption of spore coat. $X8W_{60}PC$ diluted 1:1000 had more sporicidal activity against *B. anthracis, B. cereus,* and *B. subtilis* and had an onset of action in less than 30 minutes. In mice, mixing X8P with *B. cereus* before subcutaneous injection or wound irrigation with X8P 1 hour following spore inoculation resulted in over 98% reduction in skin lesion size. Mortality was reduced 4-fold in the latter experiment. The present compositions are stable, easily dispersed, non-irritant and nontoxic compared to the other available sporicidal agents.

Figure 1:
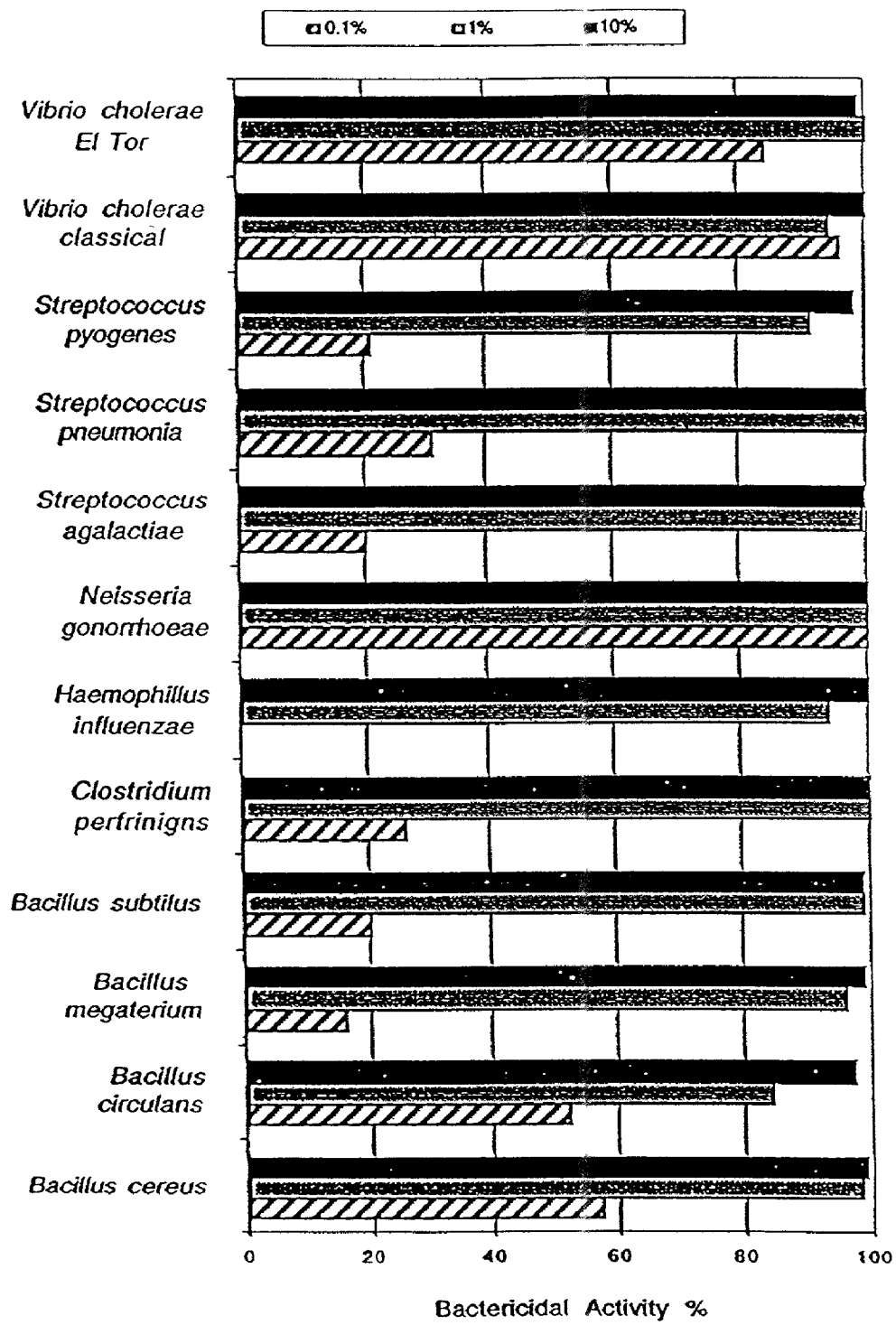

The bacteria-inactivating oil-in-water emulsions used in some embodiments of the present invention can be used to inactivate a variety of bacteria and bacterial spores upon contact. For example, the presently disclosed emulsions can be used to inactivate *Bacillus* including *B. cereus, B. circulans* and *B. megatetium*, also including *Clostridium* (e.g., *C. botulinum* and *C. tetani*). The nanoemulsions utilized in some embodiments of the present invention may be particularly useful in inactivating certain biological warfare agents (e.g., *B. anthracis*). In addition, the formulations of the present invention also find use in combating *C. perfringens, H. influenzae, N. gonorrhoeae, S. agalactiae, S. pneumonia, S. pyogenes* and *V. cholerae* classical and Eltor (FIG. 1).

C. Viricidal and Viralstatic Activity

In additional illustrative examples (e.g., Example 12) of the present invention, it was demonstrated that the nanoemulsion compositions of the present invention have anti-viral properties. The effect of these emulsions on viral agents was monitored using plaque reduction assay (PRA), cellular enzyme-linked immunosorbent assay (ELISA), β-galactosidase assay, and electron microscopy (EM) and the cellular toxicity of lipid preparations was assessed using a (4,5-dimethylthiazole-2-yl)-2,5 diphenyltetrazolium (MTT) staining assay (Mosmann, J. Immunol. Methods., 65:55 [1983]).

There was a marked reduction of influenza A infectivity of MDCK cells as measured by cellular ELISA with subsequent confirmation by PRA. X8P and SS at a dilution of 1:10 reduced virus infectivity over 95%. Two other emulsions showed only intermediate effects on the virus reducing infectivity by approximately 40% at dilution 1:10. X8P was the most potent preparation and showed undiminished viricidal effect even at dilution 1:100. Kinetic studies showed that 5 min incubation of virus with X8P at 1:10 dilution completely abolished its infectivity. TRITON X-100, an active compound of X8P, at dilution 1:5000 only partially inhibited the infectivity of virus as compared to X8P, indicating that the nanoemulsion itself contributes to the anti-viral efficacy. To further examine the anti-viral properties of X8P, its action on non-enveloped viruses was investigated. The X8P treatment did not affect the replication of lacZ adenovirus construct in 293 cells as measured using β-galactosidase assay. When examined with EM, influenza A virus was completely disrupted after incubation with X8P while adenovirus remained intact.

In addition, pre-incubation of virus with 10% and 1% X8P in PBS completely eliminates herpes, sendai, sindbis and vaccinia viruses as assessed by plaque reduction assays (FIG. 2). Time course analyses showed the onset of inactivation to be rapid and complete within 5 minutes of incubation with 10% X8P and within 30 minutes with 1% X8P. Adenovirus treated with different dilutions of X8P showed no reduction in infectivity.

The efficacy of certain X8P based compositions against various viral onslaught and their minimal toxicity to mucous membranes demonstrate their potential as effective disinfectants and agents for prevention of diseases resulting from infection with enveloped viruses.

D. Fungicidal and Fungistatic Activity

Yet another property of the nanoemulsions used in some embodiments of the present invention is that they possess antifungal activity. Common agents of fungal infections include various species of the genii *Candida* and *Aspergillus*, and types thereof, as well as others. While external fungus infections can be relatively minor, systemic fungal infections can give rise to serious medical consequences. There is an increasing incidence of fungal infections in humans, attributable in part to an increasing number of patients having impaired immune systems. Fungal disease, particularly when systemic, can be life threatening to patients having an impaired immune system.

Experiments conducted during the development of the present invention have shown that 1% X8P has a greater than 92% fungistatic activity when applied to *Candida albicans*. *Candida* was grown at 37° C. overnight. Cells were then washed and counted using a hemacytometer. A known amount of cells were mixed with different concentrations of X8P and incubated for 24 hours. The *Candida* was then grown on dextrose agar, incubated overnight, and the colonies were counted. The fungistatic effect of the X8P was determined as follows:

$$\text{Fungistatic effect } (FSE) = 1 - \frac{\text{\# of treated cells} - \text{Initial \# of cells}}{\text{\# of untreated cells} - \text{Initial \# of cells}} \times 100$$

It is contemplated that other nanoemulsion formulations useful in the methods and compositions of the present invention (e.g., described below) are also fungistatic. One of skill in the art will be able to test additional formulations for their ability to inactivate fungi (e.g., using methods described herein).

E. In Vivo Effects

In other illustrative examples of the present invention, nanoemulsion formulations were shown to combat and prevent pathogen infection in animals. *Bacillus cereus* infection in experimental animals has been used previously as a model system for the study of anthrax (See e.g., Burdon and Wende, J Infect. Diseas. 170(2):272 [1960]; Lamanna and Jones, J. Bact. 85:532 [1963]; and Burdon et al., J Infect. Diseas. 117:307 [1967]). The disease syndrome induced in animals experimentally infected with *B. cereus* is similar to *B. anthracis* (Drobniewski, Clin. microbio. Rev. 6:324 [1993]; and Fritz et al., Lab. Invest. 73:691 [1995]). Experiments conducted during the development of the present invention demonstrated that mixing X8P with *B. cereus* spores before injecting into mice prevented the pathological effect of *B. cereus*. Further, it was demonstrated that X8P treatment of simulated wounds contaminated with *B. cereus* spores markedly reduced the risk of infection and mortality in mice. The control animals, which were injected with X8P alone diluted 1:10, did not show any inflammatory effects proving that X8P does not have cutaneous toxicity in mice. These results suggest that immediate treatment of spores prior to or following exposure can effectively reduce the severity of tissue damage of the experimental cutaneous infection.

In a particular example, Guinea Pigs were employed as experimental animals for the study of *C. perfringens* infection. A 1.5 cm skin wound was made, the underlying muscle was crushed and infected with $5 \times 10^7$ cfu of *C. perfringens* without any further treatment. Another group was infected with the same number of bacteria, then 1 hour later it was irrigated with either saline or X8P to simulate post-exposure decontamination. Irrigation of experimentally infected wounds with saline did not result in any apparent benefit. However, X8P irrigation of the wound infected with *C. perfringens* showed marked reduction of edema, inflammatory reaction and necrosis. As such, it was demonstrated that certain nanoemulsion formulations are able to combat a bacterial infection.

Further, a subcutaneous injection of 10% X8P did not cause distress in experimental animal, and resulted in no gross histological tissue damage. All rats in the nasal toxicity study showed weight gain over the study period. No adverse clinical signs were noted and all tissues appeared within normal limits on gross examination. Bacterial cultures from the stools of treated animals were not significantly different from those of untreated animals.

II. Nanoemulsion Vaccine Compositions

In some embodiments, the present invention provides vaccine compositions comprising a nanoemulsion and one or more inactivated pathogens or pathogen products. The present invention provides vaccines for any number of pathogens. The present invention is not limited to any particular nanoemulsion formulation. Indeed, a variety of nanoemulsion formulations are contemplated (See e.g., below description and illustrative Examples and US Patent Application 20020045667, herein incorporated by reference).

The immunogens (e.g., pathogens or pathogen products) and nanoemulsions of the present invention may be combined in any suitable amount utilizing a variety of delivery methods. Any suitable pharmaceutical formulation may be utilized, including, but not limited to, those disclosed herein. Suitable vaccine formulation may be tested for immunogenicity using any suitable method. For example, in some embodiments, immunogenicity is investigated by quantitating both antibody titer and specific T-cell responses. Nanoemulsion vaccines may also be tested in animal models of infectious disease states. Suitable animal models, pathogens, and assays for immunogenicity include, but are not limited to, those described below.

A. Nanoemulsions as Immune Adjuvants

The ability of nanoemulsions to prevent infections in a prophylactic manner when applied to either wounds, skin or mucous membranes has been documented (Hamouda et al., J. Infect. Dis.,180:1939 [1999]; Donovan et al., Antivir Chem Chemother., 11:41 [2000]). During the development of the present invention, in several studies, mice were pretreated with nasally applied nanoemulsion before exposure to influenza virus to document the ability of the nanoemulsions to prevent inhalation influenza pneumonitis. Morbidity from pretreatment with nanoemulsion was minimal and, as compared to control animals, mortality was greatly diminished (20% with pretreatment vs. 80% in controls; Example 13). Several of the surviving, emulsion pretreated animals were found to have evidence of a few areas of immune reactivity and giant-cell formation in the lung that were not present in control animals treated with emulsion but not exposed to virus. All of the pretreated animals had evidence of lipid uptake in lung macrophages. The present invention is not limited to any one mechanism. Indeed, an understanding of the mechanism is not necessary to practice the present invention. Nonetheless, it is contemplated that the treatment with a nanoemulsion/virus composition resulted in the development of immunity to the influenza virus.

Therefore, in one illustrative example (Example 13) antibody titers to influenza virus in the serum of exposed animals were investigated. It was found that animals receiving emulsion and virus had high titers of virus-specific antibody (FIG. 6). This immune response was not observed in control animals exposed to virus without pretreatment.

Experiments were conducted to investigate whether administration of emulsion and virus would yield protective immunity without toxicity (Example 13). A mixture of virus ($LD_{80}$; $5 \times 10^4$ pfu) with the nanoemulsion was administered to animals on two occasions, two weeks apart. As controls, animals were given either an equal amount of formalin-killed virus, nanoemulsion alone or saline. The results of these studies demonstrated that only the emulsion/virus mixture elicited significant antibody response when applied to the narcs of animals. The titers were extremely high and included both serum IgG and bronchial IgA responses that were specific for the virus (FIGS. 7 and 8). More importantly, in two repeated experiments, complete protection from death was observed in the emulsion/virus pretreatment group (Table 25). None of the 15 animals died from exposure to a $LD_{80}$ of virus after two administrations of $5 \times 10^4$ pfu of virus mixed in nanoemulsion, whereas the expected 80% of control animals died from this exposure. The same dose of formalin killed virus applied to the narcs provided no protection from death and resulted in much lower titers of virus-specific antibody (FIGS. 7 and 8).

Experiments were also conducted to investigate the possibility that a small amount of residual, live virus in the nanoemulsion was producing a subclinical infection that provided immunity (Example 13). An additional group of animals were given approximately 100 pfu of live virus intranasally in an attempt to induce a low-level infection (approximately four times the amount of live virus present after 15 minutes of treatment with nanoemulsion). While there was a slight reduction in death rates of these animals, suggesting a sub-clinical infection, the amount of protection observed was significantly less than what was seen in the emulsion treated group and none of these animals developed virus-specific antibodies (Table 25). This documented that it was not merely a sub-lethal viral infection mediating the immune response but that the emulsion was specifically enhancing the virus-specific immune response. The protective immunity was obtained following only two applications of the emulsion/virus mix, and appeared to increase after each application suggesting a booster effect. Virus-specific antibody titers were maintained for six weeks following administration of the emulsion/virus mix.

Illustrative Example 15 demonstrates the ability of intranasally administered influenza virus/nanoemulsion was able to induce immunity in mice against further challenge with live virus.

The present invention is not limited to the intranasal administration of vaccine compounds. Parenteral methods of administration are also contemplated. For example, illustrative example 16 demonstrates that parenteral administration of HIV gp120 protein nanoemulsion induced an immune response in mice. The present invention is also not limited to the use of vaccines comprising whole pathogens. The use of pathogen products (e.g., including, but not limited to, proteins, polypeptides, peptides, nucleic acids, membrane fractions, and polysaccharides) is contemplated. Illustrative example 16 demonstrates the generation of an immune response against HIV gp120 protein.

B. Pathogens

The present invention is not limited to the use of any one specific type of pathogen. Indeed vaccines to a variety of pathogens are within the scope of the present invention. Accordingly, in some embodiments, the present invention provides vaccines to bacterial pathogens in vegetative or spore forms (e.g., including but not limited to, *Bacillus cereus, Bacillus circulans* and *Bacillus megaterium, Bacillus anthracis, Clostridium perfringens, Vibrio cholerae, Streptococcus pyogenes, Streptococcus agalactiae, Streptococcus pneumonia, Staphylococcus aureus, Neisseria gonorrhea, Haemophilus influenzae, Escherichia coli, Salmonella typhimurium, Shigella dysenteriae, Proteus mirabilis, Pseudomonas aeruginosa, Yersinia enterocolitica*, and *Yersinia pseudotuberculosis*). In other embodiments, the present invention provides vaccines to viral pathogens (e.g., including, but not limited to, influenza A, herpes simplex virus I, herpes simplex virus II, sendai, sindbis, vaccinia, parvovirus, human immunodeficiency virus, hepatitis B, virus hepatitis C virus, hepatitis A virus, cytomegalovirus, and human papilloma virus, picornavirus, hantavirus, junin virus and ebola virus). In still further embodiments, the present invention provides vaccines to fungal pathogens, including, but not limited to, *Candida albicans* and *parapsilosis, Aspergillus fumigates* and *niger, Fusarium spp, Trychophyton spp*.

Bacteria for use in formulating the vaccines of the present invention can be obtained from commercial sources, including, but not limited to, American Type Culture Collection (ATCC). In some embodiments, bacteria are passed in animals prior to being mixed with nanoemulsions in order to enhance their pathogenicity for each specific animal host for 5-10 passages (Sinai et al., J. Infect. Dis., 141:193 [1980]). In some embodiments, the bacteria then are then isolated from the host animals, expanded in culture and stored at −80° C. Just before use, the bacteria are thawed and grown on an appropriate solid bacterial culture medium overnight. The next day, the bacteria are collected from the agar plate and suspended in a suitable liquid solution (e.g., Brian Heart Infusion (BHI) broth). The concentration of bacteria is adjusted so that the bacteria count is approximately $1.5 \times 10^8$ colony forming units per ml (CFU/ml), based on the McFarland standard for bactericidal testing (Hendrichson and Krenz, 1991).

Viruses for use in formulating the vaccines of the present invention can be obtained from commercial sources, including, but not limited, ATCC. In some embodiments, viruses are passed in the prospective animal model for 5-10 times to enhance pathogenicity for each specific animal (Ginsberg and Johnson, Infect. Immun., 13:1221 [1976]). In some embodiments, the virus is collected and propagated in tissue culture and then purified using density gradient concentration and ultracentrifugation (Garlinghouse et al., Lab Anim Sci., 37:437 [1987]; and Mahy, Br. Med. Bull., 41:50 [1985]). The Plaque Forming Units (PFU) are calculated in the appropriate tissue cells.

Lethal dose and/or infectious dose for each pathogen can be calculated using any suitable method, including, but not limited to, by administering different doses of the pathogens to the animals by the infective route and identifying the doses which result in the expected result of either animal sickness or death based on previous publications (Fortier et al., Infect Immun., 59:2922 [1991]; Jacoby, Exp Gerontol., 29:89 [1994]; and Salit et al., Can J Microbiol., 30:1022 [1984]).

C. Nanoemulsions

The nanoemulsion vaccine compositions of the present invention are not limited to any particular nanoemulsion.

Any number of suitable nanoemulsion compositions may be utilized in the vaccine compositions of the present invention, including, but not limited to, those disclosed in Hamouda et al., J. Infect Dis., 180:1939 [1999]; Hamouda and Baker, J. Appl. Microbiol., 89:397 [2000]; and Donovan et al., Antivir. Chem. Chemother., 11:41 [2000], as well as those shown in Tables 1 and 2 and FIGS. 4 and 9. Preferred nanoemulsions of the present invention are those that are effective in killing or inactivating pathogens and that are non-toxic to animals. Accordingly, preferred emulsion formulations utilize non-toxic solvents, such as ethanol, and achieve more effective killing at lower concentrations of emulsion. In preferred embodiments, nanoemulsions utilized in the methods of the present invention are stable, and do not decompose even after long storage periods (e.g., one or more years). Additionally, preferred emulsions maintain stability even after exposure to high temperature and freezing. This is especially useful if they are to be applied in extreme conditions (e.g., on a battlefield). In some embodiments, one of the nanoemulsions described in Table 1 and or FIGS. 4 or 9 is utilized.

In some preferred embodiments, the emulsions comprise (i) an aqueous phase; (ii) an oil phase; and at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in the compositions of the present invention include but are not limited to one or more, organic, and more particularly, organic phosphate based solvents, surfactants and detergents, quaternary ammonium containing compounds, cationic halogen containing compounds, germination enhancers, interaction enhancers, and pharmaceutically acceptable compounds. Certain exemplary embodiments of the various compounds contemplated for use in the compositions of the present invention are presented below.

TABLE 1

Nanoemulsion Formulations

| Name | Oil Phase Formula | Water to Oil Phase Ratio (Vol/Vol) |
|---|---|---|
| X8P | 1 vol. Tri(N-butyl)phosphate<br>1 vol. TRITON X-100<br>8 vol. Soybean oil | 4:1 |
| NN | 86.5 g Glycerol monooleate<br>60.1 ml Nonoxynol-9<br>24.2 g GENEROL 122<br>3.27 g Cetylpyridinium chloride<br>554 g Soybean oil | 3:1 |
| $W_{80}8P$ | 86.5 g Glycerol monooleate<br>21.2 g Polysorbate 60<br>24.2 g GENEROL 122<br>3.27 g Cetylpyddinium chloride<br>4 ml Peppermint oil<br>554 g Soybean oil | 3.2:1 |
| SS | 86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth in water) |

TABLE 1-continued

Nanoemulsion Formulations

| Name | Oil Phase Formula | Water to Oil Phase Ratio (Vol/Vol) |
|---|---|---|
| | 3.27 g Cetylpyridinium chloride<br>554 g Soybean oil | |

TABLE 2

Nanoemulsion Formulations

| Nanoemulsion | Composition |
|---|---|
| X8P | 8% TRITON X-100; 8% Tributyl phosphate; 64% Soybean oil; 20% Water |
| $W_{20}5EC$ | 5% TWEEN 20; 8% Ethanol; 1% Cetylpyridinium Chloride; 64% Soybean oil; 22% Water |
| EC | 1% Cetylpyridinium Chloride; 8% Ethanol; 64% Soybean oil; 27% Water |
| Y3EC | 3% TYLOXAPOL; 1% Cetylpyridinium Chloride; 8% Ethanol; 64% Soybean oil; 24% Water |
| X4E | 4% TRITON X-100; 8% Ethanol; 64% Soybean oil; 24% Water |

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious against microbes and is also non-irritating and non-toxic to mammalian users (and thus be contacted with mucosal membranes).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

The following description provides a number of exemplary emulsions including formulations for compositions X8P and $X_8W_{60}PC$. X8P comprises a water-in-oil nanoemulsion, in which the oil phase was made from soybean oil, tri-n-butyl phosphate, and TRITON X-100 in 80% water. $X_8W_{60}PC$ comprises a mixture of equal volumes of X8P with $W_{80}8P$. $W_{80}8P$ is a liposome-like compound made of glycerol monostearate, refined soya sterols (e.g., GENEROL sterols). TWEEN 60, soybean oil, a cationic ion halogen-containing CPC peppermint oil. The GENEROL family are a group of a polyethoxylated soya sterols (Henkel Corporation, Ambler, Pa.). Emulsion formulations are given in Table 1 for certain embodiments of the present invention. These particular formulations may be found in U.S. Pat. No. 5,700,679 (NN); U.S. Pat. Nos. 5,618,840; 5,549,901 ($W_{80}8P$); and U.S. Pat. No. 5,547,677, herein incorporated by reference in their entireties.

The $X8W_{60}PC$ emulsion is manufactured by first making the $W_{80}8P$ emulsion and X8P emulsions separately. A mixture of these two emulsion is then re-emulsified to produce a fresh emulsion composition termed $X8W_{60}PC$. Methods of producing such emulsions are described in U.S. Pat. Nos. 5,103,497 and 4,895,452 (herein incorporated by reference in their entireties). These compounds have broad-spectrum antimicrobial activity, and are able to inactivate vegetative bacteria through membrane disruption.

The compositions listed above are only exemplary and those of skill in the art will be able to alter the amounts of the components to arrive at a nanoemulsion composition suitable for the purpose of the present invention. Those skilled in the art will understand that the ratio of oil phase to water as well as the individual oil carrier, surfactant CPC and organic phosphate buffer, components of each composition may vary.

Although certain compositions comprising X8P have a water to oil ratio of 4:1, it is understood that the X8P may be formulated to have more or less of a water phase. For example, in some embodiments, there is 3, 4, 5, 6, 7, 8, 9, 10, or more parts of the water phase to each part of the oil phase. The same holds true for the $W_{80}8P$ formulation. Similarly, the ratio of Tri(N-butyl)phosphate:TRITON X-100:soybean oil may be varied.

Although Table 1 lists specific amounts of glycerol monooleate, polysorbate 60, GENEROL 122, cetylpyridinium chloride, and carrier oil for $W_{80}8P$, these are merely exemplary. An emulsion that has the properties of $W_{80}8P$ may be formulated that has different concentrations of each of these components or indeed different components that will fulfill the same function. For example, the emulsion may have between about 80 to about 100 g of glycerol monooleate in the initial oil phase. In other embodiments, the emulsion may have between about 15 to about 30 g polysorbate 60 in the initial oil phase. In yet another embodiment the composition may comprise between about 20 to about 30 g of a GENEROL sterol, in the initial oil phase.

The nanoemulsions structure of the certain embodiments of the emulsions of the present invention may play a role in their biocidal activity as well as contributing to the non-toxicity of these emulsions. For example, the active component in X8P, TRITON-X100 shows less biocidal activity against virus at concentrations equivalent to 11% X8P. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. It should be noted that when all the components of X8P are combined in one composition but are not in a nanoemulsion structure, the mixture is not as effective as an antimicrobial as when the components are in a nanoemulsion structure.

Numerous additional embodiments presented in classes of formulations with like compositions are presented below. The effect of a number of these compositions as antipathogenic materials is provided in FIG. 9. The following compositions recite various ratios and mixtures of active components. One skilled in the art will appreciate that the below recited formulation are exemplary and that additional formulations comprising similar percent ranges of the recited components are within the scope of the present invention.

In certain embodiments of the present invention, the inventive formulation comprise from about 3 to 8% of TYLOXAPOL, about 8 vol. % of ethanol, about 1 vol. % of cetylpyridinium chloride (CPC), about 60 to 70 vol. % (e.g., soybean oil), about 15 to 25 vol. % of aqueous phase (e.g., $DiH_2O$ or PBS), and in some formulations less than about 1 vol. % of 1N NaOH. Some of these embodiments comprise PBS. It is contemplated that the addition of 1N NaOH and/or PBS in some of these embodiments, allows the user to advantageously control the pH of the formulations, such that pH ranges from about 4.0 to about 10.0, and more preferably from about 7.1 to 8.5 are achieved. For example, one embodiment of the present invention comprises about 3 vol. % of TYLOXAPOL, about 8 vol. % of ethanol, about 1 vol. % of CPC, about 64 vol. % of soybean oil, and about 24 vol. % of $DiH_2O$ (designated herein as Y3EC). Another similar embodiment comprises about 3.5 vol. % of TYLOXAPOL, about 8 vol. % of ethanol, and about 1 vol. % of CPC, about 64 vol. % of soybean oil, and about 23.5 vol. % of $DiH_2O$ (designated herein as Y3.5EC). Yet another embodiment comprises about 3 vol. % of TYLOXAPOL, about 8 vol. % of ethanol, about 1 vol. % of CPC, about 0.067 vol. % of 1N NaOH, such that the pH of the formulation is about 7.1, about 64 vol. % of soybean oil, and about 23.93 vol. % of $DiH_2O$ (designated herein as Y3EC pH 7.1). Still another embodiment comprises about 3 vol. % of TYLOXAPOL, about 8 vol. % of ethanol, about 1 vol. % of CPC, about 0.67 vol. % of 1N NaOH, such that the pH of the formulation is about 8.5, and about 64 vol. % of soybean oil, and about 23.33 vol. % of $DiH_2O$ (designated herein as Y3EC pH 8.5). Another similar embodiment comprises about 4% TYLOXAPOL, about 8 vol. % ethanol, about 1% CPC, and about 64 vol. % of soybean oil, and about 23 vol. % of $DiH_2O$ (designated herein as Y4EC). In still another embodiment the formulation comprises about 8% TYLOXAPOL, about 8% ethanol, about 1 vol. % of CPC, and about 64 vol. % of soybean oil, and about 19 vol. % of $DiH_2O$ (designated herein as Y8EC). A further embodiment comprises about 8 vol. % of TYLOXAPOL, about 8 vol. % of ethanol, about 1 vol. % of CPC, about 64 vol. % of soybean oil, and about 19 vol. % of 1× PBS (designated herein as Y8EC PBS).

In some embodiments of the present invention, the inventive formulations comprise about 8 vol. % of ethanol, and about 1 vol. % of CPC, and about 64 vol. % of oil (e.g., soybean oil), and about 27 vol. % of aqueous phase (e.g., $DiH_2O$ or PBS) (designated herein as EC).

In the present invention, some embodiments comprise from about 8 vol. % of sodium dodecyl sulfate (SDS), about 8 vol. % of tributyl phosphate (TBP), and about 64 vol. % of oil (e.g., soybean oil), and about 20 vol. % of aqueous phase (e.g., $DiH_2O$ or PBS) (designated herein as S8P).

In certain embodiments of the present invention, the inventive formulation comprise from about 1 to 2 vol. % of TRITON X-100, from about 1 to 2 vol. % of TYLOXAPOL, from about 7 to 8 vol. % of ethanol, about 1 vol. % of cetylpyridinium chloride (CPC), about 64 to 57.6 vol. % of oil (e.g., soybean oil), and about 23 vol. % of aqueous phase (e.g., $DiH_2O$ or PBS). Additionally, some of these formulations further comprise about 5 mM of L-alanine/Inosine, and about 10 mM ammonium chloride. Some of these formulations comprise PBS. It is contemplated that the addition of PBS in some of these embodiments, allows the user to advantageously control the pH of the formulations. For example, one embodiment of the present invention comprises about 2 vol. % of TRITON X-100, about 2 vol. % of TYLOXAPOL, about 8 vol. % of ethanol, about 1 vol. % CPC, about 64 vol. % of soybean oil, and about 23 vol. % of aqueous phase $DiH_2O$. In another embodiment the formulation comprises about 1.8 vol. % of TRITON X-100, about 1.8 vol. % of TYLOXAPOL, about 7.2 vol. % of ethanol, about 0.9 vol. % of CPC, about 5 mM L-alanine/Inosine, and about 10 mM ammonium chloride, about 57.6 vol. % of soybean oil, and the remainder of 1× PBS (designated herein as 90% X2Y2EC/GE).

In alternative embodiments of the present invention, the formulations comprise from about 5 vol. % of TWEEN 80, from about 8 vol. % of ethanol, from about 1 vol. % of CPC, about 64 vol. % of oil (e.g., soybean oil), and about 22 vol. % of DiH$_2$O (designated herein as W$_{80}$5FC).

In still other embodiments of the present invention, the formulations comprise from about 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC).

In still other embodiments of the present invention, the formulations comprise from about 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC).

In still other embodiments of the present invention, the formulations comprise from about 2 to 8 vol. % of TRITON X-100, about 8 vol. % of ethanol, about 1 vol. % of CPC, about 60 to 70 vol. % of oil (e.g., soybean, or olive oil), and about 15 to 25 vol. % of aqueous phase (e.g., DiH$_2$O or PBS). For example, the present invention contemplates formulations comprising about 2 vol. % of TRITON X-100, about 8 vol. % of ethanol, about 64 vol. % of soybean oil, and about 26 vol. % of DiH$_2$O (designated herein as X2E). In other similar embodiments, the formulations comprise about 3 vol. % of TRITON X-100, about 8 vol. % of ethanol, about 64 vol. % of soybean oil, and about 25 vol. % of DiH$_2$O (designated herein as X3E). In still further embodiments, the formulations comprise about 4 vol. % TRITON X-100, about 8 vol. % of ethanol, about 64 vol. % of soybean oil, and about 24 vol. % of DiH$_2$O (designated herein as X4E). In yet other embodiments, the formulations comprise about 5 vol. % of TRITON X-100, about 8 vol. % of ethanol, about 64 vol. % of soybean oil, and about 23 vol. % of DiH$_2$O (designated herein as X5E). Another embodiment of the present invention comprises about 6 vol. % of TRITON X-100, about 8 vol. % of ethanol, about 64 vol. % of soybean oil, and about 22 vol. % of DiH$_2$O (designated herein as X6E). In still further embodiments of the present invention, the formulations comprise about 8 vol. % of TRITON X-100, about 8 vol. % of ethanol, about 64 vol. % of soybean oil, and about 20 vol. % of DiH$_2$O (designated herein as X8E). In still further embodiments of the present invention, the formulations comprise about 8 vol. % of TRITON X-100, about 8 vol. % of ethanol, about 64 vol. % of olive oil, and about 20 vol. % of DiH$_2$O (designated herein as X8E O). In yet another embodiment comprises 8 vol. % of TRITON X-100, about 8 vol. % ethanol, about 1 vol. % CPC, about 64 vol. % of soybean oil, and about 19 vol. % of DiH$_2$O (designated herein as X8EC).

In alternative embodiments of the present invention, the formulations comprise from about 1 to 2 vol. % of TRITON X-100, from about 1 to 2 vol. % of TYLOXAPOL, from about 6 to 8 vol. % TBP, from about 0.5 to 1.0 vol. % of CPC, from about 60 to 70 vol. % of oil (e.g., soybean), and about 1 to 35 vol. % of aqueous phase (e.g., DiH$_2$O or PBS). Additionally, certain of these formulations may comprise from about 1 to 5 vol. % of trypticase soy broth, from about 0.5 to 1.5 vol. % of yeast extract, about 5 mM L-alanine/Inosine, about 10 mM ammonium chloride, and from about 20-40 vol. % of liquid baby formula. In some of the embodiments comprising liquid baby formula, the formula comprises a casein hydrolysate (e.g., Neutramigen, or Progestimil, and the like). In some of these embodiments, the inventive formulations further comprise from about 0.1 to 1.0 vol. % of sodium thiosulfate, and from about 0.1 to 1.0 vol. % of sodium citrate. Other similar embodiments comprising these basic components employ phosphate buffered saline (PBS) as the aqueous phase. For example, one embodiment comprises about 2 vol. % of TRITON X-100, about 2 vol. % TYLOXAPOL, about 8 vol. % TBP, about 1 vol. % of CPC, about 64 vol. % of soybean oil, and about 23 vol. % of DiH$_2$O (designated herein as X2Y2EC). In still other embodiments, the inventive formulation comprises about 2 vol. % of TRITON X-100, about 2 vol. % TYLOXAPOL, about 8 vol. % TBP, about 1 vol. % of CPC, about 0.9 vol. % of sodium thiosulfate, about 0.1 vol. % of sodium citrate, about 64 vol. % of soybean oil, and about 22 vol. % of DiH$_2$O (designated herein as X2Y2PC STS1). In another similar embodiment, the formulations comprise about 1.7 vol. % TRITON X-100, about 1.7 vol. % TYLOXAPOL, about 6.8 vol. % TBP, about 0.85% CPC, about 29.2% NEUTRAMIGEN, about 54.4 vol. % of soybean oil, and about 4.9 vol. % of DiH$_2$O (designated herein as 85% X2Y2PC/baby). In yet another embodiment of the present invention, the formulations comprise about 18 vol. % of TRITON X-100, about 1.8 vol. % of TYLOXAPOL, about 7.2 vol. % of TBP, about 0.9 vol. % of CPC, about 5 mM L-alanine/nosine, about 10 mM ammonium chloride, about 57.6 vol. % of soybean oil, and the remainder vol. % of 0.1× PBS (designated herein as 90% X2Y2PC/GE). In still embodiment, the formulations comprise about 1.8 vol. % of TRITON X-100, about 1.8 vol. % of TYLOXAPOL, about 7.2 vol. % of TBP, about 0.9 vol. % of CPC, and about 3 vol. % trypticase soy broth, about 57.6 vol. % of soybean oil, and about 27.7 vol. % of DiH$_2$O (designated herein as 90% X2Y2PC/TSB). In another embodiment of the present invention, the formulations comprise about 1.8 vol. % TRITON X-100, about 1.8 vol. % TYLOXAPOL, about 7.2 vol. % TBP, about 0.9 vol. % CPC, about 1 vol. % yeast extract, about 57.6 vol. % of soybean oil, and about 29.7 vol. % of DiH$_2$O (designated herein as 90% X2Y2PC/YE).

In some embodiments of the present invention, the inventive formulations comprise about 3 vol. % of TYLOXAPOL, about 8 vol. % of TBP, and about 1 vol. % of CPC, about 60 to 70 vol. % of oil (e.g., soybean or olive oil), and about 15 to 30 vol. % of aqueous phase (e.g., DiH$_2$O or PBS). In a particular embodiment of the present invention, the inventive formulations comprise about 3 vol. % of TYLOXAPOL, about 8 vol. % of TBP, and about 1 vol. % of CPC, about 64 vol. % of soybean, and about 24 vol. % of DiH$_2$O (designated herein as Y3PC).

In some embodiments of the present invention, the inventive formulations comprise from about 4 to 8 vol. % of TRITON X-100, from about 5 to 8 vol. % of TBP, about 30 to 70 vol. % of oil (e.g., soybean or olive oil), and about 0 to 30 vol. % of aqueous phase (e.g., DiH$_2$O or PBS). Additionally, certain of these embodiments further comprise about 1 vol. % of CPC, about 1 vol. % of benzalkonium chloride, about 1 vol. % cetylyridinium bromide, about 1 vol. % cetyldimethyletylammonium bromide, 500 µM EDTA, about 10 mM ammonium chloride, about 5 mM inosine, and about 5 mM L-alanine. For example, in certain of these embodiments, the inventive formulations comprise about 8 vol. % of TRITON X-100, about 8 vol. % of TBP, about 64 vol. % of soybean oil, and about 20 vol. % of DiH$_2$O (designated herein as X8P). In another embodiment of the present invention, the inventive formulations comprise about 8 vol. % of TRITON X-100, about 8 vol. % of TBP, about 1% of CPC, about 64 vol. % of soybean oil, and about 19 vol. % of DiH$_2$O (designated herein as X8PC). In still another embodiment, the formulations comprise about 8 vol. % TRITON X-100, about 8 vol. % of TBP, about 1 vol. % of CPC, about 50 vol. % of soybean oil, and about 33 vol. % of DiH$_2$O (designated herein as ATB-X1001). In yet another embodiment, the formulations comprise about 8 vol. % of TRITON X-100, about 8 vol. % of TBP, about 2 vol. % of CPC, about 50 vol. % of soybean oil, and about 32 vol. % of DiH$_2$O (designated herein as ATB-X002). Another embodiment of the present invention comprises about 4 vol. % TRITON X-100, about 4 vol. % of TBP, about 0.5 vol. % of CPC, about 32 vol. % of soybean oil, and about 59.5 vol. % of DiH$_2$O (designated herein as 50% X8PC). Still another related embodiment comprises about 8 vol. % of TRITON X-100, about 8 vol. % of TBP, about 0.5 vol. % CPC, about 64 vol. % of soybean oil, and about 19.5 vol. % of DiH$_2$O (designated herein as X8PC$_{1/2}$). In some embodiments of the present invention, the inventive formulations comprise about 8 vol. % of TRITON X-100, about vol. % of TBP, about 2 vol. % of CPC, about 64 vol. % of soybean oil, and about 18 vol. % of DiH$_2$O (designated herein as X8PC2). In other embodiments, the inventive formulations comprise about 8 vol. % of TRITON X-100, about 8% of TBP, about 1% of benzalkonium chloride, about 50 vol. % of soybean oil, and about 33 vol. % of DiH$_2$O (designated herein as X8P BC). In an alternative embodiment of the present invention, the formulation comprise about 8 vol. % of TRITON X-100, about 8 vol. % of TBP, about 1 vol. % of cetylridinium bromide, about 50 vol. % of soybean oil, and about 33 vol. % of DiH$_2$O (designated herein as X8P CPB). In another exemplary embodiment of the present invention, the formulations comprise about 8 vol. % of TRITON X-100, about 8 vol. % of TBP, about 1 vol. % of cetylyridinium bromide, about 50 vol. % of soybean oil, and about 33 vol. % of DiH$_2$O (designated herein as X8P CPB). In another exemplary embodiment of the present invention, the formulations comprise about 8 vol. % of TRITON X-100, about 8 vol. % of TBP, about 1 vol. % of cetyldimethyletylammonium bromide, about 50 vol. % of soybean oil, and about 33 vol. % of DiH$_2$O (designated herein as X8P CTAB). In still further embodiments, the present invention comprises about 8 vol. % of TRITON X-100, about 8 vol. % of TBP, about 1 vol. % of CPC, about 500 µM EDTA, about 64 vol. % of soybean oil, and about 15.8 vol. % DiH$_2$O (designated herein as X8PC EDTA). Additional similar embodiments comprise 8 vol. % of TRITON X-100, about 8 vol. % of TBP, about 1 vol. % of CPC, about 10 mM ammonium chloride, about 5 mM Inosine, about 5 mM L-alanine, about 64 vol. % of soybean oil, and about 19 vol. % of DiH$_2$O or PBS (designated herein as X8PC GE$_{1x}$). In another embodiment of the present invention, the inventive formulations further comprise about 5 vol. % of TRITON X-100, about 5% of TBP, about 1 vol. % of CPC, about 40 vol. % of soybean oil, and about 49 vol. % of DiH$_2$O (designated herein as X5P$_5$C).

In some embodiments of the present invention, the inventive formulations comprise about 2 vol. % TRITON X-100, about 6 vol. % TYLOXAPOL, about 8 vol. % ethanol, about 64 vol. % of soybean oil, and about 20 vol. % of DiH$_2$O (designated herein as X2Y6E).

In an additional embodiment of the present invention, the formulations comprise about 8 vol. % of TRITON X-100, and about 8 vol. % of glycerol, about 60 to 70 vol. % of oil (e.g., soybean or olive oil), and about 15 to 25 vol. % of aqueous phase (e.g., DiH$_2$O or PBS). Certain related embodiments further comprise about 1 vol. % L-ascorbic acid. For example, one particular embodiment comprises about 8 vol. % of TRITON X-100, about 8 vol. % of glycerol, about 64 vol. % of soybean oil, and about 20 vol. % of DiH$_2$O (designated herein as X8G). In still another embodiment, the inventive formulations comprise about 8 vol. % of TRITON X-100, about 8 vol. % of glycerol, about 1 vol. % of L-ascorbic acid, about 64 vol. % of soybean oil, and about 19 vol. % of DiH$_2$O (designated herein as X8GV$_c$).

In still further embodiments, the inventive formulations comprise about 8 vol. % of TRITON X-100, from about 0.5 to 0.8 vol. % of TWEEN 60, from about 0.5 to 2.0 vol. % of CPC, about 8 vol. % of TBP, about 60 to 70 vol. % of oil (e.g., soybean or olive oil), and about 15 to 25 vol. % of aqueous phase (e.g., DiH$_2$O or PBS). For example, in one particular embodiment the formulations comprise about 8 vol. % of TRITON X-100, about 0.70 vol. % of TWEEN 60, about 1 vol. % of CPC, about 8 vol. % of TBP, about 64 vol. % of soybean oil, and about 18.3 vol. % of DiH$_2$O (designated herein as X8W60PC$_1$). Another related embodiment comprises about 8 vol. % of TRITON X-100, about 0.71 vol. % of TWEEN 60, about 1 vol. % of CPC, about 8 vol. % of TBP, about 64 vol. % of soybean oil, and about 18.29 vol. % of DiH$_2$O (designated herein as W60$_{0.7}$X8PC). In yet other embodiments, the inventive formulations comprise from about 8 vol. % of TRITON X-100, about 0.7 vol. % of TWEEN 60, about 0.5 vol. % of CPC, about 8 vol. % of TBP, about 64 to 70 vol. % of soybean oil, and about 18.8 vol. % of DiH$_2$O (designated herein as X8W60PC$_2$). In still other embodiments, the present invention comprises about 8 vol. % of TRITON X-100, about 0.71 vol. % of TWEEN 60, about 2 vol. % of CPC, about 8 vol. % of TBP, about 64 vol. % of soybean oil, and about 17.3 vol. % of DiH$_2$O. In another embodiment of the present invention, the formulations comprise about 0.71 vol. % of TWEEN 60, about 1 vol. % of CPC, about 8 vol. % of TBP, about 64 vol. % of soybean oil, and about 25.29 vol. % of DiH$_2$O (designated herein as W60$_{0.7}$PC).

In another embodiment of the present invention, the inventive formulations comprise about 2 vol. % of dioctyl sulfosuccinate, either about 8 vol. % of glycerol, or about 8 vol. % TBP, in addition to, about 60 to 70 vol. % of oil (e.g., soybean or olive oil), and about 20 to 30 vol. % of aqueous phase (e.g., DiH$_2$O or PBS). For example, one embodiment of the present invention comprises about 2 vol. % of dioctyl sulfosuccinate, about 8 vol. % of glycerol, about 64 vol. % of soybean oil, and about 26 vol. % of DiH$_2$O (designated herein as D2G). In another related embodiment, the inventive formulations comprise about 2 vol. % of dioctyl sulfosuccinate, and about 8 vol. % of TBP, about 64 vol. % of soybean oil, and about 26 vol. % of DiH$_2$O (designated herein as D2P).

In still other embodiments of the present invention, the inventive formulations comprise about 8 to 20 vol. % of glycerol, and about 1 to 10 vol. % of CPC, about 50 to 70 vol. % of oil (e.g., soybean or olive oil), and about 15 to 30 vol. % of aqueous phase (e.g., DiH$_2$O or PBS). Additionally, in certain of these embodiments, the compositions further comprise about 1 vol. % of L-ascorbic acid. For example, one particular embodiment comprises about 8 vol. % of glycerol, about 1 vol. % of CPC, about 64 vol. % of soybean oil, and about 27 vol. % of DiH$_2$O (designated herein as GC). An additional related embodiment comprises about 10 vol. % of glycerol, about 10 vol. % of CPC, about 60 vol. % of soybean oil, and about 20 vol. % of DiH$_2$O (designated herein as GC10). In still another embodiment of the present invention, the inventive formulations comprise about 10 vol. % of glycerol, about 1 vol. % of CPC, about 1 vol. % of L-ascorbic acid, about 64 vol. % of soybean or oil, and about 24 vol. % of DiH$_2$O (designated herein as GCV$_c$).

In some embodiments of the present invention, the inventive formulations comprise about 8 to 10 vol. % of glycerol, about 8 to 10 vol. % of SDS, about 50 to 70 vol. % of oil (e.g., soybean or olive oil), and about 15 to 30 vol. % of aqueous phase (e.g., DiH$_2$O or PBS). Additionally, in certain of these embodiments, the compositions further comprise about 1 vol. % of lecithin, and about 1 vol. % of p-Hydroxybenzoic acid methyl ester. Exemplary embodiments of such formulations comprise about 8 vol. % SDS, 8 vol. % of glycerol, about 64 vol. % of soybean oil, and about 20 vol. % of DiH$_2$O (designated herein as S8G). A related formulation comprises about 8 vol. % of glycerol, about 8 vol. % of SDS, about 1 vol. % of lecithin, about 1 vol. % of p-Hydroxybenzoic acid methyl ester, about 64 vol. % of soybean oil, and about 18 vol. % of DiH$_2$O (designated herein as S8GL1B1).

In yet another embodiment of the present invention, the inventive formulations comprise about 4 vol. % of TWEEN 80, about 4 vol. % of TYLOXAPOL, about 1 vol. % of CPC, about 8 vol. % of ethanol, about 64 vol. % of soybean oil, and about 19 vol. % of DiH$_2$O (designated herein as W$_{80}$4Y4EC).

In some embodiments of the present invention, the inventive formulations comprise about 0.01 vol. % of CPC, about 0.08 vol. % of TYLOXAPOL, about 10 vol. % of ethanol, about 70 vol. % of soybean oil, and about 19.91 vol. % of DiH$_2$O (designated herein as Y.08EC.01).

In yet another embodiment of the present invention, the inventive formulations comprise about 8 vol. % of sodium laurly sulfate, and about 8 vol. % of glycerol, about 64 vol. % of soybean oil, and about 20 vol. % of DiH$_2$O (designated herein as SLS8G).

The specific formulations described above are simply examples to illustrate the variety of compositions that find use in the present invention. The present invention contemplates that many variations of the above formulation, as well as additional nanoemulsions, find use in the methods of the present invention. To determine if a candidate emulsion is suitable for use with the present invention, three criteria may be analyzed. Using the methods and standards described herein, candidate emulsions can be easily tested to determine if they are suitable. First, the desired ingredients are prepared using the methods described herein, to determine if an emulsion can be formed. If an emulsion cannot be formed, the candidate is rejected. For example, a candidate composition made of 4.5% sodium thiosulfate, 0.5% sodium citrate, 10% n-butanol, 64% soybean oil, and 21% DiH$_2$O did not form an emulsion.

Second, in preferred embodiments, the candidate emulsion should form a stable emulsion. An emulsion is stable if it remains in emulsion form for a sufficient period to allow its intended use. For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% TWEEN 10, 1% CPC, 64% soybean oil, and 22% DiH$_2$O did not form a stable emulsion. The following candidate emulsions were shown to be stable using the methods described herein: 0.08% TRITON X-100, 0.08% Glycerol, 0.01% Cetylpyridinium Chloride, 99% Butter, and 0.83% diH$_2$O (designated herein as 1% X8GC Butter); 0.8% TRITON X-100, 0.8% Glycerol, 0.1% Cetylpyridinium Chloride, 6.4% Soybean Oil, 1.9% diH$_2$O, and 90% Butter (designated herein as 10% X8GC Butter); 2% W$_{20}$5EC, 1% Natrosol 250L NF, and 97% diH$_2$O (designated herein as 2% W$_{20}$5EC L GEL); 1% Cetylpyridinium Chloride, 5% TWEEN 20, 8% Ethanol, 64% 70 Viscosity Mineral Oil, and 22% DiH$_2$O (designated herein as W$_{20}$5EC 70 Mineral Oil); 1% Cetylpyridinium Chloride, 5% TWEEN 20, 8% Ethanol, 64% 350 Viscosity Mineral Oil, and 22% DiH$_2$O (designated herein as W$_{20}$5EC 350 Mineral Oil).

Third, the candidate emulsion should have efficacy for its intended use. For example, an anti-bacterial emulsion should kill or disable pathogens to a detectable level. As shown herein, certain emulsions of the present invention have efficacy against specific microorganisms, but not against other. Using the methods described herein, one is capable of determining the suitability of a particular candidate emulsion against the desired microorganism. Generally, this involves exposing the microorganism to the emulsion for one or more time periods in a side-by-side experiment with the appropriate control samples (e.g., a negative control such as water) and determining if, and to what degree, the emulsion kills or disables the microorganism. For example, a candidate composition made of 1% ammonium chloride, 5% TWEEN 20, 8% ethanol, 64% soybean oil, and 22% DiH$_2$O was shown not to be an effective emulsion. The following candidate emulsions were shown to be effective using the methods described herein: 5% TWEEN 20, 5% Cetylpyridinium Chloride, 10% Glycerol, 60% Soybean Oil, and 20% DiH$_2$O (designated herein as W$_{20}$5GC5); 1% Cetylpyridinium Chloride, 5% TWEEN 20, 10% Glycerol, 64% Soybean Oil, and 20% diH$_2$O (designated herein as W$_{20}$5GC); 1% Cetylpyridinium Chloride, 5% TWEEN 20, 8% Ethanol, 64% Olive Oil, and 22% diH$_2$O (designated herein as W$_{20}$5EC Olive Oil); 1% Cetylpyridinium Chloride, 5% TWEEN 20, 8% Ethanol, 64% Flaxeed Oil, and 22% DiH$_2$O (designated herein as W$_{20}$5EC Flaxeed Oil); 1% Cetylpyridinium Chloride, 5% TWEEN 20, 8% Ethanol, 64% Corn Oil, and 22% diH$_2$O (designated herein as W$_{20}$5EC Corn Oil); 1% Cetylpyridinium Chloride, 5% TWEEN 20, 8% Ethanol, 64% Coconut Oil, and 22% diH$_2$O (designated herein as W$_{20}$5EC Coconut Oil); 1% Cetylpyridinium Chloride, 5% TWEEN 20, 8% Ethanol, 64% Cottonseed Oil, and 22% diH$_2$O (designated herein as W$_{20}$5EC Cottonseed Oil); 8% Dextrose, 5% TWEEN 10, 1% Cetylpyridinium Chloride, 64% Soybean Oil, and 22% diH$_2$O (designated herein as W$_{20}$5C Dextrose); 8% PEG 200, 5% TWEEN 10, 1% Cetylpyridinium Chloride, 64% Soybean Oil, and 22% diH$_2$O (designated herein as W$_{20}$5C PEG 200); 8% Methanol, 5% TWEEN 10, 1% Cetylpyridinium Chloride, 64% Soybean Oil, and 22% diH$_2$O (designated herein as W$_{20}$5C Methanol); 8% PEG 1000, 5% TWEEN 10, 1% Cetylpyridinium Chloride, 64% Soybean Oil, and 22% diH$_2$O (designated herein as W$_{20}$5C PEG 1000); 2% W$_{20}$5EC, 2% Natrosol 250H NF, and 96% diH$_2$O (designated herein as 2% W$_{20}$5EC Natrosol 2, also called 2% W$_{20}$5EC GEL); 2% W$_{20}$5EC, 1% Natrosol 250H NF, and 97% diH$_2$O (designated herein as 2% W$_{20}$5EC Natrosol 1); 2% W$_{20}$5EC, 3% Natrosol 250H NF, and 95% diH$_2$O (designated herein as 2% W$_{20}$5EC Natrosol 3); 2% W$_{20}$5EC, 0.5% Natrosol 250H NF, and 97.5% diH$_2$O (designated herein as 2% W$_{20}$5EC Natrosol 0.5); 2% W$_{20}$5EC, 2% Methocel A, and 96% diH$_2$O (designated herein as 2% W$_{20}$5EC Methocel A); 2% W$_{20}$5EC, 2% Methocel K, and 96% diH$_2$O (designated herein as 2% W$_{20}$5EC Methocel K); 2% Natrosol, 0.1% X8PC, 0.1×PBX, 5 mM L-alanine, 5mM Inosine, 10 mM Ammonium Chloride, and diH$_2$O (designated herein as 0.1% X8PC/GE+2% Natrosol); 2% Natrosol, 0.8% TRITON X-100, 0.8% Tributyl Phosphate, 6.4% Soybean Oil, 0.1% Cetylpyridinium Chloride, 0.1× PBS, 5mM L-alanine, 5mM Inosine, 10 mM Ammonium Chloride, and diH$_2$O (designated herein as 10% X8PC/GE+2% Natrosol); 1% Cetylpyridinium Chloride, 5% TWEEN 20, 8% Ethanol, 64% Lard, and 22% diH$_2$O (designated herein as W$_{20}$5EC Lard); 1% Cetylpyridinium Chloride, 5% TWEEN 20, 8% Ethanol, 64% Mineral Oil, and 22% diH$_2$O (designated herein as W$_{20}$5EC Mineral Oil); 0.1% Cetylpyridinium Chloride, 2% Nerolidol, 5% TWEEN 20, 10% Ethanol, 64% Soybean Oil, and 18.9% diH$_2$O (designated herein as W$_{20}$5EC$_{0.1}$N); 0.1% Cetylpyridinium Chloride, 2% Farnesol, 5% TWEEN 20, 10% Ethanol, 64% Soybean Oil, and 18.9% diH$_2$O (designated herein as W$_{20}$5EC$_{0.1}$F); 0.1% Cetylpyridinium Chloride, 5% TWEEN 20, 10% Ethanol, 64% Soybean Oil, and 20.9% diH$_2$O (designated herein as W$_{20}$5EC$_{0.1}$); 10% Cetylpyridinium Chloride, 8% Tributyl Phosphate, 8% TRITON X-100, 54% Soybean Oil, and 20% diH$_2$O (designated herein as X8PC$_{10}$); 5% Cetylpyridinium Chloride, 8% TRITON X-100, 8% Tributyl Phosphate, 59% Soybean Oil, and 20% diH$_2$O (designated herein as X8PC$_5$); 0.02% Cetylpyridinium Chloride, 0.1% TWEEN 20, 10% Ethanol, 70% Soybean Oil, and 19.88% diH$_2$O (designated herein as W$_{20}$0.1EC$_{0.02}$); 1% Cetylpyridinium Chloride, 5% TWEEN 20.8% Glycerol, 64% Mobil 1, and 22% diH$_2$O (designated herein as W$_{20}$5GC Mobil 1); 7.2% TRITON X-100, 7.2% Tributyl Phosphate, 0.9% Cetylpyridinium Chloride, 57.6% Soybean Oil, 0.1× PBS, 5 mM L-alanine, 5 mM Inosine, 10 mM Ammonium Chloride, and 25.87% diH$_2$O (designated herein as 90% X8PC/GE); 7.2% TRITON X-100, 7.2% Tributyl Phosphate, 0.9% Cetylpyridinium Chloride, 57.6% Soybean Oil, 1% EDTA, 5 mM L-alanine, 5 mM Inosine, 10 mM Ammonium Chloride, 0.1× PBS, and diH$_2$O (designated herein as 90% X8PC/GE EDTA); and 7.2% TRITON X-100, 7.2% Tributyl Phosphate, 0.9% Cetylpyridinium Chloride, 57.6% Soybean Oil, 1% Sodium Thiosulfate, 5 mM, L-alanine, 5 mM Inosine, 10 mM Ammonium Chloride, 0.1× PBS, and diH$_2$O (designated herein as 90% X8PC/GE STS).

1. Aqueous Phase

In some embodiments, the emulsion comprises an aqueous phase. In certain preferred embodiments, the emulsion comprises about 5 to 50, preferably 10 to 40, more preferably 15 to 30, vol. % aqueous phase, based on the total volume of the emulsion (although other concentrations are also contemplated). In preferred embodiments, the aqueous phase comprises water at a pH of about 4 to 10, preferably about 6 to 8. The water is preferably deionized (hereinafter "DiH$_2$O"). In some embodiments, the aqueous phase comprises phosphate buffered saline (PBS). In some preferred embodiments, the aqueous phase is sterile and pyrogen free.

2. Oil Phase

In some embodiments, the emulsion comprises an oil phase. In certain preferred embodiments, the oil phase (e.g., carrier oil) of the emulsion of the present invention comprises 30-90, preferably 60-80, and more preferably 60-70, vol. % of oil, based on the total volume of the emulsion (although other concentrations are also contemplated). Suitable oils include, but are not limited to, soybean oil, avocado oil, squalene oil, squalene oil, olive oil, canola oil, corn oil, rapeseed oil, safflower oil, sunflower oil, fish oils, flavor oils, water insoluble vitamins and mixtures thereof. In particularly preferred embodiments, soybean oil is used. In preferred embodiments of the present invention, the oil phase is preferably distributed throughout the aqueous phase as droplets having a mean particle size in the range from about 1-2 microns, more preferably from 0.2 to 0.8, and most preferably about 0.8 microns. In other embodiments, the aqueous phase can be distributed in the oil phase.

In some embodiments, the oil phase comprises 3-15, and preferably 5-10 vol. % of an organic solvent, based on the total volume of the emulsion. While the present invention is not limited to any particular mechanism, it is contemplated that the organic phosphate-based solvents employed in the emulsions serve to remove or disrupt the lipids in the membranes of the pathogens. Thus, any solvent that removes the sterols or phospholipids in the microbial membranes finds use in the methods of the present invention. Suitable organic solvents include, but are not limited to, organic phosphate based solvents or alcohols. In some preferred embodiments, non-toxic alcohols (e.g., ethanol) are used as a solvent. The oil phase, and any additional compounds provided in the oil phase, are preferably sterile and pyrogen free.

3. Surfactants and Detergents

In some embodiments, the emulsions further comprises a surfactant or detergent. In some preferred embodiments, the emulsion comprises from about 3 to 15%, and preferably about 10% of one or more surfactants or detergents (although other concentrations are also contemplated). While the present invention is not limited to any particular mechanism, it is contemplated that surfactants, when present in the emulsion, help to stabilize the emulsions. Both non-ionic (non-anionic) and ionic surfactants are contemplated. Additionally, surfactants from the BRIJ family of surfactants find use in the compositions of the present invention. The surfactant can be provided in either the aqueous or the oil phase. Surfactants suitable for use with the emulsions include a variety of anionic and nonionic surfactants, as well as other emulsifying compounds that are capable of promoting the formation of oil-in-water emulsions. In general, emulsifying compounds are relatively hydrophilic, and blends of emulsifying compounds can be used to achieve the necessary qualities. In some formulations, nonionic surfactants have advantages over ionic emulsifiers in that they are substantially more compatible with a broad pH range and often form more stable emulsions than do ionic (e.g. soap-type) emulsifiers. Thus, in certain preferred embodiments, the compositions of the present invention comprise one or more non-ionic surfactants such as polysorbate surfactants (e.g., polyoxyethylene ethers), polysorbate detergents, pheoxypolyethoxyethanols, and the like. Examples of polysorbate detergents useful in the present invention include, but are not limited to, TWEEN 20, TWEEN 40, TWEEN 60, TWEEN 80, etc.

TWEEN 60 (polyoxyethylenesorbitan monostearate), together with TWEEN 20, TWEEN 40 and TWEEN 80, comprise polysorbates that are used as emulsifiers in a number of pharmaceutical compositions. In some embodiments of the present invention, these compounds are also used as co-components with adjuvants. TWEEN surfactants also appear to have virucidal effects on lipid-enveloped viruses (See e.g., Eriksson et al., Blood Coagulation and Fibtinolysis 5 (Suppl. 3):S37-S44[1994]).

Examples of pheoxypolyethoxyethanols, and polymers thereof, useful in the present invention include, but are not limited to, TRITON (e.g., X-100, X-301, X-165, X-102, X-200), and TYLOXAPOL. TRITON X-100 is a strong non-ionic detergent and dispersing agent widely used to extract lipids and proteins from biological structures. It also has virucidal effect against broad spectrum of enveloped viruses (See e.g., Maha and Igarashi, Southeast Asian J. Trop. Med. Pub. Health 28:718 [1997]; and Portocala et al., Virologie 27:261 [1976]). Due to this anti-viral activity, it is employed to inactivate viral pathogens in fresh frozen human plasma (See e.g., Horowitz et al., Blood 79:826 [1992]).

The present invention is not limited to the surfactants disclosed herein. Additional surfactants and detergents useful in the compositions of the present invention may be ascertained from reference works (e.g., including, but not limited to, McCutheon's Volume 1: Emulsions and Detergents—North American Edition, 2000) and commercial sources.

4. Cationic Halogens

In some embodiments, the emulsions further comprise a cationic halogen containing compound. In some preferred embodiments, the emulsion comprises from about 0.5 to 1.0 wt. % or more of a cationic halogen containing compound, based on the total weight of the emulsion (although other concentrations are also contemplated). In preferred embodiments, the cationic halogen-containing compound is preferably premixed with the oil phase, however, it should be understood that the cationic halogen-containing compound may be provided in combination with the emulsion composition in a distinct formulation. Suitable halogen containing compounds may be selected from compounds comprising chloride, fluoride, bromide and iodide ions. In preferred embodiments, suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), and cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen-containing compound is CPC, although the compositions of the present invention are not limited to formulation with any particular cationic containing compound.

5. Germination Enhancers

In other embodiments of the present invention, the nanoemulsions further comprise a germination enhancer. In some preferred embodiments, the emulsions comprise from about 1 mM to 15 mM, and more preferably from about 5 mM to 10 mM of one ore more germination enhancing compounds (although other concentrations are also contemplated). In preferred embodiments, the germination enhancing compound is provided in the aqueous phase prior to formation of the emulsion. The present invention contemplates that when germination enhancers are added to the nanoemulsion compositions, the sporicidal properties of the nanoemulsions are enhanced. The present invention further contemplates that such germination enhancers initiate sporicidal activity near neutral pH (between pH 6-8, and preferably 7). Such neutral pH emulsions can be obtained, for example, by diluting with phosphate buffer saline (PBS) or by preparations of neutral emulsions. The sporicidal activity of the nanoemulsion preferentially occurs when the spores initiate germination.

In specific embodiments, it has been demonstrated that the emulsions utilized in the vaccines of the present invention have sporicidal activity. While the present invention is not limited to any particular mechanism and an understanding of the mechanism is not required to practice the present invention, it is believed that the fusigenic component of the emulsions acts to initiate germination and before reversion to the vegetative form is complete the lysogenic component of the emulsion acts to lyse the newly germinating spore. These components of the emulsion thus act in concert to leave the spore susceptible to disruption by the emulsions. The addition of germination enhancer further facilitates the anti-sporicidal activity of the emulsions, for example, by speeding up the rate at which the sporicidal activity occurs.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine stimulates bacterial spore germination (See e.g., Hills, J. Gen. Micro. 4:38 [1950]; and Halvorson and Church, Bacteriol Rev. 21:112 [1957]). L-alanine and L-proline have also been reported to initiate fungal spore germination (Yanagita, Arch Mikrobiol 26:329 [1957]). Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate, which is the end product of glycolytic metabolism (Embden-Meyerhof-Parnas Pathway). Oxidation of pyruvate by pyruvate dehydrogenase complex yields acetyl-CoA, NADH, H$^+$, and $CO_2$. Acetyl-CoA is the initiator substrate for the tricarboxylic acid cycle (Kreb's Cycle), which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabilic activity that follows.

In certain embodiments, suitable germination enhancing agents of the invention include, but are not limited to, a α-amino acids comprising glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104; herein incorporated by reference in its entirety. In some embodiments, a mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, Inosine and $NH_4Cl$. In some embodiments, the compositions further comprise one or more common forms of growth media (e.g., trypticase soy broth, and the like) that additionally may or may not itself comprise germination enhancers and buffers.

The above compounds are merely exemplary germination enhancers and it is understood that other known germination enhancers will find use in the nanoemulsions utilized in some embodiments of the present invention. A candidate germination enhancer should meet two criteria for inclusion in the compositions of the present invention: it should be capable of being associated with the emulsion disclosed herein and it should increase the rate of germination of a target spore when incorporated in the emulsions disclosed herein. One skilled in the art can determine whether a particular agent has the desired function of acting as an germination enhancer by applying such an agent in combination with the nanoemulsions disclosed herein to a target and comparing the inactivation of the target when contacted by the admixture with inactivation of like targets by the composition of the present invention without the agent. Any agent that increases germination, and thereby decreases or inhibits the growth of the organisms, is considered a suitable enhancer for use in the nanoemulsion compositions disclosed herein.

In still other embodiments, addition of a germination enhancer (or growth medium) to a neutral emulsion composition produces a composition that is useful in inactivating bacterial spores in addition to enveloped viruses, Gram negative bacteria, and Gram positive bacteria for use in the vaccine compositions of the present invention.

6. Interaction Enhancers

In still other embodiments, nanoemulsions comprise one or more compounds capable of increasing the interaction of the compositions (i.e., "interaction enhancer") with target pathogens (e.g., the cell wall of Gram negative bacteria such as *Vibrio, Salmonella, Shigella* and *Pseudomonas*). In preferred embodiments, the interaction enhancer is preferably premixed with the oil phase; however, in other embodiments the interaction enhancer is provided in combination with the compositions after emulsification. In certain preferred embodiments, the interaction enhancer is a chelating agent (e.g., ethylenediaminetetraacetic acid [EDTA] or ethylenebis(oxyethylenenitrilo)tetraacetic acid [EGTA] in a buffer [e.g., tris buffer]). It is understood that chelating agents are merely exemplary interaction enhancing compounds. Indeed, other agents that increase the interaction of the nanoemulsions used in some embodiments of the present invention with microbial agents and/or pathogens are contemplated. In particularly preferred embodiments, the interaction enhancer is at a concentration of about 50 to about 25 μM. One skilled in the art will be able to determine whether a particular agent has the desired function of acting as an interaction enhancer by applying such an agent in combination with the compositions of the present invention to a target and comparing the inactivation of the target when contacted by the admixture with inactivation of like targets by the composition of the present invention without the agent. Any agent that increases the interaction of an emulsion with bacteria and thereby decreases or inhibits the growth of the bacteria, in comparison to that parameter in its absence, is considered an interaction enhancer.

In some embodiments, the addition of an interaction enhancer to nanoemulsion produces a composition that is useful in inactivating enveloped viruses, some Gram positive bacteria and some Gram negative bacteria for use in the vaccine compositions of the present invention.

7. Quaternary Ammonium Compounds

In some embodiments, nanoemulsions of the present invention include a quaternary ammonium containing compound. Exemplary quaternary ammonium compounds include, but are not limited to, Alkyl dimethyl benzyl ammonium chloride, didecyl dimethyl ammonium chloride, Alkyl dimethyl benzyl and dialkyl dimethyl ammonium chloride, N,N-Dimethyl-2-hydroxypropylammonium chloride polymer, Didecyl dimethyl ammonium chloride, n-Alkyl dimethyl benzyl ammonium chloride, n-Alkyl dimethyl ethylbenzyl ammonium chloride, Dialkyl dimethyl ammonium chloride, n-Alkyl dimethyl benzyl ammonium chloride, n-Tetradecyl dimethyl benzyl ammonium chloride monohydrate, n-Alkyl dimethyl benzyl ammonium chloride, Dialkyl dimethyl ammonium chloride, Hexahydro-1,3,5-tris (2-hydroxyethyl)-s-triazine, Myristalkonium chloride (and) Quat RNIUM 14, Alkyl bis(2-hydroxyethyl) benzyl ammonium chloride, Alkyl dimethyl benzyl ammonium chloride, Alkyl dimethyl 3,4-dichlorobenzyl ammonium chloride, Alkyl dimethyl benzyl ammonium chloride, Alkyl dimethyl benzyl dimethylbenzyl ammonium, Alkyl dimethyl dimethybenzyl ammonium chloride, Alkyl dimethyl ethyl ammonium bromide, Alkyl dimethyl ethyl ammonium bromide, Alkyl dimethyl ethylbenzyl ammonium chloride, Alkyl dimethyl isopropylbenzyl ammonium chloride, Alkyl trimethyl ammonium chloride, Alkyl 1 or 3 benzyl-1-(2-hydroxyethyl)-2-imidazolinium chloride, Dialkyl methyl benzyl ammonium chloride, Dialkyl dimethyl ammonium chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy)ethyl dimethyl benzyl ammonium chloride, Dioctyl dimethyl ammonium chloride, Dodecyl bis (2-hydroxyethyl) octyl hydrogen ammonium chloride, Dodecyl dimethyl benzyl ammonium chloride, Dodecylcarbamoyl methyl dinethyl benzyl ammonium chloride, Heptadecyl hydroxyethylimidazolinium chloride, Hexahydro-1,3,5-tris(2-hydroxyethyl)-s-triazine, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysilyl quats, and Trimethyl dodecylbenzyl ammonium chloride.

8. Production of Nanoemulsions

Nanoemulsions for use in the vaccine compositions of the present invention can be formed using classic emulsion forming techniques. In brief, the oil phase is mixed with the aqueous phase under relatively high shear forces (e.g., using high hydraulic and mechanical forces) to obtain an oil-in-water emulsion containing oil droplets, which are approximately 0.5 to 5 microns, and preferably 1-2 microns, in diameter. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452; herein incorporated by reference in their entireties.

At least a portion of the emulsion may be in the form of lipid structures including, but not limited to, unilamellar, multilamellar, and paucilamellar lipid vesicles, micelles, and lamellar phases. Nanoemulsion compounds can be produced in large quantities and are stable for many months at a broad range of temperatures. Undiluted, they tend to have the texture of a semi-solid cream and can be applied topically by hand or mixed with water. Diluted, they tend to have a consistency and appearance similar to skim milk.

D. Animal Models

In some embodiments, potential nanoemulsion vaccines are tested in animal models of infectious diseases. The use of well-developed animal models provides a method of measuring the effectiveness and safety of a vaccine before administration to human subject. Exemplary animal models of disease are shown in Table 3. These animals are commercially available (e.g., from Jackson Laboratories Charles River, Portage, Mich.).

Animal models of *Bacillus cereus* (closely related to *Bacillus anthracis*) are utilized to test Anthrax vaccines of the present invention. Both bacteria are spore forming Gram positive rods and the disease syndrome produced by each bacteria is largely due to toxin production and the effects of these toxins on the infected host (Brown et al., J. Bact., 75:499 [1958]; Burdon and Wende, J. Infect Dis., 107:224 [1960]; Burdon et al., J. Infect. Dis., 117:307 [1967]). *Bacillus cereus* infection mimics the disease syndrome caused by *Bacillus anthracis*. Mice are reported to rapidly succumb to the effects of *B. cereus* toxin and are a useful model for acute infection. Guinea pigs develop a skin lesion subsequent to subcutaneous infection with *B. cereus* that resembles the cutaneous form of anthrax.

*Clostridium perfringens* infection in both mice and guinea pigs has been used as a model system for the in vivo testing of antibiotic drugs (Stevens et al., Antimicrob. Agents Chemother., 31:312 [1987]; Stevens et al., J. Infect Dis., 155:220 [1987]; Alttemeier et al., Surgery, 28:621 [1950]; Sandusky et al., Surgery, 28:632 [1950]). *Clostridium tetani* is well known to infect and cause disease in a variety of mammalian species. Mice, guinea pigs, and rabbits have all been used experimentally (Willis, Topley and Wilson's Principles of Bacteriology, Virology and Immunity. Wilson, G., A. Miles, and M. T. Parker, eds. pages 442-475 1983).

*Vibrio cholerae* infection has been successfully initiated in mice, guinea pigs, and rabbits. According to published reports it is preferred to alter the normal intestinal bacterial flora for the infection to be established in these experimental hosts. This is accomplished by administration of antibiotics to suppress the normal intestinal flora and, in some cases, withholding food from the animals (Butterton et al., Infect. Immun., 64:4373 [1996]; Levine et al., Microbiol. Rev., 47:510 [1983]; Finkelstein et al., J. Infect Dis., 114:203 [1964]; Freter, J. Exp. Med., 104:411 [1956]; and Freter, J. Infect. Dis., 97:57 [1955]).

*Shigella flexnerii* infection has been successfully initiated in mice and guinea pigs. As is the case with vibrio infections, it is preferred that the normal intestinal bacterial flora be altered to aid in the establishment of infection in these experimental hosts. This is accomplished by administration of antibiotics to suppress the normal intestinal flora and, in some cases, withholding food from the animals (Levine et al., Microbiol. Rev., 47:510 [1983]; Freter, J. Exp. Med., 104:411 [1956]; Formal et al., J. Bact., 85:119 [1963]; LaBrec et al., J. Bact. 88:1503 [1964]; Takeuchi et al., Am. J. Pathol., 47:1011 [1965]).

Mice and rats have been used extensively in experimental studies with *Salmonella typhimurium* and *Salmonella enteriditis* (Naughton et al., J. Appl. Bact., 81:651 [1996]; Carter and Collins, J. Exp. Med., 139:1189 [1974]; Collins, Infect. Immun., 5:191 [1972]; Collins and Carter, Infect. Immun., 6:451 [1972]).

Mice and rats are well established experimental models for infection with Sendai virus (Jacoby et al., Exp. Gerontol, 29:89 [1994]; Massion et al., Am. J. Respir. Cell Mol. Biol. 9:361 [1993]; Castleman et al., Am. J. Path., 129:277 [1987]; Castleman, Am. J. Vet. Res., 44:1024 [1983]; Mims and Murphy, Am. J. Path., 70:315 [1973]).

Sindbis virus infection of mice is usually accomplished by intracerebral inoculation of newborn mice. Alternatively, weanling mice are inoculated subcutaneously in the footpad (Johnson et al., J. Infect. Dis., 125:257 [1972]; Johnson, Am. J. Path., 46:929 [1965]).

It is preferred that animals are housed for 3-5 days to rest from shipping and adapt to new housing environments before use in experiments. At the start of each experiment, control animals are sacrificed and tissue is harvested to establish baseline parameters. Animals are anesthetized by any suitable method (e.g., including, but not limited to, inhalation of Isofluorane for short procedures or ketamine/xylazine injection for longer procedure).

TABLE 3

Animal Models of Infectious Diseases

| Microorganism | Experimental Animal Species | Experimental Animal Strains | Sex | Age | Route of Infection |
|---|---|---|---|---|---|
| *Francisella philomiraga* | mice | BALB/C | M | 6 W | Intraperitoneal |
| *Neisseria meningitidis* | mice | BALB/C | F | 6-10 W | Intraperitoneal |
| | rats | COBS/CD | M/F | 4 D | Intranasal |
| *Streptococcus pneumoniae* | mice | BALB/C | F | 6 W | Intranasal |
| | rats | COBS/CD | M | 6-8 W | Intranasal |
| | guinea Pigs | Hartley | M/F | 4-5 W | Intranasal |
| *Yersinia pseudotuberculosis* | mice | BALB/C | F | 6 W | Intranasal |
| Influenza virus | mice | BALB/C | F | 6 W | Intranasal |
| Sendai virus | mice | CD-1 | F | 6 W | Intranasal |
| | rats | Sprague-Dawley | M | 6-8 W | Intranasal |
| Sindbis | mice | CD-1 | M/F | 1-2 D | Intracerebral/SC |
| Vaccinia | mice | BALB/C | F | 2-3 W | Intradermal |

E. Assays For Evaluation of Vaccines

In some embodiments, candidate nanoemulsion vaccines are evaluated using one of several suitable model systems. For example, cell-mediated immune responses can be evaluated in vitro. In addition, an animal model may be used to evaluate in vivo immune response and immunity to pathogen challenge. Any suitable animal model may be utilized, including, but not limited to, those disclosed in Table 3.

Before testing a nanoemulsion vaccine in an animal system, the amount of exposure of the pathogen to a nanoemulsion sufficient to inactivate the pathogen is investigated. It is contemplated that pathogens such as bacterial spores require longer periods of time for inactivation by the nanoemulsion in order to be sufficiently neutralized to allow for immunization. The time period required for inactivation may be investigated using any suitable method, including, but not limited to, those described in the illustrative In addition, the stability of emulsion-developed vaccines is evaluated, particularly over time and storage condition, to ensure that vaccines are effective long-term. The ability of other stabilizing materials (e.g., dendritic polymers) to enhance the stability and immunogenicity of vaccines is also evaluated.

Once a given nanoemulsion/pathogen vaccine has been formulated to result in pathogen inactivation, the ability of the vaccine to elicit an immune response and provide immunity is optimized. Non-limiting examples of methods for assaying vaccine effectiveness are described in Example 14 below. For example, the timing and dosage of the vaccine can be varied and the most effective dosage and administration schedule determined. The level of immune response is quantitated by measuring serum antibody levels. In addition, in vitro assays are used to monitor proliferation activity by measuring $H^3$-thymidine uptake. In addition to proliferation, Th1 and Th2 cytokine responses (e.g., including but not limited to, levels of include IL-2, TNF-$\gamma$, IFN-$\gamma$, IL-4, IL-6, IL-11, IL-12, etc.) are measured to qualitatively evaluate the immune response.

Finally, animal models are utilized to evaluate the effect of a nanoemulsion mucosal vaccine. Purified pathogens are mixed in emulsions (or emulsions are contact with a pre-infected animal), administered, and the immune response is determined. The level of protection is then evaluated by challenging the animal with the specific pathogen and subsequently evaluating the level of disease symptoms. The level of immunity is measured over time to determine the necessity and spacing of booster immunizations.

III. Therapeutics

The present invention provides nanoemulsion/pathogen formulations suitable for use as vaccines. The compositions can be administered in any effective pharmaceutically acceptable form to subjects including human and animal subjects. Generally, this entails preparing compositions that are essentially free of pyrogens, as well as other impurities that could be harmful to humans or animals.

Particular examples of pharmaceutically acceptable forms include but are not limited to nasal, buccal, rectal, topical or nasal spray or in any other form effective to deliver active vaccine compositions of the present invention to a given site. In preferred embodiments, the route of administration is designed to obtain direct contact of the compositions with the mucosal immune system (e.g., including, but not limited to, mucus membranes of the nasal and stomach areas). In other embodiments, administration may be by orthotopic, intradermal, subcutaneous, intramuscular or intraperitoneal injection. The compositions may also be administered to subjects parenterally or intraperitoneally. Such compositions would normally be administered as pharmaceutically acceptable compositions. Except insofar as any conventional pharmaceutically acceptable media or agent is incompatible with the vaccines of the present invention, the use of known pharmaceutically acceptable media and agents in these particular embodiments is contemplated. In additional embodiments, supplementary active ingredients also can be incorporated into the compositions.

For topical applications, the pharmaceutically acceptable carrier may take the form of a liquid, cream, foam, lotion, or gel, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration.

Actual amounts of compositions and any enhancing agents in the compositions may be varied sa as to obtain amounts of emulsion and enhancing agents at the site of treatment that are effective in inactivating pathogens and producing immunity. According, the selected amounts will depend on the nature and site for treatment, the desired response, the desired duration of biocidal action and other factors. Generally, the emulsion compositions of the invention will comprise at least 0.001% to 100%, preferably 0.001 to 90%, of emulsion per ml of liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention. Some variation in dosage will necessarily occur depending on the condition of the specific pathogen and the subject being immunized.

The person responsible for administration will, in any event, determine the appropriate dose for the individual subject. Moreover, for human administration, preparations should meet sterility, pyrogenicity, and general safety and purity standards as required by the FDA Office of Biologics standards.

EXAMPLES

The following examples serve to illustrate certain preferred embodiments and aspects of the present invention and are not to be construed as limiting the scope thereof.

In the experimental disclosure which follows, the following abbreviations apply: eq (equivalents); $\mu$(micron); M (Molar); $\mu$M (micromolar); mM (millimolar); N (Normal); mol (moles); mmol (millimoles); $\mu$mol (micromoles); nmol (nanomoles); g (grams); mg (milligrams); $\mu$g (micrograms); ng (nanograms); L (liters); ml (milliliters); $\mu$l (microliters); cm (centimeters); mm (millimeters); $\mu$m (micrometers); nM (nanomolar); °C. (degrees Centigrade); and PBS (phosphate buffered saline).

Example 1

Methods of Formulating Emulsions

The emulsion is produced as follows: an oil phase is made by blending organic solvent, oil, and surfactant and then heating the resulting mixture at 37-90° C. for up to one hour. The emulsion is formed either with a reciprocating syringe instrumentation or Silverson high sheer mixer. The water phase is added to the oil phase and mixed for 1-30 minutes, preferably for 5 minutes. For emulsions containing volatile ingredients, the volatile ingredients are added along with the aqueous phase.

In one example, the emulsion was formed as follows: an oil phase was made by blending tri-butyl phosphate, soybean oil, and a surfactant (e.g., TRITON X-100) and then heating the resulting mixture at 86° C. for one hour. An emulsion was then produced by injecting water into the oil phase at a volume/volume ratio of one part oil phase to four parts water. The emulsion can be produced manually, with reciprocating syringe instrumentation, or with batch or continuous flow instrumentation. Methods of producing these emulsions are well known to those of skill in the art and are described in e.g., U.S. Pat. Nos. 5,103,497; and 4,895,452, (herein incorporated by reference in their entireties). Table 4 shows the proportions of each component, the pH, and the size of the emulsion as measured on a Coulter LS 130 laser sizing instrument equipped with a circulating water bath.

TABLE 4

| Chemical Components of Emulsion | Percentage of Each Component | pH | Mean Coulter Size (in Microns) | Mean Coulter Range (in Microns) |
|---|---|---|---|---|
| X8P | | | | |
| TRITON X-100 | 2% | | | |
| Tributyl phosphate | 2% | 5.16 | 1.074 | 0.758-1.428 |
| Oil (ex. Soy bean) | 16% | | | |
| Water | 80% | | | |
| X8P 0.1 * | | | | |
| TRITON X-100 | 0.20% | 5.37 | 0.944 | 0.625-1.333 |
| Tribuyl phosphate | 0.20% | | | |
| Oil (ex. Soy bean) | 1.60% | | | |
| Water | 98% | | | |

* This Emulsion was obtained by diluting the X8P emulsion with water in a ratio of 1:9

The emulsions utilized in the present invention are highly stable. Indeed, emulsions were produced as described above and allowed to stand overnight at room temperature in sealed, different sizes of polypropylene tubes, beakers or flasks. The emulsions were then monitored for signs of separation. Emulsions that showed no signs of separation were considered "stable." Stable emulsions were then monitored over 1 year and were found to maintain stability.

Emulsions were again produced as described above and allowed to stand overnight at −20° C. in sealed 50 mL polypropylene tubes. The emulsions were then monitored for signs of separation. Emulsions that showed no signs of separation were considered "stable." The X8P and X8P 0.1, emulsions have been found to be substantially unchanged after storage at room temperature for at least 24 months.

Example 2

Characterization Of An Exemplary Bacteria-inactivating Emulsion As An Emulsified Liposome Formed In Lipid Droplets A bacteria inactivating emulsion, designated $X8W_{60}PC$, was formed by mixing a lipid-containing oil-in-water emulsion with X8P. In particular, a lipid-containing oil-in-water emulsion having glycerol monooleate (GMO) as the primary lipid and cetylpyridinium chloride (CPC) as a positive charge producing agent (referred to herein as GMO/CPC lipid emulsion or "$W_{80}8P$") and X8P were mixed in a 1:1 (volume to volume) ratio. U.S. Pat. No. 5,547,677 (herein incorporated by reference in its entirety) describes the GMO/CPC lipid emulsion and other related lipid emulsions that may be combined with X8P to provide bacteria-inactivating oil-in-water emulsions utilized in the vaccines of the present invention.

Example 3

In Vitro Bactericidal Efficacy Study I—Gram Positive Bacteria

In order to study the bactericidal efficacy of the emulsions utilized in the vaccines of the present invention, the emulsions were mixed with various bacteria for 10 minutes and then plated on standard microbiological media at varying dilutions. Colony counts were then compared to untreated cultures to determine the percent of bacteria killed by the treatment. Table 5 summarizes the results of the experiment.

TABLE 5

| Organism | Inoculum (CFU) | % Killing | Emulsion Tested |
|---|---|---|---|
| Vibrio cholerae classical | $1.3 \times 10^8$ | 100 | X8P |
| Vibrio cholerae Eltor | $5.1 \times 10^8$ | 100 | X8P |
| Vibrio parahemolytica | $4.0 \times 10^7$ | 98-100 | X8P |

In order to study the bactericidal effect of the emulsions on various vegetative forms of Bacillus species, an emulsion at three dilutions was mixed with four Bacillus species for 10 minutes and then plated on microbiological medium. Colony counts were then compared with untreated cultures to determine the percent of bacteria killed by the treatment. Table 6 contains a summary of the bactericidal results from several experiments with the mean percentage kill in parenthesis.

TABLE 6

| X8P/ Dilution | B. cereus | B. circulans | B. megaterium | B. subtilis |
|---|---|---|---|---|
| 1:10 | 99% (99%) | 95-99% (97%) | 99% (99%) | 99% (99%) |
| 1:100 | 97-99% (98%) | 74-93% (84%) | 96-97% (96%) | 99% (99%) |
| 1:1000 | 0% (0%) | 45-60% (52%) | 0-32% (16%) | 0-39% (20%) |

Example 4

In Vitro Bactericidal Efficacy Study II—Gram Negative Bacteria

To increase the uptake of the bacteria inactivating emulsions by the cell walls of Gram negative bacteria, thereby enhancing the microbicidal effect of the emulsions on the resistant Gram negative bacteria, EDTA (ethylenediaminetetraacetic acid) was premixed with the emulsions. The EDTA was used in low concentrations (50-25 µM) and the mix was incubated with the various Gram negative bacteria for 15 minutes. The microbicidal effect of the mix was then measured on trypticase soy broth. The results are set forth in Table 7 below. There was over 99% reduction of the bacterial count using X8P in 1/100 dilutions. This reduction of count was not due to the killing effect of EDTA alone as shown from the control group in which 250 µM of EDTA alone could not reduce the bacterial count in 15 minutes.

TABLE 7

| Bacterium | Bacteria alone (CFU) | Bacteria + X8P (CFU) | Bacteria + X8P + EDTA (CFU) | Bacteria + EDTA (CFU) |
|---|---|---|---|---|
| S. typhimurium | 1,830,000 | 1,370,000 | 40 | 790,000 |
| S. dysenteriae | 910,000 | 690,000 | 0 | 320,000 |

Example 5

In Vitro Bactericidal Efficacy Study III—Vegetative and Spore Forms

Bacillus cereus (B. cereus, ATCC #14579) was utilized as a model system for Bacillus anthracis. Experiments with X8P diluted preparations to study the bactericidal effect of the compounds of the present invention on the vegetative form (actively growing) of B. cereus were performed. Treatment in medium for 10 minutes at 37° C. was evaluated. As summarized in Table 8, the X8P emulsion is efficacious against the vegetative form of B. cereus. A 10 minute exposure with this preparation is sufficient for virtually complete killing of vegetative forms of B. cereus at all concentrations tested including dilutions as high as 1:100.

TABLE 8

| Emulsion | Undiluted | 1:10 | 1:100 |
|---|---|---|---|
| X8P | >99% Avg = >99% | >99% Avg = >99% | 59 – >99% Avg = 82% |

Number of experiments = 4

The spore form of B. anthracis is one of the most likely organisms to be used as a biological weapon. Spores are well known to be highly resistant to most disinfectants. As describe above, effective killing of spores usually requires the use of toxic and irritating chemicals such as formaldehyde or sodium hypochlorite (i.e., bleach). The same experiment was therefore performed with the spore form of B. cereus. As shown in Table 9, treatment in both medium for 10 minutes at 37° C. was not sufficient to kill B. cereus spores.

TABLE 9

| Emulsion | Undiluted | 1:10 | 1:100 |
|---|---|---|---|
| X8P | 0%-12% Avg = 6% | 0% Avg = 0% | 0% Avg 0% |

Number of experiments = 2

To evaluate the efficacy of the nanoemulsion compounds utilized in the vaccines of the present invention on the spore form of B. cereus over a period of time, X8P was incorporated into solid agar medium at 1:100 dilution and the spores spread uniformly on the surface and incubated for 96 hours at 37° C. No growth occurred on solid agar medium wherein X8P had been incorporated, out to 96 hours (i.e., >99% killing, average >99% killing, 3 experiments).

In an attempt to more closely define the time at which killing of spores by X8P occurred, the following experiment was performed. Briefly, a spore preparation was treated with X8P at a dilution of 1:100 and compared to an untreated control. The number of colony forming units per milliliter (CFU/ml) was quantitated after 0.5, 1, 2, 4, 6, and 8 hours. CFU/ml in the untreated control increased over the first 4 hours of incubation and then reached a plateau. Bacterial smears prepared at time zero, 1, 2, 4 and 6 hours, and stained for spore structures, revealed that by 2 hours no spore structures remained (FIGS. 2A-2C). Thus, 100% germination of spores occurred in the untreated control by the 2 hour time point. In the spore preparation treated with X8P, CFU/ml showed no increase over the first 2 hours and then declined rapidly of the time period from 2-4 hours. The decline from baseline CFU/ml over 2-4 hours was approximately 1000-fold. Bacterial smears prepared at the same time points and stained for spore structures revealed that spore structures remained to the end of the experiment at 8 hours. Hence, germination of spores did not occur in the X8P treated culture due to either inhibition of the germination process or because the spores were damaged and unable to germinate. In order to determine whether the emulsions were effective in killing other Bacillus species in addition to B. cereus, a similar experiment was performed as described above, wherein spore preparations were treated with emulsions and compared to an untreated control after four hours of incubation. The following Table 10 shows the results wherein the numbers represent the mean sporicidal activity from several experiments.

TABLE 10

| X8P/ Dilution | B. cereus | B. circulans | B. megaterium | B. subtilis |
|---|---|---|---|---|
| 1:10 | 82% | 61% | 93% | 31% |
| 1:100 | 91% | 80% | 92% | 39% |
| 1:1000 | 47% | 73% | 94% | 22% |

Example 6

In Vivo Bactericidal Efficacy Study

Animal studies were preformed to demonstrate the protective and therapeutic effect of the emulsions in vivo. Bacillus cereus infection in experimental animals has been used previously as a model system for the study of anthrax (Burdon and Wende, 1960; Burdon et al., 1967; Lamanna and Jones, 1963). The disease syndrome induced in animals experimentally infected with B cereus in some respects similar to anthrax (Drobniewski, 1993; Fritz et al., 1995). The emulsions were mixed with B. cereus spores before injecting into mice.

Irrigation of Skin Wounds

A 1 cm skin wound was infected with $2.5 \times 10^7$ B. cereus spores then closed without any further treatment. The other groups were infected with the same number of spores. One hour later, the wounds were irrigated with either inventive emulsion or saline to simulate wounds with an average area of 4.86 cm$^2$. In addition, 60% of the animals in this group died as a result of the infection. Histology of these lesions indicated total necrosis of the dermis and subdermis and large numbers of vegetative Bacillus organisms. Irrigation of experimentally infected wounds with saline did not result in any apparent benefit.

Irrigation of wounds infected with B. cereus spores with emulsion showed substantial benefit, resulting in a consistent 98% reduction in the lesion size from 4.86 cm$^2$ to 0.06 cm$^2$. This reduction in lesion size was accompanied by a three-fold reduction in mortality (60% to 20%) when compared to experimental animals receiving either no treatment or saline irrigation. Histology of these lesions showed no evidence of vegetative Bacillus organisms and minimal disruption of the epidermis (Hamouda et al., 1999).

Subcutaneous Injection

CD-1 mice were injected with emulsion diluted 1:10 in saline as a control and did not exhibit signs of distress or inflammatory reaction, either in gross or histological analysis. To test the pathogenic effect of B. cereus spores in vivo and the sporicidal effect of emulsion, a suspension of $4 \times 10^6$ B. cereus spores was mixed with saline or with inventive emulsion at a final dilution of 1:10 and then immediately injected subcutaneously into the back of CD-1 mice.

Mice that were infected subcutaneously with B. cereus spores without emulsion developed severe edema at 6-8 hours. This was followed by a gray, necrotic area surrounding the injection site at 18-24 hours, with severe sloughing of the skin present by 48 hours, leaving a dry, red-colored lesion.

Simultaneous injection of spores and emulsion resulted in a greater than 98% reduction in the size of the necrotic lesion from 1.68 cm$^2$ to 0.02 cm$^2$ when the spores were premixed with inventive emulsion. This was associated with minimal edema or inflammation (Hamouda et al., 1999).

Rabbit Cornea

The cornea of rabbits were irrigated with various concentrations of emulsions and monitored at 24 and 48 hours. No irritations or abnormalities were observed when compositions were used in therapeutic amounts.

Mucous Membrane

Intranasal toxicity was performed in mice by installation of 25 μL of 4% of the nanoemulsion per nare. No clinical or histopathological changes were observed in these mice.

Nasal toxicity testing in rats was performed by gavaging up to 8 mL per kg of 25% nanoemulsion. The rats did not lose weight or show signs of toxicity either clinically or histopathologically. There were no observed changes in the gut bacterial flora as a result of nasal administration of the emulsions.

In a particular embodiment, *Bacillus cereus* was passed three times on blood agar (TSA with 5% sheep blood, REMEL). *B. cereus* was scraped from the third passage plate and resuspended in trypticase soy broth (TSB) (available from BBL). The *B. cereus* suspension was divided into two tubes. An equal volume of sterile saline was added to one tube and mixed 0.1 ml of the *B. cereus* suspension/saline was injected subcutaneously into 5 CD-1 mice. An equal volume of X8P (diluted 1:5 in sterile saline) was added to one tube and mixed, giving a final dilution of X8P at 1:10. The *B. cereus* suspension/X8P was incubated at 37° C. for 10 minutes while being mixed 0.1 ml of the *B. cereus* suspension/X8P was injected subcutaneously into 5 CD-1 mice. Equal volumes of X8P (diluted 1:5 in sterile saline) and TSB were mixed, giving a final dilution of X8P at 1:10 0.1 ml of the X8P/TSB was injected subcutaneously into 5 CD-1 mice.

The number of colony forming units (cfu) of *B. cereus* in the inocula were quantitated as follows: 10-fold serial dilutions of the *B. cereus* and *B. cereus*/X8P suspensions were made in distilled H$_2$O. Duplicate plates of TSA were inoculated from each dilution (10 μl per plate). The TSA plates were incubated overnight at 37° C. Colony counts were made and the number of cfu/ml was calculated. Necrotic lesions appears to be smaller in mice which were inoculated with *B cereus* which was pretreated with X8P. The following Table 11 shows the results of the experiment.

TABLE 11

| Inoculum | ID# | Observation |
| --- | --- | --- |
| *B. cereus* 3.1 × 10$^7$ cfu/mouse | 1528 | necrosis at injection Site |
| | 1529 | necrosis at injection site |
| | 1530 | Dead |
| | 1531 | Dead |
| | 1532 | necrosis at injection site |
| *B. cereus* 8.0 × 10$^5$ cfu/mouse (X8P treated) | 1348 | necrosis at injection site |
| | 1349 | no reaction |
| | 1360 | no reaction |
| | 1526 | necrosis at injection site |
| | 1527 | necrosis at injection site |
| X8P/TSR | 1326 | no reaction |
| | 1400 | no reaction |
| | 1375 | no reaction |
| | 1346 | no reaction |
| | 1347 | no reaction |

*Bacillus cereus* was grown on Nutrient Agar (Difco) with 0.1% Yeast Extract (Difco) and 50 μg/ml MnSO$_4$ for induction of spore formation. The plate was scraped and suspended in sterile 50% ethanol and incubated at room temperature for 2 hours with agitation in order to lyse remaining vegetative bacteria. The suspension was centrifuged at 2,500× g for 20 minutes and the supernatant discarded. The pellet was resuspended in diH$_2$O, centrifuged at 2,500× g for 20 minutes, and the supernatant discarded. The spore suspension was divided. The pellet was resuspended in TSB. 0.1 ml of the *B. cereus* spore suspension diluted 1:2 with saline was injected subcutaneously into 3 CD-1 mice. Equal volumes of X8P (diluted 1:5 sterile saline) and *B. cereus* spore suspension were mixed, giving a final dilution of X8P at 1:10 (preincubation time). 0.1 ml of the X8P/*B. cereus* spore suspension was injected subcutaneously into 3 CD-1 mice. The number of colony forming units (cfu) of *B. cereus* in the inoculum was quantitated as follows. 10-fold serial dilutions of the *B. cereus* and *B. cereus*/X8P suspensions were made in distilled H$_2$O. Duplicate plates of TSA were inoculated from each dilution (10 μl per plate). The TSA plates were incubated overnight at 37° C. Colony counts were made and the number of cfu/ml was calculated. Necrotic lesions appeared to be smaller in mice that were inoculated with *B. cereus* spores that were pretreated with X8P. The observations from these studies are shown in Table 12.

TABLE 12

| Inoculum | Observation (24 hours) |
| --- | --- |
| *B. cereus* 6.4 × 10$^6$ spores/mouse | ⅔ (66%) mice exhibited necrosis at injection site |
| *B cereus* 4.8 × 106 spores/mouse (X8P treated) | ⅓ (33%) mice exhibited necrosis at injection site |
| *B. cereus* 4.8 × 10$^6$ vegetative forms/mouse | 3/3 (100%) mice exhibited necrosis at injection site |
| Lysed *B. cereus* 4.8 × 106 cfu/mouse | 3/3 (100%) mice did not exhibit symptoms |
| X8P/TSB | ⅓ (33%) mice appeared to have some skin necrosis |

*Bacillus cereus* was grown on Nutrient Agar (Difco) with 0.1% Yeast Extract (Difco) and 50 (g/ml MnSO$_4$ for induction of spore formation). The plate was scraped and suspended in sterile 50% ethanol and incubated at room temperature for 2 hours with agitation in order to lyse remaining vegetative bacteria. The suspension was centrifuged at 2,500× g for 20 minutes and the supernatant discarded. The pellet was resuspended in distilled H$_2$O, centrifuged at 2,500× g for 20 minutes, and the supernatant discarded. The pellet was resuspended in TSB. The *B. cereus* spore suspension was divided into three tubes. An equal volume of sterile saline was added to one tube and mixed 0.1 ml of the *B. cereus* suspension/saline was injected subcutaneously into 10 CD-1 mice. An equal volume of X8P (diluted 1:5 in sterile saline) was added to the second tube and mixed, giving a final dilution of X8P at 1:10. The *B. cereus* spore suspension/X8P (1:10) was incubated at 37° C. for 4 hours while being mixed. 0.1 ml of the *B. cereus* spore suspension/X8P (1:10) was injected subcutaneously into 10 CD-1 mice. An equal volume of X8P (diluted 1:50 in sterile saline) was added to the third tube and mixed, giving a final dilution of X8P at 1:100. The *B. cereus* spore suspension/X8P (1:100)

was incubated at 37° C. for 4 hours while being mixed. 0.1 ml of the *B. cereus* spore suspension/X8P (1:100) was injected subcutaneously into 10 CD-1 mice. Equal volumes of X8P (diluted 1:5 sterile saline) and TSB were mixed, giving a final dilution of X8P at 1:10. 0.1 ml of the X8PFTSB was injected subcutaneously into 10 CD-1 mice. Equal volumes of X8P (diluted 1:50 in sterile saline) and TSB were mixed, giving a final dilution of X8P at 1:100 0.1 ml of the X8P/TSB was injected subcutaneously into 10 CD-1 mice. The observations from these studies are shown in Table 13 and Table 14.

TABLE 13

| Inoculum sc | ID# | Observation at 24 hours |
|---|---|---|
| *B. cerus* $5.5 \times 10^7$ Spores/mouse No treatment group | 1 | 2.4 cm$^2$ skin lesion with 0.08 cm$^2$ necrotic area |
| | 2 | no abnormalities observed |
| | 3 | Moribund with 8 cm$^2$ skin lesion and Hind limb paralysis |
| | 4 | 3.52 cm$^2$ skin lesion |
| | 5 | 1.44 cm$^2$ skin lesion |
| | 6 | 3.4 cm$^2$ skin lesion |
| | 7 | 5.5 cm$^2$ skin lesion |
| | 8 | 5.5 cm$^2$ skin lesion |
| | 9 | 3.3 cm$^2$ skin lesion with 0.72 cm$^2$ necrotic area |
| | 10 | 2.64 cm$^2$ skin lesion with two necrotic areas (0.33 cm$^2$ and 0.1 cm$^2$) |

Mean lesion size in Spore group alone 3.97 cm$^2$ (1/10 (10%) with no abnormalities observed)
Note: Skin lesions grey in color with edema, necrotic areas red/dry.

TABLE 14

| Inoculum sc | ID # | Observation at 24 hours |
|---|---|---|
| *B. cereus* $2.8 \times 10^7$ spores/mouse in the X8P 1:10 treated group | 41 | no abnormalities observed |
| | 42 | no abnormalities observed |
| | 43 | 1.2 cm$^2$ white skin lesion with grey center, slight edema |
| | 44 | 0.78 cm$^2$ white skin lesion |
| | 45 | 0.13 cm$^2$ white skin lesion |
| | 46 | 2.2 cm$^2$ white skin lesion |
| | 47 | 1.8 cm$^2$ white skin lesion with 0.1 cm$^2$ brown area in center |
| | 48 | 1 cm$^2$ white skin lesion with grey center |
| | 49 | 0.78 cm$^2$ white skin lesion |
| | 50 | no abnormalities observed |
| | | Mean lesion size in X8P 1:10 treatment group = 1.13 cm$^2$ (3/10 (30%) with no abnormalities observed) |
| *B. cereus* $1.8 \times 10^7$ spores/mouse in the X8P 1:100 treated group | 51 | 2.1 cm$^2$ grey skin lesion |
| | 52 | 0.72 cm$^2$ grey skin lesion |
| | 53 | 1.5 cm$^2$ grey skin lesion |
| | 54 | 1.2 cm$^2$ grey skin lesion |
| | 55 | 3.15 cm$^2$ grey skin lesion |
| | 56 | 0.6 cm$^2$ grey skin lesion |
| | 57 | 0.5 cm$^2$ grey skin lesion |
| | 58 | 2.25 cm$^2$ grey skin lesion |
| | 59 | 4.8 cm$^2$ grey skin lesion with necrotic area 1 cm diameter |
| | 60 | 2.7 cm$^2$ grey skin lesion |
| | | Mean lesion size In X8P 1:100 treatment group = 1.9 cm$^2$ (0/10 (0%) with no abnormalities observed) |
| X8P 1:10 alone | 11 | 2.6 cm$^2$ white area |
| | 12 | 0.15 cm$^2$ white area |
| | 13 | no abnormalities observed |
| | 14 | 0.15 cm$^2$ white area |
| | 15 | 0.35 cm$^2$ white area |
| | 16 | no abnormalities observed |
| | 17 | 0.12 cm$^2$ white area |
| | 18 | no abnormalities observed |
| | 19 | 0.56 cm$^2$ white area |
| | 20 | 0.3 cm$^2$ white area |

TABLE 14-continued

| Inoculum sc | ID # | Observation at 24 hours |
|---|---|---|
| | | Mean lesion size In X8P 1:10 alone group = 0.60 cm$^2$ (3/10 (30%) with no abnormalities observed) |
| X8P 1:100 alone | 21–30 | no abnormalities observed Mean lesion size in X8P 1:100 alone group = 0 cm$^2$ (10/10 (100%) with no abnormalities observed) |
| TSB alone | 31–40 | no abnormalities observed Mean lesion size In the TSB alone group = 0 cm$^2$ (10/10 (100%) with no abnormalities observed) |

Re-isolation of *B. cereus* was attempted from skin lesions, blood, liver, and spleen (Table 15). Skin lesions were cleansed with betadine followed by 70% sterile isopropyl alcohol. An incision was made at the margin of the lesion and swabbed. The chest was cleansed with betadine followed by 70% sterile isopropyl alcohol. Blood was drawn by cardiac puncture. The abdomen was cleansed with betadine followed by 70% sterile isopropyl alcohol. The skin and abdominal muscles were opened with separate sterile instruments. Samples of liver and spleen were removed using separate sterile instruments. Liver and spleen samples were passed briefly through a flame and cut using sterile instruments. The freshly exposed surface was used for culture BHI agar (Difco) was inoculated and incubated aerobically at 37° C. overnight.

TABLE 15

| Inoculum sc | ID# | Necrospy | *B. cereus* Re-isolation From site of skin lesion |
|---|---|---|---|
| *B. cereus* $5.5 \times 10^7$ spores mouse in the Untreated group | 3 | 24 hours | skin lesion >300 cfu |
| | 6 | 48 hours | skin lesion >300 cfu |
| | 7 | 48 hours | skin lesion >300 cfu |
| | 8 | 72 hours | skin lesion 100 cfu |
| | 9 | 72 hours | skin lesion 25 cfu |
| | 10 | 72 hours | skin lesion 100 |
| | 1 | 96 hours | skin lesion >300 cfu |
| | 4 | 96 hours | skin lesion >300 cfu |
| | 5 | 96 hours | skin lesion >300 cfu |
| | | Mean CFU In Untreated Spore group = 214* *(6/9 (67%) > 300 CFU) | |
| *B. cereus* $2.8 \times 10^7$ spores/mouse in the X8P 1:10 treated group | 48 | 48 hours | skin lesion 17 cfu |
| | 50 | 48 hours | skin lesion >300 cfu |
| | 46 | 72 hours | skin lesion >200 cfu |
| | 47 | 72 hours | skin lesion 100 cfu |
| | 49 | 72 hours | skin lesion >300 cfu |
| | 41 | 96 hours | skin lesion >300 cfu |
| | 42* | 96 hours | skin lesion 20 cfu |
| | 43 | | cultures not done |
| | 44 | 96 hours | skin lesion >300 cfu |
| | 45 | | cultures not done |
| | 46 | | cultures not done |
| | | Mean CFU in X8P 1:10 group = 192* *(318 (38%) > 300 CFU) | |
| *B. cereus* $1.8 \times 10^7$ spores/mouse in the X8P 1:100 treated group | 48 | 48 hours | skin lesion 18 cfu |
| | 50* | 48 hours | skin lesion >300 cfu |
| | 52 | 72 hours | skin lesion I cfu |
| | 54 | 72 hours | re-isolation negative |
| | 56 | 72 hours | skin lesion >300 cfu |
| | 58 | 96 hours | skin lesion 173 cfu |
| | 59 | 96 hours | skin lesion 4 cfu |
| | 60 | 96 hours | skin lesion 6 cfu |
| | | Mean CFU in X8P 1:100 group = 100 *(2/8 (25%) > 00 CFU) | |

*Although no lesions were present in these mice, organisms were removed from the injection site.

Pretreatment of both vegetative *B. cereus* and *B. cereus* spores reduce their ability to cause disease symptoms when introduced into experimental animals. This is reflected in the smaller size of skin lesions and the generally lower numbers of *B. cereus* recovered from the lesions. In addition, less frequent re-isolation of *B. cereus* from blood, liver, and spleen occurs suggesting that septicemia may be preventable.

Example 7

In Vivo Toxicity Study I

CD-1 mice were injected subcutaneously with 0.1 ml of nanoemulsion and observed for 4 days for signs of inflammation and/or necrosis. Dilutions of the compounds were made in sterile saline. Tissue samples from mice were preserved in 10% neutral buffered formalin for histopathologic examination. Samples of skin and muscle (from mice which were injected with undiluted compounds) sent for histological review were reported to show indications of tissue necrosis. Tissue samples from mice which were injected with diluted compounds were not histologically examined. Tables 16 and 17 show the results of two individual experiments.

TABLE 16

| Compound | Mouse ID # | Dilution | Observation |
|---|---|---|---|
| X8P | 1326 | Undiluted | necrosis |
|  | 1327 | Undiluted | no reaction |
|  | 1328 | 1:10 | no reaction |
|  | 1329 | 1:10 | no reaction |
|  | 1324 | 1:100 | no reaction |
|  | 1331 | 1:100 | no reaction |
| Saline | 1344 |  | no reaction |
|  | 1345 |  | no reaction |

TABLE 17

| Compound | Mouse ID # | Dilution | Observation |
|---|---|---|---|
| X8P | 1376 | Undiluted | necrosis |
|  | 1377 | Undiluted | minimal necrosis |
|  | 1378 | 1:10 | no reaction |
|  | 1379 | 1:10 | no reaction |
|  | 1380 | 1:100 | no reaction |
|  | 1381 | 1:100 | no reaction |
| Saline | 1394 |  | no reaction |
|  | 1395 |  | no reaction |

Guinea pigs were injected intramuscularly (in both hind legs) with 1.0 ml of compounds of the present invention per site and observed for 4 days for signs of inflammations and/or necrosis. Dilutions of the compound were made in sterile saline.

Tissue samples from guinea pigs were preserved in 10% neutral buffered formalin for histological examination. Tissue samples were not histologically examined.

TABLE 18

| Compound | Guinea Pig | Dilution | Observation |
|---|---|---|---|
| X8P | 1023-1 | undiluted | no reaction |
|  | 1023-2 | 1:10 | no reaction |
|  | 1023-3 | 1:100 | no reaction |
| Saline | 1023-10 |  | no reaction |

The results of In Vivo Toxicity Study I show that subcutaneous and intramuscular injection of the compounds tested did not result in grossly observable tissue damage and did not appear to cause distress in the experimental animals (Table 18).

Example 8

In Vivo Toxicity Study II

One group of Sprague-Dawley rats each consisting of five males and five females were placed in individual cages and acclimated for five days before dosing. Rats were dosed daily for 14 days. On day 0-13, for 14 consecutive days each rat in Group 1 received by gavage three milliliters of X8P, 1:100 concentration, respectively. The three-milliliter volume was determined to be the maximum allowable nasal dose for rats. Prior to dosing on Day 0 and Day 7, each rat was weighed. Thereafter rats were weighed weekly for the duration of the study. Animals were observed daily for sickness or mortality. Animals were allowed to rest for 14 days. On day 28 the rats were weighed and euthanized. The mean weight results of the nasal toxicity study are shown in Table 19. Mean weights for males and females on days 0, 7, and 14, 21 and 28 and the mean weight gains from day 0-day 28, are also shown in Table 18. One rat died due to mechanical trauma from manipulation of the gavage tubing during dosing on day 14. All surviving rats gained weight over the 28 day course of the study and there was no illness reported. Thus, although tributyl phosphate alone is known to be toxic and irritating to mucous membranes, when incorporated into the emulsions utilized in the vaccines of the present invention, these characteristics are not in evidence. The X8P emulsion, 1:100 concentration, was also tested for dermal toxicity in rabbits according to the protocols provided in 16 CFR § 1500.3. The emulsion was not irritating to skin in the animals tested.

TABLE 19

| Rat Number | Sex | Dose Volume mL | Body Weight (g) Day 0 | Body Weight (g) Day 7 | Body Weight (g) Day 14 | Body Weight (g) Day 21 | Body Weight (g) Day 28 | Weight Gain (g) Day 0 Day 28 |
|---|---|---|---|---|---|---|---|---|
| 9028 | m | 3 | 332.01 | 356.52 | 388.66 | 429.9 | 394.07 | 62.06 |
| 9029 | m | 3 | 278.62 | 294.65 | 296.23 | 310.7 | 392.6 | 113.98 |
| 9030 | m | 3 | 329.02 | 360.67 | 325.26 | 403.43 | 443.16 | 114.14 |
| 9031 | m | 3 | 334.64 | 297.04 | 338.82 | 357.5 | 416.89 | 82.25 |
| 9032 | m | 3 | 339.03 | 394.39 | 347.9 | 331.38 | 357.53 | 18.5 |
| MEAN WTS |  |  |  | 266.26 | 340.65 | 339.37 | 400.85 | 78.18 |

TABLE 19-continued

| Rat Number | Sex | Dose Volume mL | Body Weight (g) Day 0 | Body Weight (g) Day 7 | Body Weight (g) Day 14 | Body Weight (g) Day 21 | Body Weight (g) Day 28 | Weight Gain (g) Day 0 Day 28 |
|---|---|---|---|---|---|---|---|---|
| 9063 | F | 3 | 302 | 298.08 | 388.66 | 338.41 | 347.98 | 45.98 |
| 9064 | F | 3 | 254.54 | 247.97 | 256.78 | 278.17 | 279.2 | 24.66 |
| 9065 | F | 3 | 225.99 | 253.81 | 273.38 | 290.54 | 308.68 | 82.69 |
| 9066 | F | 3 | 246.56 | 260.38 | 266.21 | 235.12 | 272.6 | 26.04 |
| 9067 | F | 3 | 279.39 | 250.97 | deceased | | | |
| MEAN WTS | | | 261.69 | 262.24 | 296.25 | 285.56 | 302.11 | 53 |

Example 9

In Vitro Study With *Bacillus anthracis*

Experiments with X8W$_{60}$PC preparations to study the bactericidal effect of the compounds of the present invention on the spore form of *B. anthracis* were performed. The sproricidal activity of different dilutions of X$_8$W$_{60}$PC (in water) on six different strains of *B. anthracis* was tested. X$_8$W$_{60}$PC killed over 98% of seven different strains of anthrax (Del Rio, Tex.; Bison, Canada; South Africa (2 strains); Mozambique; S. Dak.; and Ames, USAMRID) within 4 hours and is as efficient as 1-10% bleach. Similar sporicidal activity is found with different dilutions of X$_8$W$_{60}$PC in media (1:10, 1:100, 1:1000, and 1:5000). X$_8$W$_{60}$PC can kill anthrax spores in as little as 30 minutes.

Example 10

Mechanisms Of Action

The following example provides an insight into the proposed mechanisms of action of several nanoemulsions. This example also demonstrates the sporicidal activity of several nanoemulsions utilized in the vaccines of the present invention. This mechanism is not intended to limit the scope of the invention. An understanding of the mechanism is not necessary to practice the present invention, and the present invention is not limited to any particular mechanism. The effect of a GMO/CPC lipid emulsion ("W$_{80}$8P") and X8P on *E. coli* was examined. W$_{80}$8P killed the *E. coli* (in deionized H$_2$O) but X8P was ineffective against this organism. X8P treated *E. coli* look, normal, with defined structure and intact lipid membranes. W$_{80}$8P treated *E. coli* have vacuoles inside and the contents have swollen so that the defined structure of the organism is lost. Without being bound to a particular theory (an understanding of the mechanism is not necessary to practice the present invention, and the present invention is not limited to any particular mechanism), this observation suggests that W$_{80}$8P kills the bacteria without lysing them and instead causes a change in the internal structure, evident by the vacuolization and swelling. A second study was performed with *Vibrio cholerae*. Despite *Vibrio cholerae* being closely related to *E. coli*, X8P, W$_{80}$8P and X8W$_{60}$PC all killed this organism. Compared to the control the W$_{80}$8P treated *Vibrio cholerae* again shows swelling and changes in the interior of the organism, but the cells remain intact. In contrast, the X8P treated *Vibrio cholerae* are completely lysed with only cellular debris remaining. X8W$_{60}$PC showed a combination of effects, where some of the organisms are swelled but intact and some are lysed. This clearly suggests that X8P, W$_{80}$8P and X8W$_{60}$PC work by different mechanisms.

A third comparative study was performed to evaluate efficacy of the emulsions at various concentrations. As shown in Table 20, X8W$_{60}$PC is more effective as a biocide at lower concentrations (higher dilutions) in bacteria sensitive to either W$_{80}$8P or X8P. In addition, six other bacteria that are resistant to W$_{80}$8P and X8P are all susceptible to X8W$_{60}$PC. This difference in activity is also seen when comparing W$_{80}$8P and X8P and X8W$_{60}$PC in influenza infectivity assays. Both X8P and X8W$_{60}$PC are effective at a 1:10 and 1:100 dilutions and additionally, X8W$_{60}$PC is effective at the lowest concentration, 1:1,000 dilution. In contrast, W$_{80}$8P has little activity even at 1:10 dilution, suggesting that it is not an effective treatment for this enveloped organism. In addition, X8W$_{60}$PC kills yeast species that are not killed by either W$_{80}$8P or X8P.

TABLE 20

Lowest Nanoemulsion Concentration Required to Achieve Over 90% Killing of Selected Microorganisms

| | W$_{80}$8P | X8P | X8W$_{60}$PC |
|---|---|---|---|
| Bacteria | | | |
| *Streptococcus pyogenes* | No killing | 10% | 0.1% |
| *Streptococcus aglactiae* | 1%* | 1% | ND |
| *Streptococcus pneumonia* | 10%* | 1% | 0.1% |
| *Staphylococcus aureus* | No killing | No killing | 0.1% |
| *Neisseria gonorrhoeae* | ND | 1% | 0.1% |
| *Haemophilus influenzae* | 10% | 1% | 0.1% |
| *Vibrio cholerae* | 1% | 0.1% | 0.1% |
| *E. coli* | No killing # | No killing | 0.1% |

TABLE 20-continued

Lowest Nanoemulsion Concentration Required to Achieve Over 90% Killing of Selected Microorganisms

|  | $W_{80}8P$ | X8P | $X8W_{60}PC$ |
|---|---|---|---|
| *Salmonella typhimurium* | No killing # | No killing | 10% |
| *Shigella dysenteriae* | No killing # | No killing | 0.1% |
| *Proteus mirabilis* | No killing # | No killing | 1% |
| *Pseudomonas aeruginosa* | No killing | No killing | 10% |
| *Bacillus anthracis* spores | No killing @ 4 H | 0.1% @ 4 H | 0.1%-0.02% @ 4 H |
| *Bacillus cereus* spores | 10% @ 4 H | 1% @ 4 H | 0.1% @ 4 H |
| *Bacillus subtilis* spores | No killing @ 24 H | No killing @ 24 H | 0.1% @ 4 H |
| *Yersinia enterocolitica* | ND | ND | 0.1% |
| *Yersinia pseudotuberculosis* | ND | ND | 0.1% |
| Fungi |  |  |  |
| *Candida albicans* (ATCC 90028) | No Killing | No Killing | 1% |
| *Candula tropicalis* | No Killing | No Killing | 1% |
| Viruses |  |  |  |
| Influenza A H2N2 | No Killing | 1% | 0.1% |
| Influenza B/Hong Kong/5/72 | ND | 1% | ND |
| Vaccinia | ND | 1% | % |
| Herpes simplex type I | ND | 1% | 0.1% |
| Sendai | ND | 1% | ND |
| Sindbis | ND | 1% | ND |
| Adenovirus | ND | No Killing | ND |

*Data for lower concentrations not available.
No killing except in deionized water.
10 ND = Not determined.

Example 11

Further Evidence of the Sporicidal Activity of Nanoemulsions Against *Bacillus* Species The present Example provides the results of additional investigations of the ability of nanoemulsions to inactivate different *Bacillus* spores. The methods and results of these studies are outlined below.

Surfactant lipid preparations: X8P, a water-in-oil nanoemulsion, in which the oil phase was made from soybean oil, tri-n-butyl phosphate, and TRITON X-100 in 80% water. $X8W_{60}PC$ was prepared by mixing equal volumes of X8P with $W_{80}8P$ which is a liposome-like compound made of glycerol monostearate, refined Soya sterols, TWEEN 60, soybean oil, a cationic ion halogen-containing CPC and peppermint oil.

Spore preparation: For induction of spore formation, *Bacillus cereus* (ATTC 14579), *B. circulars* (ATC 4513), *B. megaterium* (ATCC 14581), and *B. subtilis* (ATCC 11774) were grown for a week at 37° C. on NAYEMn agar (Nutrient Agar with 0.1% Yeast Extract and 5 mg/l $MnSO_4$). The plates were scraped and the bacteria/spores suspended in sterile 50% ethanol and incubated at room temperature (27° C.) for 2 hours with agitation in order to lyse the remaining vegetative bacteria. The suspension was centrifuged at 2,500× g for 20 minutes and the pellet washed twice in cold $diH_2O$. The spore pellet was resuspended in trypticase soy broth (TSB) and used immediately for experiments. *B. anthracis* spores, Ames and Vollum 1 B strains, were kindly supplied by Dr. Bruce Ivins (USAMRIID, Fort Detrick, Frederick, Md.), and prepared as previously described (Ivins et al., Vaccine 13:1779 [1995]). Four other strains of anthrax were kindly provided by Dr. Martin Hugh-Jones (LSU, Baton Rouge, La.) These strains represent isolates with high allelic dissimilarity from South Africa; Mozambique; Bison, Canada; and Del Rio, Tex.

In vitro sporicidal assays: For assessment of sporicidal activity of solid medium, trypticase Soy Agar (TSA) was autoclaved and cooled to 55° C. The X8P was added to the TSA at a 1:100 final dilution and continuously stirred while the plates were poured. The spore preparations were serially diluted (ten-fold) and 10 µl aliquots were plated in duplicate (highest inoculum was $10^5$ spores per plate). Plates were incubated for 48 hours aerobically at 37° C. and evaluated for growth.

For assessment of sporicidal activity in liquid medium, spores were resuspended in TSB. 1 ml of spore suspension containing $2 \times 10^6$ spores (final concentration $10^6$ spores/ml) was mixed with 1 ml of X8P or $X8W_{60}PC$ (at 2× final concentration in $diH_2O$) in a test tube. The tubes were incubated in a tube rotator at 37° C. for four hours. After treatment, the suspensions were diluted 10fold in $diH_2O$. Duplicate aliquots (25 µl) from each dilution were streaked on TSA, incubated overnight at 37° C., and then colonies were counted. Sporicidal activity expressed as a percentage killing was calculated:

$$\frac{cfu \text{ [initial]} - cfu \text{ [post - treatment]}}{cfu \text{[initial]}} \times 100.$$

The experiments were repeated at least 3 times and the mean of the percentage killing was calculated.

Electron microscopy: *B. cereus* spores were treated with X8P at a 1:100 final dilution in TSB using Erlenmeyer flasks in a 37° C. shaker incubator. Fifty ml samples were taken at intervals and centrifuged at 2,500× g for 20 minutes and the supernatant discarded. The pellet was fixed in 4% glutaraldehyde in 0.1 M cacodylate (pH 7.3). Spore pellets were processed for transmission electron microscopy and thin sections examined after staining with uranyl acetate and lead citrate.

Germination inhibitors/simulators: *B. cereus* spores (at a final concentration $10^6$ spores/ml) were suspended in TSB with either the germination inhibitor D-alanine (at final concentration of 1 μM) or with the germination stimulator L-alanine+inosine (at final concentrations of 50 μM each) (Titball and Manchee, J. Appl Bacteriol. 62:269 [1987]; Shibata et al., Jpn J Microbial. 20:529 [1976]) and then immediately mixed with X8P (at a final dilution of 1:100) and incubated for variable intervals. The mixtures were then serially diluted, plated and incubated overnight. The next day the plates were counted and percentage sporicidal activity was calculated.

In vivo sporicidal activity: Two animal models were developed; in the first *B. cereus* spores (suspended in sterile saline) were mixed with an equal volume of X8P at a final dilution of 1:10. As a control, the same *B. cereus* spore suspension was mixed with an equal volume of sterile saline. 100 μl of the suspensions containing $4 \times 10^7$ spores was then immediately injected subcutaneously into CD-1 mice.

In the second model, a simulated wound was created by making an incision in the skin of the back of the mice. The skin was separated from the underlying muscle by blunt dissection. The "pocket" was inoculated with 200 μl containing $2.5 \times 10^7$ spores (in saline) and closed using wound clips. One hour later, the clips were removed and the wound irrigated with either 2 ml of sterile saline or with 2 ml of X8P (1:10 in sterile saline). The wounds were then closed using wound clips. The animals were observed for clinical signs. Gross and histopathology were performed when the animals were euthanized 5 days later. The wound size was calculated by the following formula: $\frac{1}{2}a \times \frac{1}{2}b \times \pi$ where a and b are two perpendicular diameters of the wound.

In vitro sporicidal activity: To assess the sporicidal activity of X8P, spores from four species of *Bacillus* genus, *B. cereus*, *B. circulars*, *B. megatetium*, and *B. subtilis* were tested. X8P at 1:100 dilution showed over 91% sporicidal activity against *B. cereus* and *B. megaterium* in 4 hours. *B. circulars* was less sensitive to X8P showing 80% reduction in spore count, while *B. subtilis* appeared resistant to X8P in 4 hours. A comparison of the sporicidal effect of X8P (at dilutions of 1:10 and 1:100) on *B. cereus* spores was made with a 1:100 dilution of bleach (i.e., 0.0525% sodium hypochlorite), and no significant difference was apparent in either the rate or extent of sporicidal effect. The other nanoemulsion, $X8W_{60}PC$, was more efficient in killing the *Bacillus* spores. At 1:1000 dilution, it showed 98% killing of *B. cereus* spores in 4 hours (compared to 47% with 1:1000 dilution of X8P). $X8W_{60}PC$ at a 1:1000 dilution resulted in 97.6% killing of *B. subtilis* spores in 4 hours, in contrast to its resistance to X8P.

*B. cereus* sporicidal time course: A time course was performed to analyze the sporicidal activity of X8P diluted 1:100 and $X8W_{60}PC$ diluted 1:1000 against *B. cereus* over an eight hour period. Incubation of X8P diluted 1:100 *B. cereus* spores resulted in a 77% reduction in the number of viable spores in one hour and a 95% reduction after 4 hours. Again, $X8W_{60}PC$ diluted 1:1000 was more effective than X8P 1:100 and resulted in about 95% reduction in count after 30 minutes.

X8P *B. anthracis* sporicidal activity: Following initial in vitro experiments, X8P sporicidal activity was tested against two virulent strains of *B. anthracis* (Ames and Vollum 1B). It was found that X8P at a 1:100 final dilution incorporated into growth medium completely inhibited the growth of $1 \times 10^5$ *B. anthracis* spores. Also, 4 hours incubation with X8P at dilutions up to 1:1000 with either the Ames or the Vollum 1 B spores resulted in over 91% sporicidal activity when the mixtures were incubated at RT, and over 96% sporicidal activity when the mixtures were incubated at 37° C. (Table 21).

Table 21: X8P sporicidal activity against 2 different strains of *Bacillus anthracis* spores as determined by colony reduction assay (% killing). X8P at dilutions up to 1:1000 effectively killed >91% of both spore strains in 4 hours at either 27 or 37° C.; conditions that differed markedly in the extent of spore germination. Sporicidal activity was consistent at spore concentrations up to $1 \times 10^6$/ml.

TABLE 21

| | Ames | Ames (cont) | Vollum 1 B | |
|---|---|---|---|---|
| *B. anthracis* | Room Temp. | 37° C. | Room Temp. | 37° C. |
| X8P 1:10 | 91% | 96% | 97% | 99% |
| X8P 1:100 | 93% | 97% | 97% | 98% |
| X8P 1:1000 | 93% | 97% | 98% | 99% |

$X8W_{60}PC$ *B. anthracis* sporicidal activity: Since $X8W_{60}PC$ was effective at higher dilutions and against more species of *Bacillus* spores than X8P, it was tested against 4 different strains of *B. anthracis* at dilutions up to 1:10,000 at RT to prevent germination. $X8W_{60}PC$ showed peak killing between 86% and 99.9% at 1:1000 dilution (Table 22).

Table 22: $X8W_{60}PC$ sporicidal activity against 4 different strains of *B. anthracis* representing different clinical isolates. The spores were treated with $X8W_{60}PC$ at different dilutions in RT to reduce germination. There was no significant killing at low dilutions. The maximum sporicidal effect was observed at 1:1000 dilution.

TABLE 22

| *B. anthracis* | South Africa | Bison, Canada | Mozambigue | Del Rio, Texas |
|---|---|---|---|---|
| $X8W_{60}PC$ 1:10 | 81.8 | 85.9 | 41.9 | 38 |
| $X8W_{60}PC$ 1:100 | 84 | 88.9 | 96.5 | 91.3 |
| $X8W_{60}PC$ 1:1000 | 98.4 | 91.1 | 99.9 | 86 |
| $X8W_{60}PC$ 1:5,000 | 79.7 | 41.3 | 95.7 | 97.1 |
| $X8W_{60}PC$ 1:10,000 | 52.4 | 80 | ND | ND |

Electron microscopy examination of the spores: Investigations were carried out using *B. cereus* because it is the most closely related to *B. anthracis*. Transmission electron microscopy examination of the *B. cereus* spores treated with X8P diluted 1:100 in TSB for four hours revealed physical damage to the *B. cereus* spores, including extensive disruption of the spore coat and cortex with distortion and loss of density in the core.

Germination stimulation and inhibition: To investigate the effect of initiation of germination on the sporicidal effect of X8P on Bacillus spores, the germination inhibitors D-alanine (Titball and Manchee, 1987, supra), and germination simulators L-alanine and inosine (Shibata et al., 1976, supra) were incubated with the spores and X8P for 1 hour. The sporicidal effect of X8P was delayed in the presence of 10 mM D-alanine and accelerated in the presence of 50 μM L-alanine and 50 μM inosine.

In vivo sporicidal activity: *Bacillus cereus* infection in experimental animals had been previously used as a model system for the study of anthrax and causes an illness similar to experimental anthrax infection (Welkos et al., Infect Immun. 51:795 [1986]; Drobniewski, Clin Microbiol Rev. 6:324 [1993]; Burdon et al., J Infect Dis. 117:307 [1967]; Fritz et al. Lab Invest. 73:691 [1995]; Welkos and Friedlander, Microb Pathog 5:127 [1988]). Two animal models of cutaneous *B. cereus* disease were developed to assess the in vivo efficacy of X8P. Because these models involve subcutaneous administration of the nanoemulsion, in vivo toxicity testing of X8P was performed prior to this application. CD-1 mice injected with X8P diluted 1:10 in saline as a control did not exhibit signs of distress or inflammatory reaction, either in gross or histological analysis. To test the pathogenic effect of *B. cereus* spores in vivo and the sporicidal effect of X8P, a suspension of $4\times10^7$ *B. cereus* spores was mixed with saline or with X8P at a final dilution of 1:10 and then immediately injected subcutaneously into the backs of CD-1 mice. Mice which were infected subcutaneously with *B. cereus* spores without X8P developed severe edema at 6-8 hours. This was followed by a gray, necrotic area surrounding the injection site at 18-24 hours, with severe sloughing of the skin present by 48 hours, leaving a dry, red-colored lesion. Simultaneous injection of spores and X8P resulted in a greater than 98% reduction in the size of the necrotic lesion from 1.68 $cm^2$ to 0.02 $cm^2$ when the spores were premixed with X8P. This was associated with minimal edema or inflammation.

In additional studies, a 1 cm skin wound was infected with $2.5\times10^7$ *B. cereus* spores then closed without any further treatment. The other groups were infected with the same number of spores, then 1 hour later the wounds were irrigated with either X8P or saline to simulate post-exposure decontamination. Irrigation of experimentally infected wounds with saline did not result in any apparent benefit. X8P irrigation of wounds infected with *B. cereus* spores showed substantial benefit, resulting in a consistent 98% reduction in the lesion size from 4.86 $cm^2$ to 0.06 $cm^2$. This reduction in lesion size was accompanied by a four-fold reduction in mortality (80% to 20%) when compared to experimental animals receiving either no treatment or saline irrigation.

Example 12

Effect Of Surfactant Lipid Preparations (SLPS) on Influenza a Virus Infectivity In Vitro The following example describes the effect of emulsions on Influenza A virus infectivity Enveloped viruses are of great concern as pathogens. They spread rapidly and are capable of surviving out of a host for extended periods. Influenza A virus was chosen because it is a well accepted model to test anti-viral agents (Karaivanova and Spiro, Biochem J. 329(Pt 3):511 [1998]. Mammen et al., J Med Chem 38:4179 [1995]). Influenza is a clinically important respiratory pathogen that is highly contagious and responsible for severe pandemic disease.

The envelope glycoproteins, hemagglutinin (HA) and neuraminidase (NA) not only determine the antigenic specificity of influenza subtypes, but they mutate readily and, as a result, may allow the virus to evade host defense systems. This may result in the initiation of disease in individuals that are immune to closely related strains. The following is a description of the methods and composition used for determining the efficacy of SLPs in preventing influenza A infectivity.

Surfactant lipid preparations (SLPs): The SLPs were made in a two-step procedure. An oil phase was prepared by blending soybean oil with reagents listed in Table 1 and heating at 86° C. for one hour (Florence, 1993). The SLPs were then formed by injecting water or 1% bismuth in water (SS) into the oil phase at a volume/volume ratio using a reciprocating syringe pump.

Viruses: Influenza virus A/AA/6/60 was kindly provided by Dr. Hunein F. Maassab (School of Public Health, University of Michigan). Influenza A virus was propagated in the allantoic cavaties of fertilized pathogen-free hen eggs (SPAFAS, Norwich, Conn.) using standard methods (Barrett and Inglis, 1985). Virus stock was kept in aliquots ($10^8$ pfu/ml) of infectious allantoic fluids at −80° C. Adenoviral vector (AD.RSV ntlacZ) was provided by Vector Core Facility (University of Michigan Medical Center, Ann Arbor, Mich.) and was kept in aliquots ($10^{12}$ pfu/ml at −80° C.). The vector is based on a human adenoviral (serotype 5) genomic backbone deleted of the nucleotide sequence spanning E1A and E1B and a portion of E3 region. This impairs the ability of the virus to replicate to transform nonpermissive cells. It carries the *E. coli* LacZ gene, encoding β-galactosidase under control of the promoter from the Rouse sarcoma virus long terminal repeat (RSV-LTR). The vector also contains a nuclear targeting (designated as nt) epitope linked to the 5' end of the LacZ gene to facilitate the detection of protein expression (Baragi et al., 1995).

Cells: Madin Darby Canine Kidney (MDCK) cells were purchased from the American Type Culture Collection (ATCC; Rockville, Md.) and 293 cells (CRL 1573; transformed primary embryonic human kidney) were obtained from the Vector Core Facility (University of Michigan Medical Center, Ann Arbor, Mich.). The 293 cells express the transforming gene of adenovirus 5 and therefore restore the ability of Ad.RSV ntlacZ vector to replicate in the host cell.

Cell maintenance media: MDCK cells were maintained in Eagle's minimal essential medium with Earle's salts, 2 mM L-glutamine, and 1.5 g/l sodium bicarbonate (Mediatech, Inc., Hemdon, Va.) containing 10% fetal bovine serum (FBS; Hyclone Laboratories, Logan, Utah). The medium was supplemented with 0.1 mM non-essential amino acids, 1.0 mM sodium pyruvate, 100 U penicillin/ml and streptomycin 100 μg/ml (Life Technologies, Gaithersburg, Md.). The 293 cells were maintained in Dulbecco's modified Eagle medium (Mediatech, Inc., Herndon, Va.), containing 2 mM L-glutamine, 0.1 mM non-essential amino acids, and 1.0 mM sodium pyruvate. It also contained 100 U penicillin/ml and streptomycin 100 μg/ml (Life Technologies, Gaithersburg, Md.) and was supplemented with 10% FBS (Hyclone Laboratories, Logan, Utah).

Virus infection media: Influenza A infection medium was the MDCK cell maintenance medium (without FBS) supplemented with 3.0 μg/ml of tolylsulfonyl phenylalanyl chloromethyl ketone (TPCK)-treated trypsin (Worthington Biochemical Corporation, Lakewood, N.J.). Adenovirus infection medium was 293T cell maintenance medium with a reduced concentration of serum (2% FBS).

Influenza A overlay medium: Overlay medium consisted of equal amounts of 2× infection medium and 1.6% SEAKEM ME agarose (FMC BioProducts, Rockland, Md.). Staining agarose overlay medium consisted of agarose overlay medium plus 0.01% neutral red solution (Life Technologies, Gaithersburg, Md.) without TPCK-treated trypsin.

Plaque reduction assays (PRA): The plaque reduction assay was performed with a modification of the method described elsewhere (Hayden et al., 1980). MDCK cells were seeded at $1\times10^5$ cells/well in 12-well FALCON plates and incubated at 37° C./5% $CO_2$ for 3 days. Approximately $1\times10^8$ pfu of influenza A virus was incubated with surfactant lipid preparations as described below. The influenza A virus-SLP treatments and controls were diluted in infection medium to contain 30-100 pfu/250 µl. Confluent cell monolayers were inoculated in triplicate on 3 plates and incubated at 37° C./5% $CO_2$ for 1 h. The inoculum/medium was aspirated and 1 ml of agarose overlay medium/well was added and plates were incubated at 37° C./5% $CO_2$ until plaques appeared. Monolayers were stained with the agarose overlay medium and incubation was continued at 37° C./5% $CO_2$. Plaques were counted 6-12 h after staining. The average plaque count from 9 wells with lipid preparation concentration was compared with the average plaque count of untreated virus wells.

In situ cellular enzyme-linked immunosorbent assay (ELISA): To detect and quantitate viral proteins in MDCK cells infected with influenza A virus, the in situ cellular ELISA was optimized. Briefly, $2\times10^4$ MDCK cells in 100 µl complete medium were added to flat-bottom 96-well microtiter plates and incubated overnight. On the next day, the culture medium was removed and cells were washed with serum free maintenance medium. One hundred µl of viral inoculum was added to the wells and incubated for 1 hour. The viral inoculum was removed and replaced with 100 µl of MDCK cell maintained medium plus 2% FBS. The infect MDCK cells were incubated for an additional 24 h. Then the cells were washed once with PBS and fixed with ice cold ethanol:acetone mixture (1:1) and stored at −20° C. On the day of the assay, the wells of fixed cells were washed with PBS and blocked with 1% dry milk in PBS for 30 min. at 37° C. One hundred µl of ferret anti-influenza A virus polyclonal antibody at 1:1000 dilution (kindly provided by Dr. Hunein F. Maassab, School of Public Health, University of Mich.) was added to the wells for 1 hr at 37° C. The cells were washed 4 times with washing buffer (PBS and 0.05% TWEEN-20), and incubated with 100 µl at 1:1000 dilution of goat anti-ferret peroxidase conjugated antibody (Kirkegaard & Perry Laboratories, Gaithersburg, Mass.) for 30 min. at 37° C. Cells were washed 4 times and incubated with 100 µl of 1-STEP TURBO TMB-ELISA substrate (Pierce, Rockford, Ill.) until color had developed. The reaction was stopped with 1 N sulfuric acid and plates were read at a wavelength of 450 nm in an ELISA microtiter reader.

β-galactosidase assay: β-galactosidase assay was performed on cell extracts as described elsewhere (Lim, 1989). Briefly, 293 cells were seeded on 96-well "U"—bottom tissue culture plates at approximately $4\times10^4$ cells/well and incubated overnight at 37° C./5%$CO_2$ in maintenance medium. The next day, the medium was removed and the cells were washed with 100 µl Dulbecco's phosphate buffered saline (DPBS). Adenovirus stock was diluted in infection medium to a concentration of $5\times10^7$ pfu/ml and mixed with different concentrations of X8P as described below. After treatment with X8P, virus was diluted with infection medium to a concentration of $1\times10^4$ pfu/ml and overlaid on 293 cells. Cells were incubated at 37° C./5% $CO_2$ for 5 days, after which the plates were centrifuged, the medium was removed and the cells were washed three times with PBS without Ca++ and Mg++. After the third wash, the PBS was aspirated and 100 µl of 1× Reporter Lysis Buffer (Promega, Madison, Wisc.) was placed in each well. To enhance cell lysis, plates were frozen and thawed three times and the β-galactosidase assay was performed following the instruction provided by the vendor of β-galactosidase (Promega, Madison, Wisc.) with some modifications. Five microliters of cell extract was transferred to a 96-well flat bottom plate and mixed with 45 µl of 1× Reporter Lysis Buffer (1:10). Subsequently 50 µl of 2× assay buffer (120 mM $Na_2HPO_4$, 80 mM $NaH_2PO_4$, 2 mM $MgCl_2$ mM β-mercaptoethanol, 1.33 mg/ml ONPG (Sigma, St. Louis, Mo.) were added and mixed with the cell extract. The plates were incubated at RT until a faint yellow color developed. At that time the reaction was stopped by adding 100 µl of 1 M sodium bicarbonate. Plates were read at a wavelength of 420 nm in an ELISA microplate reader. The units of β-galactosidase in each cell extract was calculated by regression analysis by reference to the levels in the standard and divided by milligrams of protein in the cell extract sample.

Cellular toxicity and virus treatment with lipid preparations: Prior to viral susceptibility testing, cytotoxicity of SLPs on MDCK and 293 cells was assessed by microscope inspection and MTT assay. The dilutions of the mixture of virus and SLPs applied in susceptibility testing were made to be at least one order of magnitude higher than the safe concentration of SLP assessed. Approximately $1\times10^8$ pfu of either influenza A or adenovirus were incubated with lipid preparation at final concentrations of 1:10, 1:100, and 1:1000 for different time periods as indicated in results on a shaker. After incubation, serial dilutions of the SLP/virus mixture were made in proper infection media and overlaid on MDCK (influenza A) or 293 (adenovirus) cells to perform PRA, cellular ELISA or β-galactosidase assays as described above.

Electron microscopy: Influenza A virus was semi-purified from allantoic fluid by passing through a 30% sucrose cushion prepared with GTNE (glycine 200 mM, Tris-HCl 10 mM (pH 8.8), NaCl 100 mM, and EDTA 1 mM) using ultra centrifugation (Beckman rotor SW 28 Ti, at 20,000 rpm for 16 hours). Pelleted virus was reconstituted in GTNE. Ten microliters of respective samples (adenovirus, influenza virus, adenovirus+X8P, influenza virus+X8P) were incubated for 15 and 60 min, then placed on parlodian coated 200 mesh copper grids for 2 min. Five µl of 2% cacodylated-buffered glutaraldehyde was then added. The fluid was removed with filter paper after 3 min. Ten microliters of 7% uranyl acetate was added to the grid and drawn off with filter paper after 30 sec. The grids were allowed to dry 10 min and examined on a Philips EM400T transmission electron microscope. Micrographs were recorded in Fuji FG film at magnifications of 200,000×.

Susceptibility testing of influenza A to SLPS: The effect of four surfactant lipid preparations (X8P, NN, $W_{80}8P$, and SS) on influenza A infection of MDCK cells was investigated. All tested preparations inhibited influenza A virus infection to varying degrees. X8P and SS exhibited over 95% inhibition of influenza infection at a 1:10 dilution. NN and $W_{80}8P$ showed only an intermediate effect on influenza A virus, reducing infection by approximately 40%. X8P's virucidal effect was undiminished even at a 1:100 dilution. SS showed less effect at a 1:100 dilution inhibiting influenza A infection by 55%. These two lipid preparations at 1:1000 dilution displayed only weak inhibitory effect on virus infectivity at the range of 22-29%.

Since X8P and SS both showed storing strong inhibitory effect on virus infectivity, PRA was used to verify data obtained from cellular ELISA. PRA confirmed the efficacy of X8P and SS. X8P reduced the number of plaques from an average of 50.88 to 0 at a 1:10 dilution (Table 23). At dilution 1:100, X8P maintained virucidal effectiveness. At dilution 1:100 SS reduced the number of plaques only approximately 7% as compared with untreated virus.

TABLE 23

| Treatment Dilution of the agent: | Plaque forming units X8P | Plaque forming units SS |
|---|---|---|
| 1:10[a] | 0.00[b] (+/−0.00)[c] | 0.00 (+/−0.00) |
| 1:100 | 0.00 (+/−0.00) | 1.55 (+1−0.12) |
| Untreated virus | 50.88 (+/−1 − 0.25) | 23.52 (+/−0.18) |

[a]Virus was incubated with SLPs for 30 minutes.
[b]Number of plaques.

Kinetics of X8P action on influenza A virus: To investigate the time requirement for X8P to act on influenza A infectivity, virus was incubated with X8P at two dilutions (1:10, 1:100) and four different time intervals (5, 10, 15, 30 min). Subsequently, a plaque reduction assay was performed. As shown in Table 24, after five min of incubation with X8P at either dilution, influenza A virus infectivity of MDCK cells was completely abolished. There was no significant difference between the interaction of X8P with influenza A virus regardless of concentration or time.

TABLE 24

Plaque Forming Units after X8P Treatment/Dilution

| Time (min) | 1:10 | 1:100 | untreated |
|---|---|---|---|
| 5 | 0.00[a] (+/−0.00)[b] | 0.00 (+/−0.00) | 35.25 (+/−0.94) |
| 10 | 0.00 (+/−0.00) | 0.25 (+/−0.12) | 39.25 (+/−1.95) |
| 15 | 0.00 (+/−0.00) | 0.25 (+/−0.12) | 31.50 (+/−1.05) |
| 30 | 0.00 (+/−0.00) | 0.00 (+/−0.00) | 26.50 (+/−0.08) |

Anti-influenza A efficacy of X8P: Since TRITON X-100 detergent has anti-viral activity (Maha and Igarashi, Southeast Asian J Trop Med Public Health 28:718 [1997]), it was investigated whether TRITON X-100 alone or combined with individual X8P components inhibits influenza A infectivity to the same extent as X8P. Influenza A virus was treated with: 1) X8P, 2) the combination of tri(n-butyl) phosphate, TRITON X-100, and soybean oil (TTO), 3) TRITON X-100 and soybean oil (TO), or 4) TRITON X-100 (T) alone. X8P was significantly more effective against influenza A virus at 1:10 and 1:100 dilutions (TRITON X-100 dilution of 1:500, and 1:5000) than TRITON X-100 alone or mixed with the other components tested. At the dilution 1:1000, X8P (TRITON X-100 dilution of 1:50,000) was able to reduce influenza A infection of MDCK cells by approximately 50% while TRITON X-100 alone at the same concentration was completely ineffective.

X8P does not affect infectivity of non-enveloped virus: To investigate whether X8P may affect the infectivity of non-enveloped virus, genetically engineered adenovirus containing LacZ gene was used, encoding β-galactosidase. This adenovirus construct is deficient in the transforming gene and therefore can replicate and transform only permissive cells containing the transforming gene of adenovirus 5. The 293 cells, which constitutively express transforming gene, were employed to promote adenovirus replication and production of β-galactosidase enzyme. X8P treatment did not affect the ability of adenovirus to replicate and express β-galactosidase activity in 293 cells. Both X8P treated and untreated adenovirus produced approximately 0.11 units of β-galactosidase enzyme.

Action of X8P on enveloped virus: Since X8P only altered the infectivity of enveloped viruses, the action of this nanoemulsion on enveloped virus integrity was further investigated using electron microscopy. After a 60 min incubation with 1:100 dilution of X8P, the structure of adenovirus is unchanged. A few recognizable influenza A virions were located after 15 min incubation with X8P, however, no recognizable influenza A virions were found after 1 h incubation. X8P's efficacy against influenza A virus and its minimal toxicity to mucous membranes demonstrates its potential as an effective disinfectant and agent for prevention of diseases resulting from infection with enveloped viruses.

Example 13

The Ability of Nanoemulsion/Influenza Compositions to Induce an Immune Response in Mice This Example describes the ability of an exemplary nanoemulsion composition to elicit a specific immune response in mice.

A. The Effect of Pre-treatment with Nanoemulsion on Immune Response to Influenza A Mice were pretreated with nasally-applied nanoemulsion (1.0% 8N8 and 1.0% or 0.2% 20N10) 90 minutes before exposure to influenza virus ($5 \times 10^5$ p.f.u./ml) by nebulized aerosol. Morbidity from pretreatment with nanoemulsion was minimal and, as compared to control animals, mortality was greatly diminished (20% with pretreatment vs. 80% in controls, Donovan et al., Antivir Chem Chemother., 11:41 [2001]). Several of the surviving, emulsion pretreated animals had evidence of immune reactivity and giant-cell formation in the lung that were not present in control animals with emulsion but not exposed to virus. All of the pretreated animals had evidence of lipid uptake in lung macrophages.

FIG. 6 shows serum anti-influenza titers in mice treated with different preparations of virus. Only animals whose narcs were exposed to virus/nanoemulsion show significant IgG titers. In animals exposed to virus without pretreatment or emulsion alone, no immune response to influenza virus was observed. Antibody titers to influenza virus in the serum of exposed animals was measured and found that animals pretreated with emulsion and exposed to virus had high titers of virus-specific antibody (FIG. 6). This immune response was not observed in control animals exposed to virus without pretreatment. The high titers of antibody in these animals prompted experiments to determine whether or not the co-administration of emulsion and virus would yield protective immunity without toxicity.

B. The Effect of Nanoemulsion/Influenza a Virus Co-administration on Immune Response X8P emulsion was pre-mixed with the virus. The final emulsion concentration was 2% and virus concentration was $2 \times 10^6$ pfu/ml. The emulsion/virus solution (25 μl) of the emulsion/virus solution was administered to the narcs of mice under mild anesthesia. A control group received the same viral dose inactivated using 1:4000 dilution of formaldehyde solution incubated for 3 days to ensure complete inactivation. Another control group included mice that received a reduced dose of virus (100 pfu/mouse). Additional controls received nanoemulsion alone or saline alone.

Three weeks later, mice received a second dose of the emulsion/virus vaccine. Representatives of the group were tested for the development of serum antibodies and some were challenged with a lethal dose of influenza A virus to check for any developed immunity. Two weeks later, mice were tested for the development of a protective immune response in their serum. Some mice were challenged with a lethal dose of influenza virus to check for the development of protective immunity. All the challenged mice were observed for 14 days for signs of disease. Sera were tested for the presence of specific antibodies against influenza virus.

The results of the experiment are shown in Table 25 and FIGS. 7-8. None of the 15 animals died from exposure to a LD80 of virus after two administrations of $5 \times 10^4$ pfu of virus mixed in nanoemulsion, whereas the expected 80% of control animals died from this exposure. The same dose of formalin killed virus applied to the narcs provided no protection from death and resulted in much lower titers of virus-specific antibody.

FIG. 7 shows bronchial IgA anti-influenza titers in mice treated with different preparations of virus. Animals whose narcs were exposed to virus/nanoemulsion show significant IgA titers. In animals exposed to killed virus or emulsion alone, a much lower IgA titer was observed.

FIG. 8 shows serum anti-influenza titers in mice treated with two doses of several different preparations of virus. As compared to the animals in FIG. 6, the titers are much higher, particularly in the virus/emulsion treated animals. This indicates a "booster" response to the second administration. This example demonstrate that the administration of both nanoemulsion and killed virus is both necessary and sufficient to elicit a specific immune response in mice.

TABLE 25

Mortality of Influenza Exposed Animals Receiving Intranasal Pretreatment

| | Mortality | Death (%) |
|---|---|---|
| No Pre-treatment ($5\times10^4$ pfu) | 13/15 | 87 |
| Emulsion Alone | 12/15 | 80 |
| Formalin Killed Virus ($5\times10^4$ pfu) | 10/15 | 75 |
| Emulsion and Virus | 0/15 | 0 |
| Reduced Virus alone (100 pfu) | 6/15 | 40 |

Additional experiments were performed to investigate the possibility that a small amount of residual, live virus in the nanoemulsion was producing a subclinical infection that provided immunity. An additional group of animals were given approximately 100 pfu of live virus intranasally in an attempt to induce a low-level infection (approximately four times the amount of live virus present after 15 minutes of treatment with nanoemulsion). While there was a reduction in death rates of these animals, the amount of protection observed was insignificant and none of these animals developed virus-specific antibodies (Table 25). This result indicates that it was not merely a sub-lethal viral infection mediating the immune response but that the emulsion was specifically enhancing the virus-specific immune response. The protective immunity was obtained following only two applications (immunizations) of the emulsion/virus mix, and appeared to increase after each application suggesting a "booster effect." Virus-specific antibody titers were maintained for six weeks until the end of the experiment.

Example 14

Testing of Nanoemulsion Vaccines

This Example describes experiments useful in testing potential nanoemulsion vaccines for their safety and efficacy.

A. Pre-exposure Prophylaxis and Induction of Immunity

Intranasal prophylaxis: 6 groups of animals (Table 26) receive the following schedule of treatments intranasally with 15-60 minute intervals in between. Animals are monitored for any sign of diseases. Blood, broncho-alveolar lavage fluid and nasal washing are collected and tested for pathogen specific antibody titer using ELISA (Fortier et al., [1991]; Jacoby et al., [1983], and Takao et al., [1997]). Two weeks later, surviving animals are challenged with a lethal dose of the pathogen to test for the development of a protective immune-response. Terminally ill animals are sacrificed humanely as soon as identified, as are all other animals at the end of the experiment (at least two weeks after the challenge). Blood and tissue are harvested for histopathological examination and both the serologic and cell-mediated immune responses are determined.

TABLE 26

Treatment Groups of Animal in Exposure Trials

| Group | Pre-treatment | Treatment |
|---|---|---|
| 1 | Diluted Nanoemulsion | Live Pathogen |
| 2 | Diluted Nanoemulsion | Formalin Killed Pathogen |
| 3 | Diluted Nanoemulsion | PBS |
| 4 | PBS | Live Pathogen |
| 5 | PBS | Formalin Killed Pathogen |
| 6 | PBS | PBS |

B. Evaluation of the Adjuvant Activity of the Nanoemulsion

Cell-mediated immune responses are evaluated in vitro. The evaluation is performed on immunocompetent cells harvested from euthanized animals obtained from the experiment described above (section A). T-cells proliferation response is assessed after re-stimulation with antigen. Cells are re-stimulated with whole pathogen or pathogen constituents such as DNA, RNA or proteins alone or mixed with nanoemulsion. Proliferation activity is measured by H3-thymidine uptake or Cell Proliferation ELISA chemiluminiscene. In addition to proliferation, Th1 and Th2 cytokine responses are measured to qualitatively evaluate the immune response. These include IL-2, TNF-γ, IFN-γ, IL-4, IL-6, IL-11, IL-12, etc.

Proliferation and cytokine response patterns are compared with the results obtained in Section A above. After careful analysis of the data, nanoemulsions are modified by substituting specific components with other oil, detergents or solvents. Other desired adjuvants such as CpG, chemokines and dendrimers are added to the emulsion/pathogen mix to evaluate their enhancement of immune responses, along with potential toxicity.

C. Development of Rapid and Effective Mucosal Vaccines

This example provides a non-limiting example of methods for testing the nanoemulsion vaccines of the present invention. Intranasal vaccination: Animals are divided into 6 groups, Each group receives a different intranasal challenge to evaluate the resulting immune response:

1. Nanoemulsion alone (Negative control)
2. Pathogen alone (Positive control).

3. Nanoemulsion/pathogen mixture, prepared immediately prior to administration.
4. Nanoemulsion/pathogen mixture, prepared 3 days before administration.
5. Formaldehyde killed pathogen.

Table 27 shows the challenge protocol for vaccine studies. All challenged animals are monitored daily for any signs of illness. Serum is tested for pathogen specific antibody titer using ELISA (Fortier et al., Infect. Immun., 59:2922 [1991], Jacoby et al., Lab. Anim. Sci., 33:435 [1983], and Takao et al., J. Virol., 71:832 [1997]). Any terminally ill animals are humanely euthanized, with serum harvested for antibody titer and tissues collected for histopathologic examination. Harvested spleen cell and lymph node cell suspensions are used to determine cell-mediated immune responses. At the end of the experiment, all remaining animals are humanely sacrificed for similar analysis.

TABLE 27

Challenge Protocol for Vaccine Studies

| Day | Procedure |
|---|---|
| 0 | Start of the treatment for all groups. |
| 14 | Blood samples are collected from all the animals. One group of animals is sacrificed for BAL, nasal washing, organs and histopathology. One group of animals is challenged with a lethal dose of the pathogen. The rest of the animals receive second dose of the emulsion/vaccine treatment. |
| 35 | Blood samples are collected from all the animals. One group of animals is sacrificed for BAL, nasal washing, organs and histopathology. One group of animals is challenged with a lethal dose of the pathogen. |
| 49 | Blood samples are collected from all the animals. The remaining animals are sacrificed for BAL, nasal washing, organs and histopathology. |

Example 15

Protection of Mice from Viral Pneumonitis after Intranasal Immunization with Influenza a and Nanoemulsion A. Material and Methods Animals Female C3H/HeNHsd (Harlan, Indianapolis, Ind.) 5-week-old, specific-pathogen-free mice were used in all experiments.

Virus

Influenza A/Ann Arbor/6/60 virus (H2N2), mouse adapted, $F_{-14-95}$, $E_1$, $M_3$, $E_1$, $SE_1$ was provided by Dr. Hunein Maassab (School of Public health, University of Michigan, Ann Arbor, Mich.). Influenza A/Puerto Rico/8/34 virus (H1N1), mouse adapted, $F_8$, $M_{593}$, $E_{173}$, $SE_1$ was from ATCC (Rockville, Md.). All viruses were propagated in allantoic cavities of fertilized pathogen-free hen eggs (SPAFAS, Norwich, Conn.) using standard methods described elsewhere (Herlocher et al., Virus Res., 42:11 [1996]). Virus stocks were kept in aliquots of infectious allantoic fluids at −80° C. The virus was purified on sucrose gradient 15-60% solution at 100,000 g for 90 min at 4° C., as described previously (Merton et al., Production of influenza virus in cell cultures for vaccine preparation. In: Novel Strategies in Design and Production of Vaccines. Edited by S. Cohen and A. Shafferman, Plenum Press, New York, 1996. pp. 141-151). The band containing the virus was collected, diluted in NTE buffer (100 mM NaCl, 10 mM Tris-HCl, 1 mM EDTA, pH=7.5) and spun down at 100,000× g for 60 min at 4° C. The virus pellet was resuspended in NTE buffer and stored at −80° C.

Inactivation of Virus With Formaldehyde

Virus inactivation was performed as previously described (Chen et al., J. Virol 61:7 [1987] Novak et al., Vaccine 11:1 [1993]). Briefly, different doses ($10^3$–$10^5$ pfu) of virus were incubated in formaldehyde solution (dilution 1:4000) for 3 days and subsequently administered to animals.

Inactivation of Virus With X8P Nanoemulsion

Intact influenza A virus at various concentrations of $2\times10^4$–$5\times10^5$ pfu was mixed with equal volume of 4% X8P nanoemulsion (final concentration: 2%) and incubated at 37° C. for 60 min.

Preparation of Nanoemulsion and Toxicity Testing

The X8P surfactant nanoemulsion was prepared in a two-phase procedure. An oil phase was prepared by blending the following ingredients: TBP (final concentration 8%), TRITON X-100 (4-(1,1,3,3-Tetramethylbutyl)phenvl-polyethylene glycol) (8%) and soybean oil (64%) and heating at 700° C. for 30 minutes (See e.g., U.S. Pat. No. 6,015,832 and U.S. patent application 20020045667, each of which is herein incorporated by reference). The surfactant nanoemulsion was then formed by mixing with water (20%) using a Silverson ART Mixer for 3 minutes at 10,000 rpm. TRITON X-100 was purchased from Sigma Chemicals (St. Louis, Mo.), TBP was purchased from Aldrich (Milwaukee, Wis.), and soybean oil was purchased from Croda Inc. (Mill Hill, Pa.). The X8P nanoemulsion was tested for animal toxicity as previously described (See e.g., above examples). Briefly, the mice were anesthetized with metofane and different concentrations of nanoemulsion (1, 2, and 4%) at a volume of 50 µl (25 µl/nare) were administrated to mice intranasally. All tested concentrations of nanoemulsion were well tolerated after direct intranasal instillation in mice. Based on these data, 2% X8P was chosen for the immunization study.

Plaque and Plaque reduction Assays

Plaque assays (PA) were performed on MDCK monolayer cells in six-well plates as previously described (Myc et al., J. Virol. Meth. 77:165 [1999]). Plaque reduction assays (PRA) were performed with a modification of the method described by Hayden et al. (Antimicrob. Agents and Chemother., 17:865 [1980]). MDCK cells were grown in 150×25 mm petri dishes to 80% confluency. Approximately $1\times10^8$ pfu influenza A virus was incubated either with nanoemulsion of PBS for 30 min at room temperature (RT). After incubation, nanoemulsion-treated and untreated virus were resuspended in 250 ml medium and the entire volume of viral suspension was placed on separate cell monolayers and incubated for 1 h, following the plaque assay method as previously described (Myc et al., supra).

Immunizations and Experimental Design

All groups of mice were treated intranasally with viral or control solutions in a total volume of 50 µl (25 µl/nare) as described in the Results section below. Briefly, each mouse was halothane anesthetized and held inverted with the nose down until droplets of emulsion applied to external narcs were completely inhaled. All mice were treated once on day 1 of the experiment. On day 21, mice were challenged with $LD_{100}$ either with congenic virus (used for intranasal treatment) or heterogenic virus. After the challenge, mice were monitored daily for clinical signs of illness for 14 days. Clinical signs of illness were graded on a scale of 0-3, where 0 indicated no significant clinical abnormality; 1 indicated mild symptoms including piloerection, hunched back and loss of movement; 2 indicated cyanosis, dyspnea, circulatory compromise tachypnea and rectal temperatures <33° C.; and 3 indicated death of the animal. Rectal core body temperatures were recorded with a Model BAT-12 digital thermometer fitted with a RET-3 type T mouse rectal probe (Physitem, Clifton, N.J.) Rozen et al., Meth. Mol. Biol., 132:365 [2000]). Mice with core body temperatures falling below 33° C. were judged to be terminally moribund and humanely euthanized (Stevenson et al., J. Immunol., 157:3064 [1996]). Mice that survived 14 days after challenge had normal body temperatures and no clinical signs of illness.

Collection of Blood and Tissue Samples

Blood samples were obtained either from the tail vein or from euthanized animals by cardiac puncture at different time intervals during the course of experiment. Samples of lungs, regional lymph nodes, spleen, and liver were collected from euthanized animals and processed following the RT PCR or proliferation assay protocols as described below.

RT-PCR Detection of Viral RNA

The following primers for 246 bp fragment of M gene, conserved for A strains, were used for PCR:5' catggaatg-gctaaagacaagacc (forward; SEQ ID NO:1), and 5'aagtgcac-cagcagaataactgag (reverse; SEQ ID NO:2), as described previously (Schweiger et al., J. Clin. Microbiol., 38:1552 [2000]). The primers were ordered from Operon Technologies, Inc. (Alameda, Calif.). Viral RNA was isolated from tissue homogenates with the use of Tri Reagent (MRC. Cincinnati, Ohio). Lung, mediastinal lymph node, spleen and liver were used for RNA extraction. The cDNA synthesis was carried out with 2.0 µg of total tissue RNA using 5.0 mM $MgCl_2$ 500 µM of each dNTP, 2.5 µM random hexamer primers, 0.4 U/µl of RNase inhibitor and 2.5 U/µl of Superscript II RT (Invitrogen, Rockville, Md.). Thermal cycling was performed in a total volume of 20µ using 3 single cycles at 25° C. for 12 min, at 42° C. for 50 min, then 70° C. for 15 min (GeneAmp PCR System 2400/Perkin Elmer). The PCR amplification was carried out with 0.01-0.1µg of cDNA using 0.2 µM of each primer, 0.2 mM of each dNTP, 1.5 mM $MgCl_2$, 0.1 U/µl of Taq DNA Polymerase (Roche Molecular Biochemicals, Indianapolis, Ind.). PCR reactions in a total volume of 20 µl were incubated at 94° C. for 2 min, and then 35 cycles were performed with annealing at 62° C., extension at 72° C. and denaturation at 94° C. Post-PCR analysis was performed on a 2% Nusive/1% agarose gel using Tris-acetate buffer for electrophoresis and ethidium bromide for DNA staining. Analysis was performed using a photoimaging camera and software from BioRad (Hercules, Calif.).

Specific Anti-virus IgG Determination

IgG-specific Ab titers were determined in ELISA. Microtiter plates (NUNC) were pretreated with 0.5% glutaraldehyde (Sigma, St. Louis, Mo.) in PBS for one hour at 56° C. and washed 4 times with PBS. Influenza A virus ($5 \times 10^3$ pfu/well) in PBS was placed on the pre-treated plates and incubated wither at 37° C. for two hours or overnight at 4° C. The virus was aspirated; plates were washed with PBS and fixed with ethanol-acetone (1:1) fixative for 15 min at −20° C. After fixation, plates were washed again and blocked for 30 min with blocking buffer (1% dry milk in PBS). Blocking buffer was removed and plates were sealed and stored at 4° C. until used. Serum samples and positive and negative control sera were serially diluted in dilution buffer 0.1% BSA in PBS) and incubated on virus coated plates at 37° C. for 30 min. After washing with washing buffer (0.05% Tween 20 in PBS), biotinylated anti-mouse IgG antibody was added and plates were incubated at 37° C. for 30 min. Plates were washed again and incubated with streptavidin-AP (Sigma, St. Louis, Mo.), following wash and incubation with AP substrate (Sigma, St. Louis, Mo.). Plates were incubated at room temperature until color developed. The reaction was stopped with 1 N NaOH and the plates were read on an ELISA reader at 405 nm. Antibody titers were determined arbitrarily as the highest serum dilution yielding absorbency three times above the background (Kremer et al., Infection and Immunity 66:5669 [1998]).

Proliferation Assay

Mouse spleens were disrupted in PBS to obtain the single cell suspension. Cells were washed in PBS and red blood cells were lysed using ammonium chloride lysis buffer. Splenocytes were then resuspended in the culture medium (RPMI 1640 supplemented with 10% FBS, I-glutamine and penicillin/streptomycin) and seeded $1.5 \times 10^5$ cells/250 µl/well in 96-well microtiter plate. Cells were then incubated wither with the mitogen PHA-P (2.5 µg/well) for 3 days (Stevenson et al., supra) or influenza A virus at concentration of $6 \times 10^3$ pfu/well for 6 days, following overnight BrdU labeling. Cell proliferation was measure using a Cell Proliferation Chemiluminiscene ELISA following the manufacturer's instruction (Roche Diagnostics, Indianapolis, Ind.) Measurement of relative light units was performed using a standard luminometer.

In Vitro Cytokine Production

Splenocytes were resuspended in culture medium (RPMI 1640 supplemented with 10% FBS, L-glutamine and penicillin/streptomycin) and seeded $1.5 \times 10^5$ cells/250 µl/well in microtiter flat-bottom plates. Cells were then incubated wither with the mitogen PHA-P (2.5 µg/well) for 3 days (Stevenson et al., supra) or influenza A virus at a concentration of $6 \times 10^3$ pfu/well for 6 days. Supernatant was then harvested and subjected to quatitate cytokine concentration.

Quantitation of Cytokines

IL-2, IL-4, IL-12, and IFN-γ cytokine levels in serum and splenocyte supernatants were performed using QUANTIKINE M ELISA kits (R&D Systems, Inc.) according to manufacturers' instructions.

Flow Cytometric Analysis

Antibodies specific to mouse molecules CD3, CD4, CD8 and CD19 (BD PharMingen, San Diego, Calif.) directly labeled with either PE or FITC were used in flow cytometric analysis. Single cell suspensions of splenocytes were incubated with antibodies for 30 min on ice and washed with PBS containing 0.1% BSA. Samples were acquired on a Coulter EPICS-XL MCL Beckman-Coulter flow cytometer and data were analyzed using Expo32 software (Beckman-Coulter, Miami, Fla.).

Histology

Lungs were fixed by inflation with 1 ml of 10% neutral buffered formalin, excised en bloc and immersed in neutral buffered formalin. After paraffin embedding, 5 µm sections were cut and stained with hematoxylin and eosin, and viewed by light microscopy.

Statistical Methods

The means, standard deviation, standard error and $\chi^2$ analysis with Yate's correction were calculated. To compare the control group to the study groups, Cox regression was used (Cox et al., Journal of the Royal Statistical Society.

Series B, 34:187 [1972]). The difference between the study groups and the control group was tested using the log-likelihood ratio test.

B. Results

Virucidal Activity of Nanoemulsion on Influenza a Virus

The virucidal effect of X8P nanoemulsion on influenza A virus, Ann Arbor strain was tested prior to intranasal treatment of animals with the virus/nanoemulsion mixture. The virus at concentrations of $2 \times 10^4$, $5 \times 10^4$ $2 \times 10^5$ and $5 \times 10^5$ pfu in 2% X8P nanoemulsion in a total volume of 50 µl was incubated at 37° C. for 60 min prior to inoculation of influenza-sensitive cells. The plaque reduction quality of the nanoemulsion was assayed using MDCK cells. As shown in FIG. 10a, nanoemulsion reduced the ability of virus to form plaques by more than three logs. Prolonged incubation of virus with nanoemulsion reduced number of plaque forming units in a time dependent manner (FIG. 10b). After 3-hour incubation of $5 \times 10^5$ pfu of virus with nanoemulsion, no pfu were detected (FIG. 10b). RT-PCR performed on virus/nanoemulsion preparation at the same time points showed complete correlation with plaque reduction assay (PRA). Viral RNA was still detectable at 2 h but non was present at 3 and 4 h (FIG. 10c).

Influenza a Virus/nanoemulsion Mixture Protects Mice From Lethal Challenge With Congenic Strain of Virus Mice were treated intranasally with either 2% nanoemulsion alone, formalin killed influenza A virus "AA" strain ($5\times10^5$ pfu), formalin killed virus mixed with 2% nanoemulsion or virus ($5\times10^5$ pfu) inactivated with 2% nanoemulsion. Twenty days later all 4 experimental groups were challenged with a lethal dose ($2\times10^5$ pfu) of the congenic virus. The animals treated with influenza/nanoemulsion mixture did not have any signs of illness; their core body temperature was within a normal range until the term of experiment (FIG. 11) and all animals survived the challenge. Animals treated with nanoemulsion alone succumbed to viral pneumonitis after the challenge and all died by day 27 (day 6 after challenge). All animals treated with formalin-killed virus and nanoemulsion died by day 26 (day 5 after challenge). In the group treated with formalin-killed virus alone only one mouse survived (FIG. 12).

The experiment also examined whether viral RNA mixed with nanoemulsion and administrated intranasally would protect mice from the lethal challenge. Neither viral RNA (0.5 μg; an equivalent of $10^5$ pfu of virus) alone nor viral RNA/nanoemulsion mixture had any protective effect on animals challenged with lethal dose of virus.

In order to examine whether intact virus particles could mimic the same protection effect an nanoemulsion/virus mixture, the animals were treated with 5 doses of virus ($2\times10^5$, $2\times10^4$, $2\times10^3$, $2\times10^2$, and $2\times10^1$ pfu) alone or mixed with nanoemulsion (Tables 28 and 29). Within the first 14 days after treatment, all animals treated with $2\times10^5$ pfu virus succumbed to pneumonitis. Only one mouse survived the treatment with $2\times10^4$ pfu virus. All animals in other experimental groups survived the treatment and became healthy 14 days later. On day 21 all survived animals were challenged with lethal dose of the virus and observed for additional 14 days. The mice treated with $5\times10^5$ pfu of virus and nanoemulsion survived the challenge; in the group of animals pretreated with $2\times10^5$ pfu of virus and nanoemulsion only 4 out of 7 mice survived. Animals from all other experimental groups developed pneumonities and all died by day 28.

TABLE 28

| | Intranasal treatment | | | | | | |
|---|---|---|---|---|---|---|---|
| Time (days) | X8P 0 | X8P $5\times10^5$ pfu | X8P $2\times10^5$ pfu | $2\times10^5$ pfu | X8P $2\times10^4$ pfu | $2\times10^4$ pfu | X8P $2\times10^3$ pfu |
| 0 | 5 | 6 | 7 | 8 | 7 | 9 | 7 |
| 1 | 5 | 6 | 7 | 7 | 7 | 9 | 7 |
| 2 | 5 | 6 | 7 | 3 | 7 | 9 | 7 |
| 3 | 5 | 6 | 7 | 0 | 7 | 2 | 7 |
| 4 | 5 | 6 | 7 | 0 | 7 | 1 | 7 |
| 5 | 5 | 6 | 7 | 0 | 7 | 1 | 7 |
| 6 | 5 | 6 | 7 | 0 | 7 | 1 | 7 |
| 7 | 5 | 6 | 7 | 0 | 7 | 1 | 7 |
| 8 | 5 | 6 | 7 | 0 | 7 | 1 | 7 |
| 9 | 5 | 6 | 7 | 0 | 7 | 1 | 7 |
| 10 | 5 | 6 | 7 | 0 | 7 | 1 | 7 |
| 11 | 5 | 6 | 7 | 0 | 7 | 1 | 7 |
| 12 | 5 | 6 | 7 | 0 | 7 | 1 | 7 |
| 13 | 5 | 6 | 7 | 0 | 7 | 1 | 7 |
| 14 | 5 | 6 | 7 | 0 | 7 | 1 | 7 |

| Time (days) | $2\times10^3$ pfu | X8P $2\times10^2$ pfu | $2\times10^2$ pfu | X8P $2\times10^1$ pfu | $2\times10^1$ pfu |
|---|---|---|---|---|---|
| 0 | 7 | 7 | 7 | 7 | 7 |
| 1 | 7 | 7 | 7 | 7 | 7 |
| 2 | 7 | 7 | 7 | 7 | 7 |
| 3 | 7 | 7 | 7 | 7 | 7 |
| 4 | 7 | 7 | 7 | 7 | 7 |
| 5 | 7 | 7 | 7 | 7 | 7 |
| 6 | 7 | 7 | 7 | 7 | 7 |
| 7 | 7 | 7 | 7 | 7 | 7 |
| 8 | 7 | 7 | 7 | 7 | 7 |
| 9 | 7 | 7 | 7 | 7 | 7 |
| 10 | 7 | 7 | 7 | 7 | 7 |

TABLE 28-continued

| | | | | | |
|---|---|---|---|---|---|
| 11 | 7 | 6 | 7 | 7 | 7 |
| 12 | 7 | 6 | 7 | 7 | 7 |
| 13 | 7 | 6 | 7 | 7 | 7 |
| 14 | 7 | 6 | 7 | 7 | 7 |

TABLE 29

| | Intranasal treatment | | | | | | |
|---|---|---|---|---|---|---|---|
| Time (days) | X8P 0 | X8P $5 \times 10^5$ pfu | X8P $2 \times 10^5$ pfu | X8P $2 \times 10^5$ pfu | X8P $2 \times 10^4$ pfu | $2 \times 10^4$ pfu | X8P $2 \times 10^3$ pfu |
| | | | Challenge with $2 \times 10^5$ pfu/mouse | | | | |
| 21 | 5 | 6 | 7 | | 7 | 1 | 7 |
| 22 | 5 | 6 | 7 | | 6 | 1 | 5 |
| 23 | 5 | 6 | 7 | | 6 | 1 | 5 |
| 24 | 5 | 6 | 7 | | 5 | 1 | 5 |
| 25 | 5 | 6 | 6 | | 5 | 1 | 4 |
| 26 | 1 | 6 | 6 | | 1 | 1 | 0 |
| 27 | 0 | 6 | 4 | | 0 | 1 | 0 |
| 28 | 0 | 6 | 4 | | 0 | 1 | 0 |
| 29 | 0 | 6 | 4 | | 0 | 0 | 0 |
| 30 | 0 | 6 | 4 | | 0 | 0 | 0 |
| 31 | 0 | 6 | 4 | | 0 | 0 | 0 |
| 32 | 0 | 6 | 4 | | 0 | 0 | 0 |
| 33 | 0 | 6 | 4 | | 0 | 0 | 0 |
| 34 | 0 | 6 | 4 | | 0 | 0 | 0 |
| 35 | 0 | 6 | 4 | | 0 | 0 | 0 |

| Time (days) | $2 \times 10^3$ pfu | X8P $2 \times 10^2$ pfu | $2 \times 10^2$ pfu | X8P $2 \times 10^1$ pfu | $2 \times 10^1$ pfu |
|---|---|---|---|---|---|
| 21 | 7 | 6 | 7 | 7 | 7 |
| 22 | 7 | 5 | 5 | 7 | 7 |
| 23 | 6 | 3 | 2 | 6 | 7 |
| 24 | 6 | 1 | 1 | 5 | 4 |
| 25 | 0 | 0 | 0 | 0 | 0 |
| 26 | 0 | 0 | 0 | 0 | 0 |
| 27 | 0 | 0 | 0 | 0 | 0 |
| 28 | 0 | 0 | 0 | 0 | 0 |
| 29 | 0 | 0 | 0 | 0 | 0 |
| 30 | 0 | 0 | 0 | 0 | 0 |
| 31 | 0 | 0 | 0 | 0 | 0 |
| 32 | 0 | 0 | 0 | 0 | 0 |
| 33 | 0 | 0 | 0 | 0 | 0 |
| 34 | 0 | 0 | 0 | 0 | 0 |
| 35 | 0 | 0 | 0 | 0 | 0 |

Lung Histology of Treated Mice

Histological examination of animals treated with nanoemulsion alone and challenged with a lethal dose of influenza A virus Ann Arbor strain ($5 \times 10^5$ pfu) showed profound lobar pneumonia at days 25-27 of experiment (day 5-7 post infection). Large areas of pulmonary tissue showed uniform consolidation caused by a massive influx of inflammatory cells (neutrophils and macrophages) filling the alveolar spaces and infiltrating the interstitium. Areas of pulmonary tissue destruction as evidenced by the intraalveolar bleeding, presence of abscesses with central necrosis, and by formation of empty caverns filled with traces of cellular debris were observed. Additionally, areas of fibrosis were found in the lungs of these mice, suggesting massive destruction of lung tissue that became replaced by proliferating fibroblasts. Thus, the histological picture of severe pneumonia and pulmonary tissue damage observed in these mice is consistent with rapid pulmonary death of animals caused by influenza infection.

Pathology of the virus-infected lungs from animals treated with intact virus/nanoemulsion mixture was less pronounced than pathology from the animals treated with nanoemulsion alone. In these animals both areas of pathologically unaltered lungs and areas with remaining pathology were found. Affected areas showed inflammatory infiltrates in lung interstitium (alveolar septa) but the alveolar space was free of exudates or inflammatory cells. The interstitial infiltrates contained predominantly mononuclear cells. The remaining lung tissue possessed well-preserved pulmonary architecture and appeared similar to the lungs from uninfected animals. This histological picture is consistent with less severe infection and recovery from infection observed in these mice.

Serum Levels of Specific Anti-influenza a Virus IgG

The levels of specific anti-influenza IgG antibodies were examined following a single treatment with either virus/nanoemulsion or nanoemulsion alone. The levels of IgG antibodies were evaluated in sera of animals on day 10, 20, and 35 after initial vaccination (or treatment). On day 10, all mice showed background levels of anti-influenza A IgG antibodies in serum (titer 1:100). On day 20, mice that had been treated with virus/nanoemulsion produced significantly higher antibody response ($p<0.05$) as compared to control group treated with nanoemulsion alone. On day 35, virus/nanoemulsion treated mice that survived the challenge produced 10 times higher serum levels of IgG antibody compared with the levels found within the same animals before the challenge (FIG. 13).

Detection of Viral RNA In Mice Treated With Influenza a Virus and Nanoemulsion Formulation.

The RT-PCR results from the total lung RNA indicated the presence of influenza A virus RNA in virus/nanoemulsion vaccinated animals until day 6 after treatment, but not on day 7 and thereafter (FIG. 14a). Signal generated in RT-PCR reaction from 0.1 µg of total RNA from mouse lung during the first 6 days after treatment correlated to a total of less than 10 plaque forming units (pfu) of virus (FIG. 14b).

Early Immune Status of Mice Immunized With Influenza a Virus/nanoemulsion Formulation The specificity of early immune responses in mice treated with various viral preparations was characterized by the analysis of cytokines. The level of cytokines produced by animals was measured both in media from cultured splenocytes and in serum of experimental animals (FIGS. 16a and 16b). On day 4 after treatment with virus/nanoemulsion preparation, elevated levels of IL-12, IL-2, TNF-$_\alpha$, and particularly IFN-$_\gamma$, were detected FIG. 16a). In the control group of animals, there were no detected levels of these cytokines. Elevated levels of IL-10 and no detectable levels of IL-4 were observed across all experimental groups.

Figure 15A:
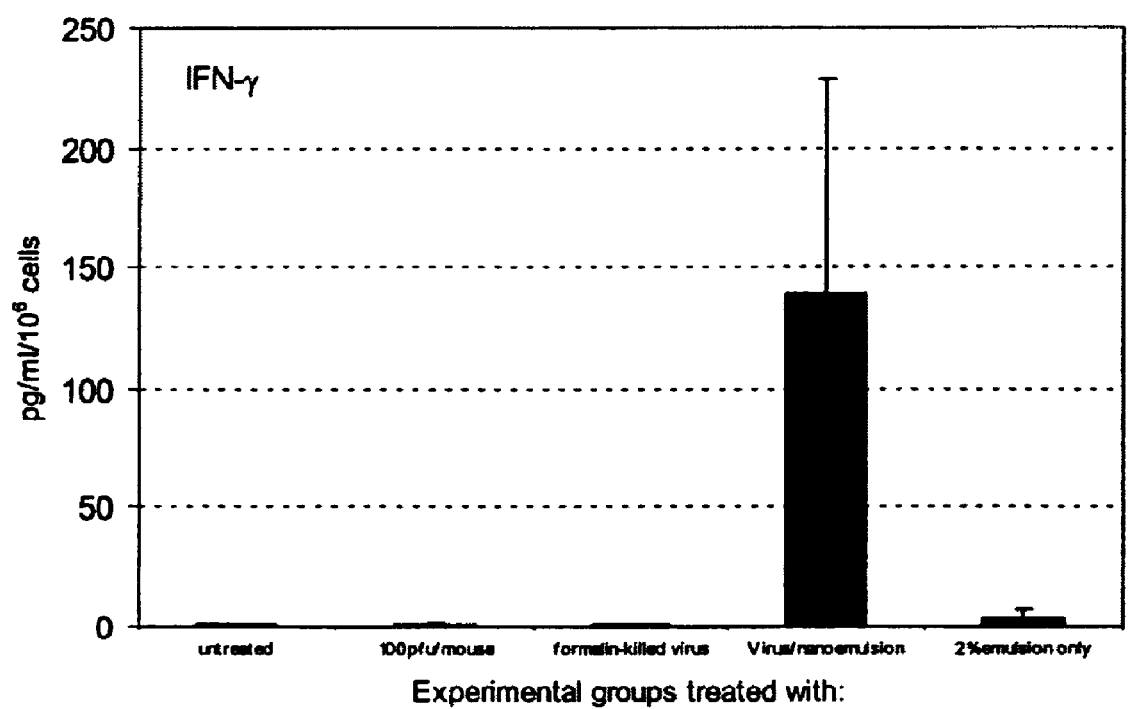
Figure 15B:
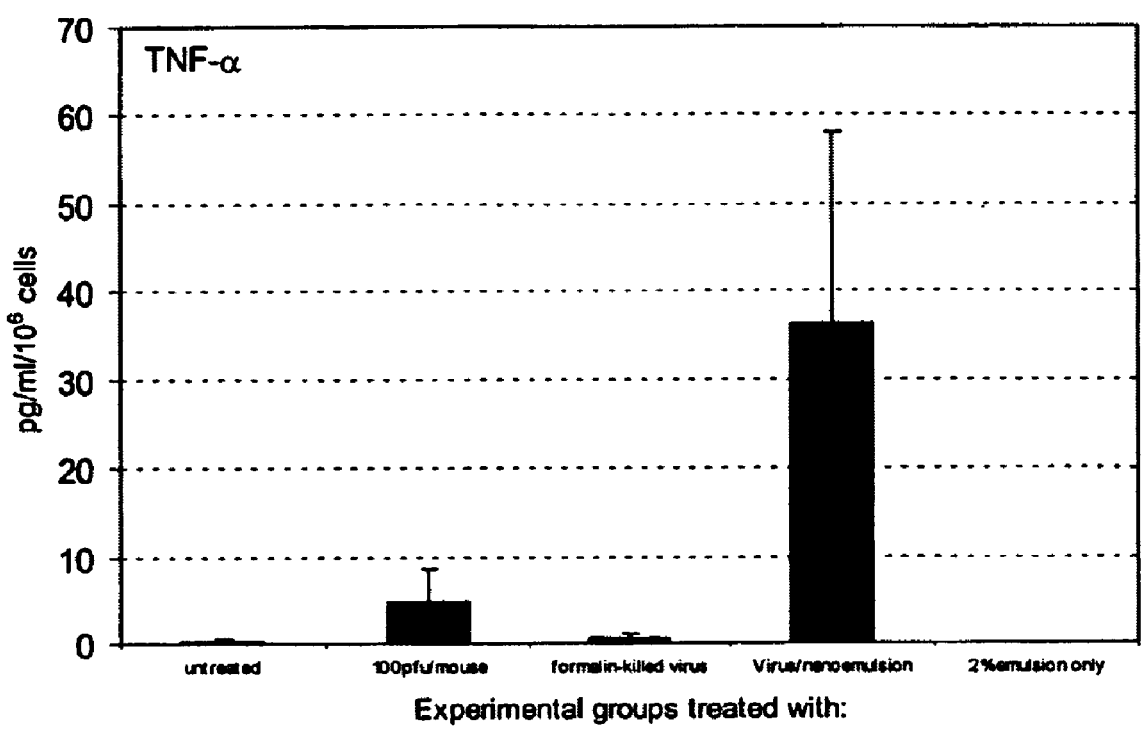
Figure 15C:
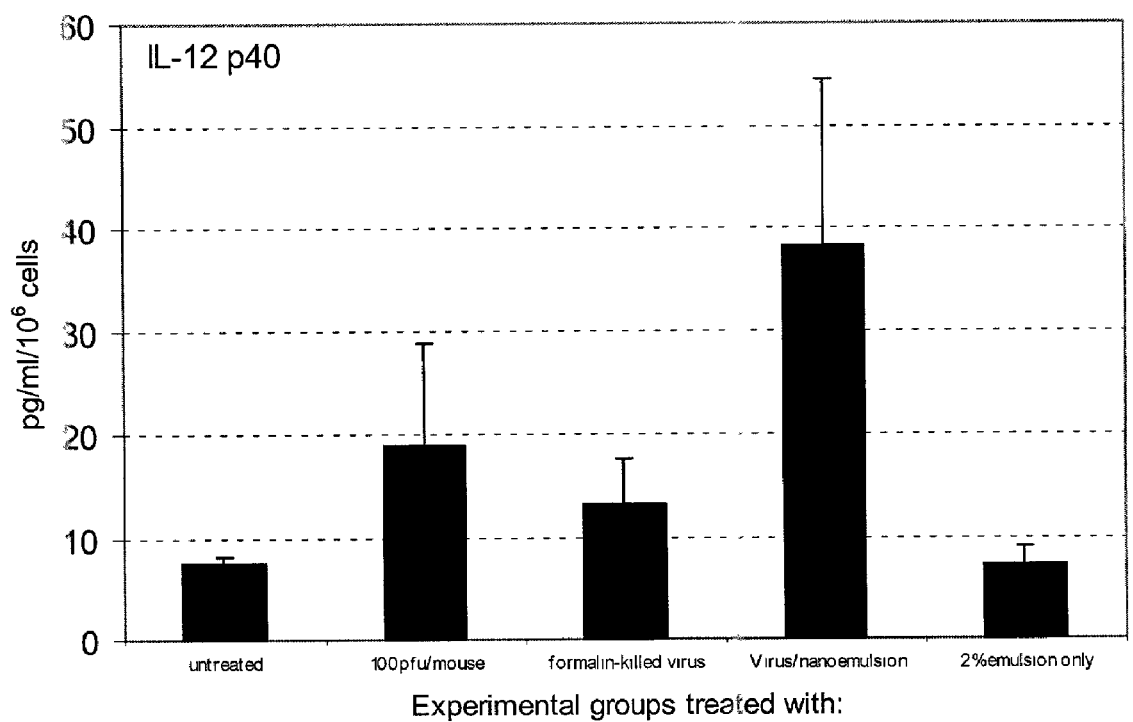
Figure 15D:
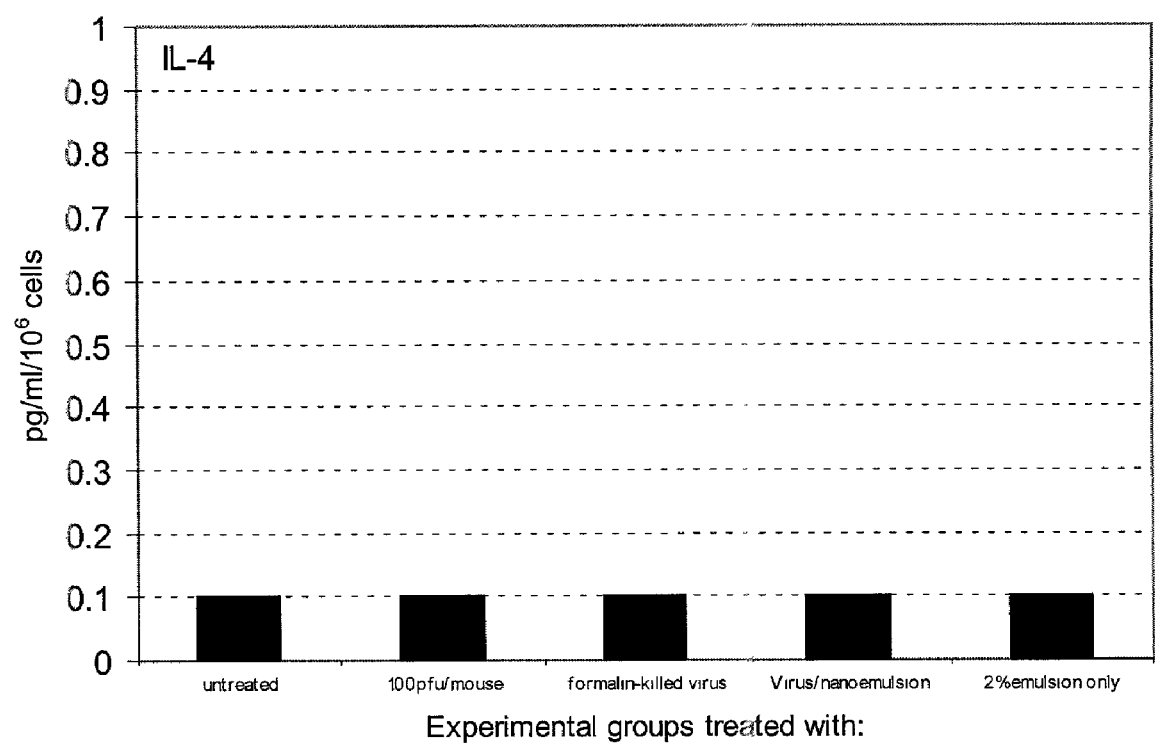
Figure 15E:
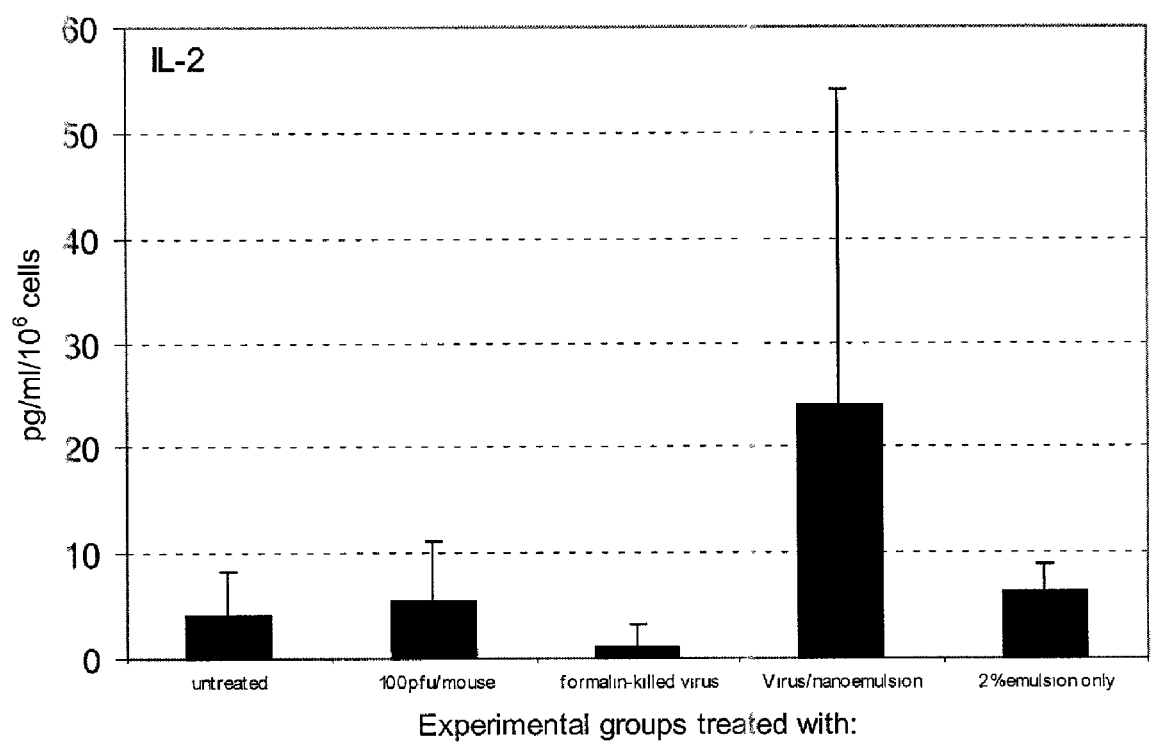
Figure 15F:
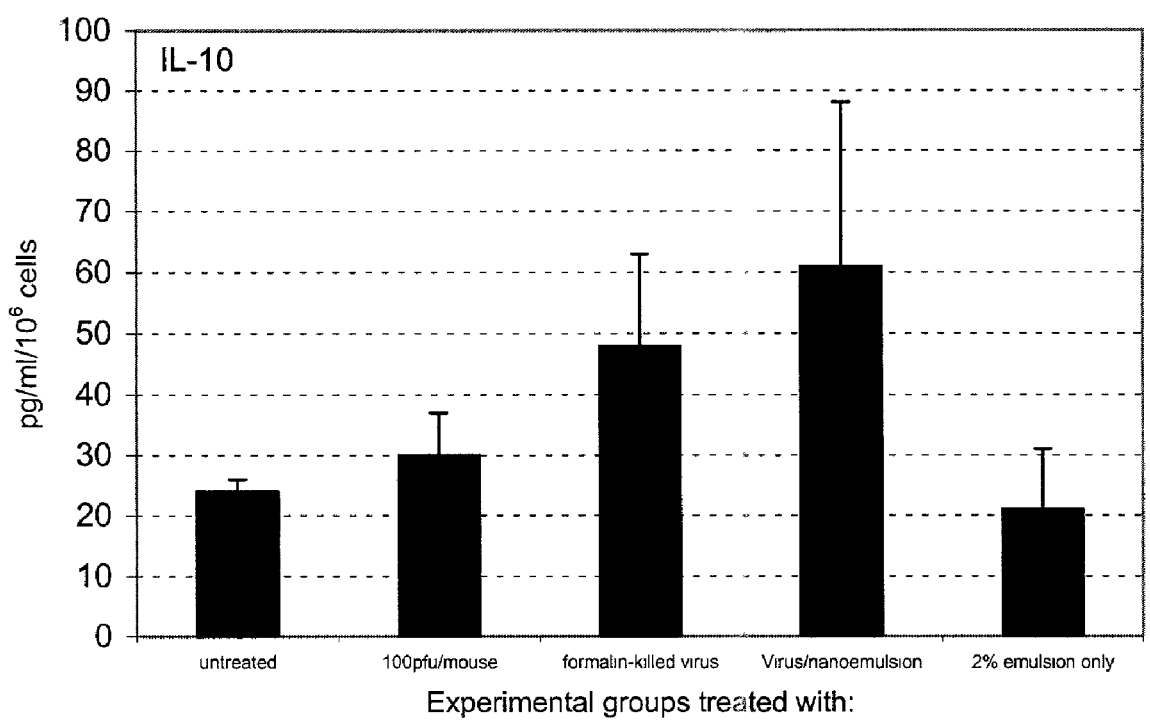
Figure 15G:
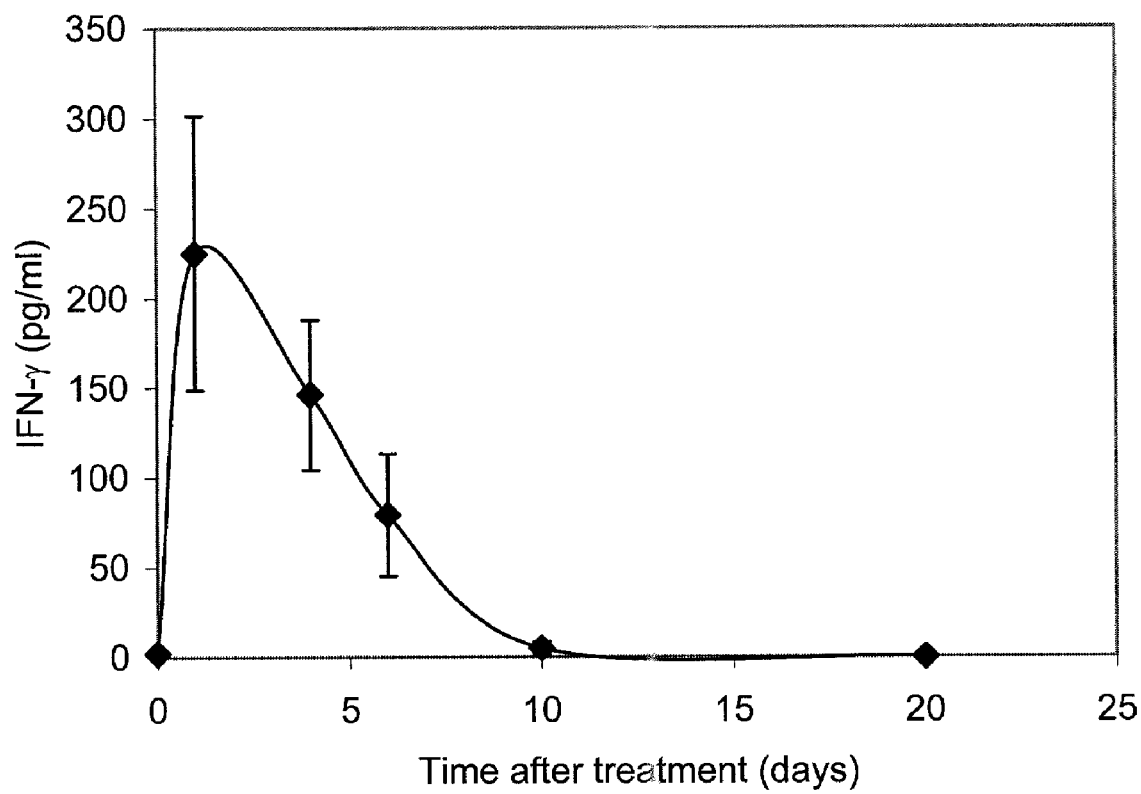

Since elevated IFN-$_\gamma$ was shown to indicate initial immune response, IFN-$_\gamma$ levels in serum of experimental animals were monitory up to day 20 after initial treatment. The levels of IFN-$_\gamma$ in serum obtained from mice treated with virus/nanoemulsion reached over 230 pg/ml at 24 h and gradually decreased to undetectable levels over a period of 20 days. The IFN-$_\gamma$ levels of the other experimental groups were low compared to the levels detected in the control group (FIG. 15g).

Antigen Specificity of Immune Response In Mice Treated With Virus/nanoemulsion.

The antigen specificity of immune responses was assessed using splenocyte proliferation and cytokine activation assays. Splenocytes were harvested on day 20 of the experiment from mice treated with virus/nanoemulsion and nanoemulsion alone. Cells were stimulated with congenic virus (AA strain used for intranasal treatment) for 5 days. As shown in FIG. 16, influenza A/AA strain specifically stimulated splenocytes harvested from mice treated with congenic virus/nanoemulsion mixture while no proliferation was detected in splenocytes harvested from any other group of animals. The stimulation index was less than 1, indicating that during 5 days of incubation virus killed some cells in the tissue culture. On day 35 of experiment (14 days after lethal challenge), splenocytes harvested from animals that survived the challenge showed greater proliferation index compared with the proliferation response of splenocytes obtained from the same group of animals on day 20.

Cytokine production was analyzed to characterize the nature of the immune response and confirm antigen specificity. The conditioned media obtained form splenocytes treated the same way as for the proliferation assay and incubated for 72 h was used to quantitate cytokine concentration. On day 20 splenocytes obtained from mice treated with virus/nanoemulsion produced high levels of IFN-$_\gamma$ and slightly increased levels of IL-2 (FIGS. 17a and 17b). There was no detectable production of IL-4 in resting or virus-stimulated cells (FIG. 17c). In splenocytes obtained from animals after challenge, viral stimulation resulted in further amplification of IFN-$_\gamma$ and IL-2 expression, reaching concentrations at least five fold higher than in animals before challenge (day 20). Major differences were also detected in the IL-4 expression. In contrast to their pre-challenge status, IL-4 was detected in non-stimulated, and over five-fold increased in congenic virus stimulated splenocytes (FIG. 17c). No specific activation of IFN-$_\gamma$, or other cytokines in splenocytes obtained from animals treated with nanoemulsion alone, viral RNA/nanoemulsion or with formaline-killed virus/nanoemulsion was observed.

Characteristics of Immunocompetent Cells

The ratios of T:B (CD3:CD19) and Th:Tc (CD4:CD8) cells in spleens of experimental animals were examined. In spleens of naïve mice 32% of T cells and 39% of CD8 positive cells were detected using immunostaining and flow cytometry analysis. Twenty one days after intranasal vaccination the percentage of T cells remained unchanged in groups of animals treated with virus/nanoemulsion mixture and nanoemulsion alone while CD8 positive cells were elevated in these groups to 48% and 44%, respectively. Fourteen days after lethal challenge (day 35 after immunization), the only surviving animals were in the group treated with virus/nanoemulsion mixture. All animals had significantly ($p<0.0001$) elevated T cells and slightly elevated CD8 positive cells compared with the same group before the challenge (FIG. 18). While T cells remained at the same level, the CD8 positive cells increased in the groups treated with nanoemulsion alone and virus pre-incubated with nanoemulsion.

Expansion of Epitope Recognition 20 days after intranasal instillation of virus Ann Arbor strain/nanoemulsion or nanoemulsion alone, mice were challenged with either congenic (AA) or heterogenic (Puerto Rico) strain of virus and observed for 14 days. Animals treated with virus Ann Arbor strain/nanoemulsion and challenged with congenic virus survived and recovered, animals from all other groups succumbed to pneumonia and died by day 26 of experiment (FIG. 19). The analysis of IFN-$_\gamma$ cytokine production in animals after the challenge revealed that splenocytes from this group of animals responded to in vitro stimulation with both congenic and heterogenic virus by profound production of cytokine (FIG. 20b) The present invention is not limited to a particular mechanism. Indeed, an understanding of the mechanism is not necessary to practice the present invention. Nonetheless, it is contemplated that animals that survived the challenge with congenic virus acquired immunity also against heterogenic virus and thereby expanded their epitope recognition. In order to examine such possibility, animals that survived the challenge with congenic virus were rechallenged with heterogenic virus (Puerto Rico strain) and observed for additional 14 days. All animals survived the rechallenge with heterogenic virus without any signs of sickness (Table 30).

In conclusion, the present example demonstrates in vivo the adjuvanticity of nanoemulsion for influenza vaccine given intranasally. The results establish that a single intranasal administration of nanoemulsion mixed with virus produces the full protection against influenza pnemonitis, resulting in survival of all animals challenged with lethal dose of the virus. During the course of challenge, immunized animals did not show any signs of illness and their core body temperature was within a normal range for 14 days. Moreover, lungs of survived animals did not show gross pathological changes characteristic for influenza pneumonitis.

TABLE 30

Survival (%) of animals after vaccination, challenge and cross challenge with influenza A virus Puerto Rico strain

| Time (days) | Vaccination with: | | |
|---|---|---|---|
| | nanoemulsion | nanoemulsion + $2 \times 10^5$ pfu of AA | nanoemulsion |
| 0 | 100* | 100 | 100 |
| 1 | 100 | 100 | 100 |
| 2 | 100 | 100 | 100 |
| 3 | 100 | 100 | 100 |
| 4 | 100 | 100 | 100 |
| 5 | 100 | 100 | 100 |
| 6 | 100 | 100 | 100 |
| 7 | 100 | 100 | 100 |
| 8 | 100 | 100 | 100 |
| 9 | 100 | 100 | 100 |
| 10 | 100 | 100 | 100 |
| 11 | 100 | 100 | 100 |
| 12 | 100 | 100 | 100 |
| 13 | 100 | 100 | 100 |
| 14 | 100 | 100 | 100 |
| 15 | 100 | 100 | 100 |
| 16 | 100 | 100 | 100 |
| 17 | 100 | 100 | 100 |
| 18 | 100 | 100 | 100 |
| 19 | 100 | 100 | 100 |
| 20 | 100 | 100 | 100 |
| Challenge with: | $1 \times 10^5$ pfu of AA | $1 \times 10^5$ pfu of AA | $1 \times 10^4$ pfu of PR |
| 21 | 100 | 100 | 100 |
| 22 | 100 | 100 | 100 |
| 23 | 100 | 100 | 100 |
| 24 | 0 | 100 | 100 |
| 25 | 0 | 100 | 100 |
| 26 | 0 | 100 | 100 |
| 27 | 0 | 100 | 20 |
| 28 | 0 | 100 | 0 |
| 29 | 0 | 100 | 0 |
| 30 | 0 | 100 | 0 |
| 31 | 0 | 100 | 0 |
| 32 | 0 | 100 | 0 |
| 33 | 0 | 100 | 0 |
| 34 | 0 | 100 | 0 |
| Challenge with: | | $1 \times 10^4$ pfu of PR | |
| 35 | none available | 100 | none available |
| 36 | | 100 | |
| 37 | | 100 | |
| 38 | | 100 | |
| 39 | | 100 | |
| 40 | | 100 | |
| 41 | | 100 | |
| 42 | | 100 | |
| 43 | | 100 | |
| 44 | | 100 | |
| 45 | | 100 | |
| 46 | | 100 | |
| 47 | | 100 | |
| 48 | | 100 | |
| 49 | | 100 | |

*number of animals used was 5-8 per group

Example 16

Immune Response to HIV gp120

This example describes the immune response of mice to recombinant HIV-1 envelope glycoprotein (gp120). Recombinant gp120 glycoprotein at concentrations of 2 and 20 μg per dose mixed with varying concentrations of X8P nanoemulsion (final concentration: 0.1 to 1%) in 100 μl volume was administered intranasally or intramuscularly into mice. Dose administration was repeated within three weeks after the first immunization. Protein in saline was placed in the nose of control animals. GP120/X8P was also injected intramuscularly in order to determine if it could adjunct intramuscularly administered vaccines.

Results are shown in FIGS. 21 and 22. Serum levels of specific anti-gp120 IgG were detected six weeks after initial immunization. Increased and comparable levels of immune responses were detected for both routes of immunization. FIG. 21 demonstrates that administration of X8P nanoemulsion with gp120 resulted in an increased immune response when the gp120 was administered intranasally. FIG. 22 demonstrates that administration of X8P nanoemulsion with gp120 resulted in an increased immune response when the gp120 was administered intramuscularly.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A method of inducing an immune response to an immunogen, comprising:

a) providing:

(i) a nanoemulsion, wherein said nanoemulsion comprises:

1. oil;
2. ethanol;
3. a surfactant;
4. a quaternary ammonium compound; and
5. distilled water; and (ii) an immunogen;

b) combining said nanoemulsion with said immunogen; and c) administering said combined nanoemulsion and immunogen to a subject under conditions such that said subject produces an immune response to said immunogen, wherein said administering comprises contacting said combined nanoemulsion and immunogen with a mucosal surface of said subject.

2. The method of claim 1, wherein said immunogen is a pathogen.

3. The method of claim 2, wherein said pathogen comprises an inactivated pathogen.

4. The method of claim 1, wherein said immunogen comprises a pathogen product.

5. The method of claim 1, wherein said administering produces a mucosal immune response against said immunogen.

6. The method of claim 1, wherein said administering comprises intranasal administration.

7. The method of claim 1, wherein said oil is selected from the group consisting of soybean, avocado, squalene, olive, canola, corn, rapeseed, safflower, sunflower, fish, flavor, and water insoluble vitamins.

8. The method of claim 1, wherein said surfactant is selected from the group consisting of nonionic and ionic surfactants.

9. The method of claim 8, wherein said surfactant is selected from the group consisting of Polyethylene glycol tert-octylphenyl ether t-Octylphenoxypolyethoxyethanol 4-(1,1,3,3-Tetramethylbutyl)phenyl-polyethylene glycol (TRITON X-100); Polyoxyethylenesorbitan monolaurate Polyethylene glycol sorbitan monolaurate (TWEEN 20); and 4-(1,1,3,3-Tetramethylbutyl)phenol polymer with formaldehyde and oxirane (TYLOXAPOL).

10. The method of claim 1, wherein said nanoemulsion further comprises a cationic halogen containing compound.

11. The method of claim 10, wherein said cationic halogen containing compound is selected from the group consisting of cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides.

12. The method of claim 10, wherein said cationic halogen containing compound comprises a halide selected from the group consisting of chloride, fluoride, bromide, and iodide.

13. The method of claim 1, wherein said quaternary ammonium compound is cetylpyridinium chloride.

14. The method of claim 1, wherein said quaternary ammonium containing compound is selected from the group consisting of Alkyl dimethyl benzyl ammonium chloride, dialkyl dimethyl ammonium chloride, n-Alkyl dimethyl benzyl ammonium chloride, and n-Alkyl dimethyl ethylbenzyl ammonium chloride.

15. The method of claim 1, wherein said immunogen is selected from the group consisting of virus, bacteria, fungus and pathogen products derived from said virus, bacteria, or fungus.

16. The method of claim 15, wherein said virus is selected from the group consisting of influenza A, herpes simplex virus I, herpes simplex virus II, sendai, sindbis, vaccinia, parvo, human immunodeficiency virus, hepatitis B virus, hepatitis C virus, hepatitis A virus, cytomegalovirus, human papilloma virus, picornavirus, hantavirus, junin virus, and ebola virus.

17. The method of claim 15, wherein said bacteria is selected from the group consisting of *Bacillus cereus, Bacillus circulars* and *Bacillus megaterium, Bacillus anthracis, Clostridium perfringens, Vibrio cholerae, Streptococcus pyogenes, Streptococcus agalactiae, Streptococcus pneumonia, Staphylococcus aureus, Neisseria gonorrhoeae, Haemophilus influenzae, Escherichia coli, Salmonella typhimurium, Shigella dysenteriae, Proteus mirabilis, Pseudomonas aeruginosa, Yersinia enterocolitica,* and *Yersinia pseudotuberculosis.*

18. The method of claim 15, wherein said fungus is selected from the group consisting of *Candida, Aspergillus, Fusarium,* and *Trichophyton.*

19. The method of claim 1, further comprising repeating step c) administering said combined nanoemulsion and immunogen to a subject.

20. The method of claim 1, wherein said subject exhibits a higher titer of immunogen-specific antibodies relative to a subject not administered said combined emulsion and immunogen.

21. The method of claim 20, wherein said immunogen-specific antibodies comprise IgG antibodies.

22. The method of claim 1, wherein said subject exposed to said combined nanoemulsion and immunogen exhibits elevated serum levels of IFN-γ compared to the levels found within a subject not administered said combined nanoemulsion and immunogen.

23. The method of claim 20, wherein said immunogen-specific antibodies comprise IgA antibodies.

* * * * *